(12) United States Patent
Forchheim et al.

(10) Patent No.: US 8,058,225 B2
(45) Date of Patent: Nov. 15, 2011

(54) **PROTEINS FOR USE IN HUMAN AND ANIMAL *STAPHYLOCOCCUS* INFECTIONS**

(75) Inventors: Michael Forchheim, Regensburg (DE); Holger Grallert, Regensburg (DE); Anja Philipp, Regensburg (DE); Manfred Biebl, Regensburg (DE)

(73) Assignee: Hyglos Invest GmbH, Bernried (DE)

( * ) Notice: Subject to any disclaimer, the term of this patent is extended or adjusted under 35 U.S.C. 154(b) by 431 days.

(21) Appl. No.: 12/194,320

(22) Filed: Aug. 19, 2008

(65) Prior Publication Data

US 2009/0202512 A1    Aug. 13, 2009

Related U.S. Application Data

(60) Provisional application No. 60/957,351, filed on Aug. 22, 2007, provisional application No. 61/032,211, filed on Feb. 28, 2008.

(30) Foreign Application Priority Data

Aug. 22, 2007 (EP) ..................... 07114785
Feb. 28, 2008 (EP) ..................... 08152096

(51) Int. Cl.
*C07K 14/00* (2006.01)
(52) U.S. Cl. .................................. 514/1; 530/350
(58) Field of Classification Search .............. None
See application file for complete search history.

(56) References Cited

U.S. PATENT DOCUMENTS

| | | | | |
|---|---|---|---|---|
| 5,997,862 | A | 12/1999 | Fischetti et al. | 424/94.1 |
| 7,608,276 | B2 * | 10/2009 | Masignani et al. | 424/243.1 |
| 2007/0077235 | A1 | 4/2007 | Loomis et al. | 424/93.2 |

FOREIGN PATENT DOCUMENTS

GB  2255561  11/1992

OTHER PUBLICATIONS

Kuroda et al. 2001; Whole genome sequencing of meticillin-resistant *Staphyloccus aureus*. Lancet 357: 1225-1240.*
Iandolo et al. 2002; Comparative analysis of the genomes of the terperate bacteriophages phi11, phi12, and phi13 of *Staphylococcus aureus* 8325. Gene 289: 109-118.*
Kwan et al. .2005; The complete genomes and protons of 27 *Staphylococcus aureus* bacteriophages. PNAS 102: 5174-5179.*
Cheng et al., "Removal of group B Streptococci olonizing the vagina and oropharynx of mice with a bacteriophage lytic enzyme," *Antimicrob. Agents Chemother.*, 49:111-117, 2005.
Databank Accession No. NC_007793, Jul. 28, 2008.
Diep et al., "Complete genome sequence of USA300, an epidemic clone of community-acquired meticillin-resistant *Staphylococcus aureus*," *The Lancet*, 367:731-739, 2006.
Entenza et al., "Therapeutic effects of bacteriophage Cpl-1 lysin against *Streptococcus pneumoniae* endocarditis in rats," *Antimicrob. Agents Chemother.*, 49:4789-4792, 2005.
Fischetti, *BMC Oral Health*, 6:16-19, 2006.
Loeffler et al., "Rapid killing of *Streptococcus pneumoniae* with a bacteriophage cell wall hydrolase," *Science*, 294:2170-2172, 2001.
Lu et al., "Cell wall-targeting domain of glycylglycine endopeptidase distinguishes among peptidoglycan cross-bridges," *J. Biol. Chem.*, 281:549-558, 2006.
Nelson et al., "Prevention and elimination of upper respiratory colonization of mice by group A Streptococci by using a bacteriophage lytic enzyme," *Proc. Natl. Acad. Sci. USA*, 98:4107-4112, 2001.
Schuch et al., "A bacteriolytic agent that detects and kills *Bacillus anthracis*," *Nature*, 418:884-889, 2002.

* cited by examiner

*Primary Examiner* — Karen Carlson
(74) *Attorney, Agent, or Firm* — Fulbright & Jaworski

(57) ABSTRACT

The present invention relates to a polypeptide termed ply_pitti26 comprising the sequence as depicted in SEQ ID NO:1 as well as variants of this polypeptide. Furthermore, the present invention relates to nucleic acids and vectors encoding for said polypeptide and variants thereof as well as host cells comprising these nucleic acids and/or vectors. Finally, the present invention relates to the uses of said polypeptide, variants thereof, nucleic acid sequences, vectors and host cells, in particular for the treatment or prophylaxis of a subject infected by or exposed to *Staphylococci*.

14 Claims, 14 Drawing Sheets

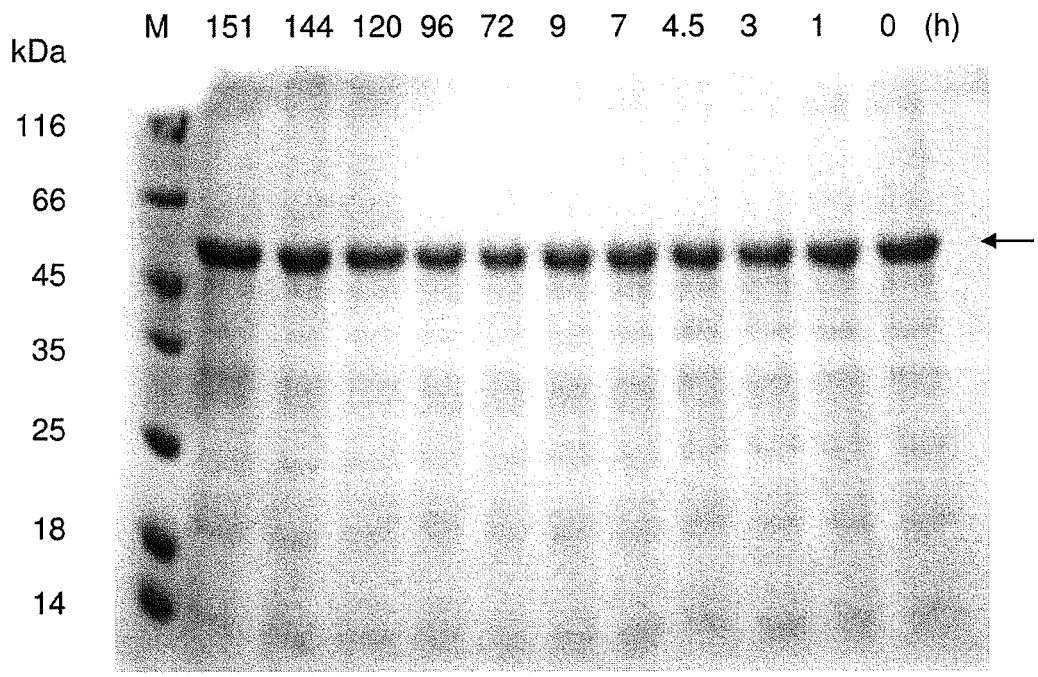
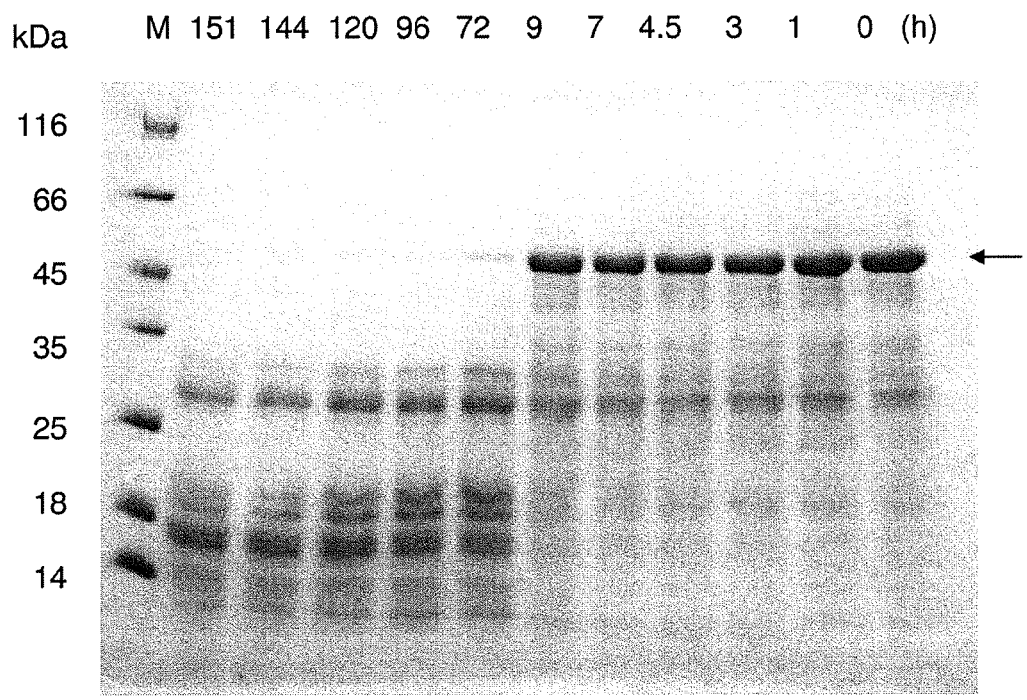
FIG. 7

A

MASIIMEVATMQAKLTKKEFIEWLKTSEGKQFNVDLWYGFQCFDYANAGWKVLFGHTLKG
LGAKDIPFANNFDGLATVYQNTPDFLAQPGDMVVFGSNYGAGYGHVAWVIEATLDYIIVY
EQNWLGGGWTDRIEQPGWGWEKVTRRQHAYDFPMWFIRPNFKSATAPASIQSPTQASKKE
TAKPQPKAVELKIIKDVVKGHDLPKRGGNPKGIVIHNDAGSKGATAEAYRNGLVNAPSSR
LEAGIAHSYVSGNTVWQALDESQVGWHTANQLGNKYYYGIEVCQSMGADNATFLKNEQAT
FQECARLLKKWGLPANRNTIRLHNEFTSTSCPHRSSVLHTGFDPVTRGLLPEDKRLQLKD
YFIKQIRAYMDGKIPVATVSNESSASSNTVKPVAELMPPVPAGYTLDKNNVPYKKEQGNY
TVANVKGNNVRDGYSTNSRITGVLPNNTTITYDGAYCINGYRWITYIANSGQRRYIATGE
VDIAGNRISSFGKFSAV

B

ATGGCAAGTATCATCATGGAGGTGGCGACAATGCAAGCAAAATTAACTAAAAAAGAGTTTATAGAGTGGTTGAAA
ACTTCTGAGGGAAAACAATTCAATGTGGACTTATGGTATGGATTTCAATGCTTTGATTATGCCAATGCTGGTTGG
AAAGTTTTGTTTGGACATACACTGAAAGGTTTAGGTGCAAAAGATATACCATTTGCAAACAATTTCGATGGACTA
GCTACTGTATACCAAAATACACCGGACTTTTTGGCACAACCCGGCGACATGGTTGTATTCGGTAGCAATTACGGT
GCAGGATACGGACACGTAGCATGGGTAATTGAAGCAACTTTAGATTATATCATTGTATATGAGCAGAATTGGCTA
GGCGGTGGCTGGACTGACAGAATCGAACAACCCGGCTGGGGTTGGGAAAAAGTTACAAGACGACAACATGCTTAC
GATTTCCCTATGTGGTTTATCCGTCCTAACTTCAAAAGCGCTACAGCTCCAGCTTCAATACAATCTCCTACGCAA
GCATCTAAAAAGGAAACAGCTAAGCCACAACCTAAAGCGGTAGAACTTAAAATTATCAAAGATGTGGTTAAAGGT
CATGACCTTCCTAAACGTGGTGGTAATCCTAAGGGTATAGTTATTCATAACGACGCAGGAAGCAAAGGGGCAACA
GCAGAAGCGTATCGAAACGGATTAGTTAACGCACCTTCATCAAGATTAGAAGCGGGTATTGCGCATAGTTATGTA
TCAGGTAACACAGTGTGGCAAGCTTTAGATGAATCGCAAGTAGGTTGGCATACTGCTAACCAATTAGGCAATAAA
TATTATTACGGTATTGAAGTGTGTCAATCAATGGGAGCGGATAATGCGACGTTTTTAAAAAATGAACAGGCGACT
TTCCAAGAATGCGCTAGATTGTTGAAAAAATGGGGATTACCAGCAAACAGAAATACAATCAGATTACACAACGAA
TTCACTTCAACATCATGCCCACACAGAAGCTCAGTATTGCACACTGGTTTTGACCCAGTAACTCGCGGTCTATTG
CCAGAAGACAAGCGGTTGCAACTTAAAGACTACTTTATCAAGCAGATTAGGGCGTACATGGATGGTAAAATACCG
GTTGCCACTGTCTCTAATGAGTCAAGCGCTTCAAGTAATACAGTTAAACCAGTTGCAGAGCTCATGCCACCAGTG
CCAGCAGGTTATACACTCGATAAGAATAATGTCCCTTATAAAAAAGAACAAGGCAATTACACAGTAGCTAATGTT
AAAGGTAATAATGTAAGAGACGGTTATTCAACTAATTCAAGAATTACAGGGGTATTACCCAACAACACAACAATT
ACGTATGACGGTGCATATTGTATTAATGGTTATAGATGGATTACTTATATTGCTAATAGTGGACAACGTCGCTAT
ATTGCGACCGGAGAGGTAGACATAGCAGGCAACCGAATAAGCAGTTTTGGTAAGTTTAGTGCAGTT

C

ATGGCGTCTATTATTATGGAAGTGGCGACCATGCAGGCGAAACTGACCAAAAAAGAATTCATCGAATGGCTGAAA
ACCAGCGAAGGCAAACAGTTTAACGTGGATCTGTGGTATGGCTTTCAGTGCTTTGATTATGCGAACGCGGGCTGG
AAAGTGCTGTTTGGCCATACCCTGAAAGGCCTGGGCGCGAAAGATATTCCGTTTGCGAATAACTTTGATGGCCTG
GCCACCGTGTATCAGAACACCCCGGATTTTCTGGCCCAGCCGGGCGATATGGTGGTGTTTGGCAGCAACTATGGC
GCGGGTTATGGCCATGTGGCGTGGGTGATTGAAGCGACCCTGGATTATATCATCGTGTACGAACAGAACTGGCTG
GGCGGTGGCTGGACCGATCGTATTGAACAGCCGGGCTGGGGCTGGGAAAAAGTGACCCGTCGTCAGCATGCGTAC
GATTTTCCGATGTGGTTTATTCGCCCGAACTTTAAATCTGCGACGGCCCCGGCGAGCATTCAGAGCCCGACCCAG
GCGAGCAAAAAAGAAACCGCGAAACCGCAGCCGAAAGCGGTGGAACTGAAAATCATCAAAGATGTGGTGAAAGGC
CATGATCTGCCGAAACGTGGCGGCAATCCGAAAGGCATTGTGATTCATAACGATGCGGGCAGCAAAGGTGCGACC
GCGGAAGCGTATCGTAACGGCCTGGTGAACGCGCCGAGCAGCCGTCTGGAAGCGGGCATTGCGCATAGCTATGTG
AGCGGCAACACCGTGTGGCAGGCGCTGGATGAAAGCCAGGTGGGCTGGCATACCGCGAACCAGCTGGGCAACAAA
TATTATTACGGCATCGAAGTGTGCCAGAGCATGGGCGCGGATAACGCGACCTTTCTGAAAAACGAACAGGCGACC
TTTCAGGAATGCGCGCGTCTGCTGAAAAAATGGGGCCTGCCGGCGAACCGTAACACCATTCGTCTGCATAACGAA
TTTACCAGCACCAGCTGCCCGCATCGTAGCAGCGTGCTGCATACCGGCTTTGATCCGGTGACCCGTGGCCTGCTG
CCGGAAGATAAACGTCTGCAGCTGAAAGATTATTTCATCAAACAAATCCGCGCGTATATGGATGGCAAAATTCCG
GTGGCGACCGTGAGCAACGAAAGCAGCGCGAGCAGCAATACCGTGAAACCGGTGGCGGAACTGATGCCGCCGGTT
CCGGCCGGTTATACCCTGGATAAAAACAACGTGCCGTATAAAAAAGAACAGGGCAACTATACCGTGGCGAACGTG
AAAGGCAACAACGTGCGTGATGGCTATAGCACCAACAGCCGTATTACCGGCGTGCTGCCGAACAACACCACCATT
ACCTATGATGGCGCGTATTGCATTAACGGCTATCGCTGGATTACCTATATCGCGAACAGCGGCCAGCGTCGTTAT
ATTGCGACCGGCGAAGTGGATATTGCGGGCAACCGTATTAGCAGCTTTGGTAAATTTAGCGCGGTG

FIG. 10

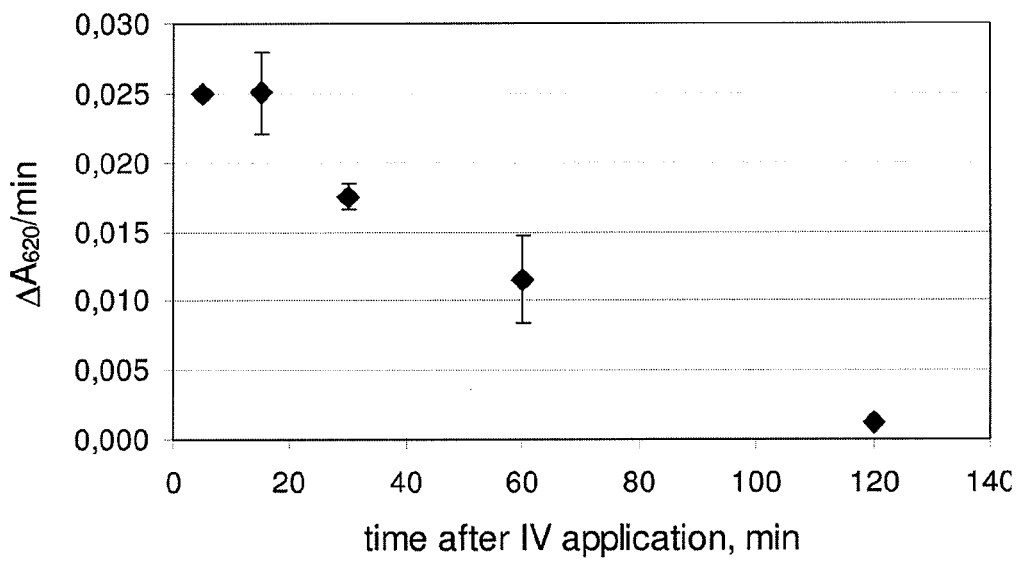
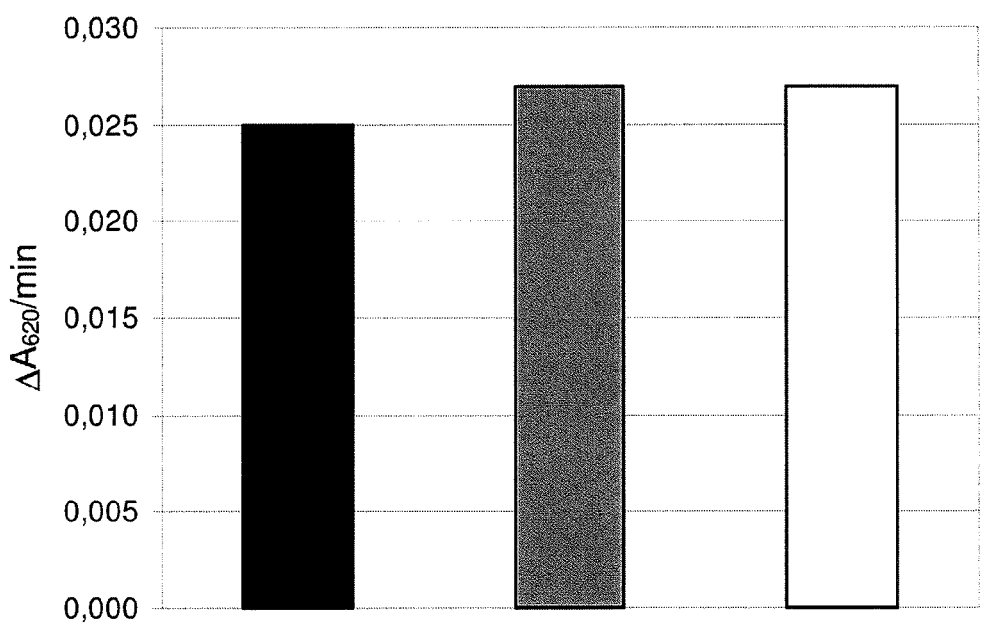
FIG. 14

PROTEINS FOR USE IN HUMAN AND ANIMAL *STAPHYLOCOCCUS* INFECTIONS

The present application claims benefit of priority to U.S. Provisional Applications 60/957,351, filed on Aug. 22, 2007 and 61/032,211, filed Feb. 28, 2008, and European Patent Applications EP 07 114 785.4, filed Aug. 22, 2007 and EP 08 152 096.7, filed Feb. 28, 2008. The entire contents of each of these applications being incorporated herein by reference.

BACKGROUND OF THE INVENTION

A. Field of the Invention

The present invention relates to a polypeptide termed ply_pitti26 comprising the sequence as depicted in SEQ ID NO:1 as well as variants of this polypeptide. Furthermore, the present invention relates to nucleic acids and vectors encoding for the polypeptide and variants thereof as well as host cells comprising these nucleic acids and/or vectors. Finally, the present invention relates to the uses of the polypeptide, variants thereof, nucleic acid sequences, vectors and host cells, in particular for the treatment or prophylaxis of a subject infected by or exposed to *Staphylococci*.

B. Background of the Invention

1. Bacterial Infections

Staphylococcal infections are a major cause of severe diseases with high mortality all over the world. The gram-positive pathogen *Staphylococcus aureus* is responsible for a variety of infections of the skin and soft tissues as well as life-threatening infections like bacteremia and endocarditis. In addition, *Staphylococcus aureus* is frequently involved in food poisoning. Due to its tolerance to low pH values and high salt conditions this pathogen grows in a variety of food products, especially of animal origin, producing a heat stable enterotoxin. Persons with a particular risk of infection are patients after surgery or during hemodialysis as well as premature infants and immunocompromised persons, or those with need for prosthetic devices. Staphylococcal infections are of particular global health concern because of their high distribution (about 25-30% of the population are asymptomatic carriers) and of the increasing emergence of antibiotic resistant strains of *Staphylococcus aureus*. MRSA (methicillin-resistant *Staphylococcus aureus*) is a prominent member of this group and a major cause of nosocomial infections. In addition, there are many multiresistant strains, even those which are resistant to the "drugs of the last line of defence" like vancomycin, linezolid or daptomycin. Infections with antibiotic resistant *staphylococci* rise enormous costs to the global health budgets, because the patients often need long-term stay in a hospital and have to be isolated from other patients.

Besides the coagulase-positive *S. aureus*, pathogens from the group of the coagulase-negative *staphylococci* are of importance. *S. haemolyticus*, for example, causes keratitis, *S. epidermidis* is frequently found in biofilms on implanted devices which are associated with serious infections (endoplastitis) and *S. saprophyticus* is responsible for urinary tract infections. Apart from infections of humans, cattle infections also play an important role. Especially, bovine mastitis, an infection of the mammary glands, is of commercial significance. Apart from *S. aureus* it is caused by some coagulase-negative *staphylococci* like *S. epidermidis*, *S. simulans*, *S. chromogenes*, *S. hyicus*, *S. warneri* and *S. xylosus*.

Standard antibiotic therapy is becoming more and more ineffective. Hence, new strategies for treating bacterial infections are needed. They include the development of new antibiotics as well as the search for antimicrobial peptides. Uses of antibodies and putative vaccines or phage therapy are alternative approaches. However all of these methods exhibit serious disadvantages. At widespread use, novel antibiotics also will rise new resistances, antimicrobial peptides and monoclonal antibodies require a lot of additional investments until a routine use in therapy will be possible; immunization strategies against *Staphylococcus aureus* were not successful so far and phage therapy causes problems with immune response and tissue penetration as well as with a potential undesired transfer of bacterial toxins by the phages. The use of isolated peptidoglycan hydrolases, the so-called endolysins, represents an advancement of the phage therapy. Endolysins enzymatically hydrolyse the cell walls of those bacteria which are host organisms for their corresponding bacteriophages.

2. Bacterial Endolysins

After infection of the host bacterium, bacteriophages produce new phage particles within the host cell. At the end of the reproduction cycle the host cell must be lysed, to set free the new phage generation. Endolysins are produced as a tool for this lysis of the host cell. It was found, that endolysins also act on bacterial cell walls when they are added exogenously to non infected bacterial cells ("lysis from without"). The use of endolysins to kill contaminating bacteria in food was first disclosed by Gasson in 1991 (GB 2,255,561). First therapeutic and prophylactic applications in vivo using mouse model systems were described in 2001 by the group of Fischetti (Nelson & Fischetti, 2001; Loeffler et al., 2001). This work describes the topical application of endolysins against group A streptococci (oral application) and against pneumococci (nasopharyngeal application). Later, an application against *Bacillus anthracis* was added (Schuch et al., 2002). Entenza et al. (2005) report the use of Cpl-1 lysin against pneumococci causing endocarditis in rats. Endolysin PlyGBS was used to kill group B streptococci in the vagina and oropharynx of a mouse model (Cheng et al., 2005). Fischetti (2006) summarizes the use of phage lytic enzymes to control pathogenic bacteria.

In U.S. Pat. No. 5,997,862 a multitude of methods of treatments and pharmaceutical compositions to treat and prevent bacterial infections using phage derived lysins is disclosed. Several further patents teach specific compositions and uses of phage derived lysins for treatment of, e.g., dermatological infections, ocular infections, infections of mouth and teeth, infections of the respiratory tract, various illnesses, bacterial infections in general, the parenteral use of lysin compositions, and the use of bandage compositions. U.S. Patent Publication No. 2007/077235 describes lysin compositions to treat mastitis in animals.

Endolysins may be divided into five classes: (1) N-acetylmuramidases (lysozymes), (2) endo-β-N-acetylglucosaminidases, and (3) lytic transglycosylases, which all cleave the sugar moiety of peptidoglycan, (4) endopeptidases, which cleave the peptide moiety, and (5) N-actylmuramoyl-L-alanine amidases, which cut the amide bond between sugar backbone and peptide linkers. Endolysins show a modular organization exhibiting a combination of different polypeptide domains showing enzymatic activity or cell binding activity, the so-called EADs (enzymatically active domains) and CBDs (cell binding domains), respectively. Mostly, EADs are located at the N-terminal part of the endolysins, and CBDs at the C-terminal parts, but there are also exceptions of this rule of thumb. It is also shown that modules can be exchanged between different cell wall lytic enzymes producing new functional enzymes, which sometimes exhibit even new functional properties (Diaz et al., 1990; Croux et al., 1993; Donovan et al., 2006).

Since endolysins are typically more specific than antibiotics, it is unlikely that resistance development will rapidly occur. Therefore, the use of suitable endolysins acting on *staphylococcus* bacteria is a desirable means for the fight against the respective infections. Several endolysins active against *staphylococcus* bacteria are already described in the relevant art. Protein 17 associated with phage P68 is a staphylococcal endolysin which exhibits antimicrobial activity also against clinical *S. aureus* isolates (Takac et al., 2005). The endolysin plyTW derived from the *S. aureus* phage Twort needs only the N-terminal enzymatically active fragment for hydrolytic activity against bacterial cells, whereas the C-terminal part with homology to lysostaphin seems dispensable (Loessner et al., 1998). Donovan et al. (2006) created a chimeric endolysin between *Streptococcus agalactiae* B30 endolysin and lysostaphin of *Staphylococcus simulans* with potential use in treatment of mastitis. Several groups used the endolysin of *Staphylococcus aureus* bacteriophage phi11 in antimicrobial applications. Navarre et al. (1999) identified multiple enzymatic activities in phi11 endolysin, and showed that a mutant with deletion of the amidase domain is still active. Donovan et al. (2006) used complete phi11 endolysin as well as C-terminally truncated versions in assays against mastitis pathogens. Different mutants of phi11 endolysin and phi12 endolysin were tested in different activity assays on *Staphylococcus aureus* cell walls, heat inactivated cells and also bacterial biofilms (Sass & Bierbaum, 2007). The endolysin of the *Staphylococcus warneri* phage ΦWMY, LysWMY, although reported to be closely related to phi11 endolysin, retained full activity when the amidase as well as the cell binding domains were deleted (Yokoi et al., 2005). This result indicates that the functions of and interactions between the different endolysin modules are not equivalent even in closely related endolysins.

Although different endolysins against *staphylococcus* bacteria are known from the art, there is still a need for efficient staphylococcal endolysins that can be produced in an efficient way and in addition show high activity against microorganisms of the genus *Staphylococcus*.

SUMMARY OF THE INVENTION

The present invention relates to a polypeptide termed ply_pitti26 comprising the sequence as depicted in SEQ ID NO:1 as well as variants of this polypeptide. Furthermore, the present invention relates to nucleic acids and vectors encoding for the polypeptide and variants thereof as well as host cells comprising these nucleic acids and/or vectors. Finally, the present invention relates to the uses of the polypeptide, variants thereof, nucleic acid sequences, vectors and host cells, in particular for the treatment or prophylaxis of a subject infected by or exposed to *Staphylococci*.

In more particular aspects in accordance with the present invention, there is provided a polypeptide comprising the sequence as depicted in SEQ ID NO:1 or variant thereof, said variant being:
 a) a polypeptide comprising a sequence in which the CBD of SEQ ID NO:1 has been replaced by a CBD domain of another *Staphlococci* specific endolysin; or
 b) a polypeptide comprising the sequence of SEQ ID NO:1 except for at least the first N-terminal amino acid and at most the first 28 N-terminal amino acids of SEQ ID NO:1; or
 c) a polypeptide comprising one or more point mutations or amino acid substitutions in the sequence of SEQ ID NO:1; or
 d) a polypeptide comprising in addition to the sequence of SEQ ID NO: 1 sequences representing marker moieties, tags or other functional polypeptide sequences; or
 e) a polypeptide comprising one or more additional amino acid residues inserted into the amino acid sequence according to SEQ ID NO:1; or
 f) a polypeptide comprising a polypeptide sequence representing any combination of variants a), b), c), d) and e).

The variant of the polypeptide may comprise the sequence as depicted in SEQ ID NO:1 comprises an endolysin cell binding domain of the SH3 type. The variant of the polypeptide may comprise the sequence as depicted in SEQ ID NO:1 comprises a CBD domain selected from the endolysin CBD domains of ply_USA or ply_pitti20. The variant of the polypeptide may comprise the sequence as depicted in SEQ ID NO:1 comprises a CBD domain as denoted in SEQ ID NOs: 3 or 5, or more particular, the sequence as denoted in SEQ ID NOs: 7 or 11. The polypeptide may also comprise the sequence as depicted in SEQ ID NO:1 lacks 1, 2, 3, 4, 5, 6, 7, 8, 9, 10, 11, 12, 13, 14, 15, 16, 17, 18, 19, 20, 21, 22, 23, 24, 25, 26, 27 or 28 N-terminal amino acid residues of SEQ ID NO:1. Where the variant of the polypeptide comprise the sequence as depicted in SEQ ID NO:1, it may exhibit single or multiple substitutions with regard to SEQ ID NO: 1, wherein the substituted residues are selected from the following amino acid residues of SEQ ID NO:1: F19, W22, W36, F42, Y44, L55, L56, F67, L74, Y78, W107, Y115, I116, Y119, W123, W128, W137, W139, W154, E163, R167, E179, E189, Y200, Y275, Y276, C282, F300 and C303, in particular, the replacements of amino acids residues F, W, Y, I, L are exchanged for amino acids residues R, D, E, N, K, Q, H, S, T, M, G or A. With regard to the sequence of SEQ ID NO:1, one or more substitutions selected from the group comprising: W22R, F42A, F44A F67T, Y115S, W123M, W137A, W139A, W154H, E163A, E179Q, E179A, E187Q, Y200A, Y200H, Y275A, Y275M, Y276A, C282A, F300A, C303S, W310A and W310M, and further one of the following substitutions: F67T+Y115S, F67T+W137A, F67T+W139A, F67T+W154H, Y115S+W137A, Y115S+W139A, E163Q+R169A, E163A+R169A, E163Q+R167A+E189Q, E163A+R167A+E189Q, E163Q+R167A+E179Q+E189Q, E163Q+R167A+E189Q, E163A+R167A+E179Q+E189Q, E163A+R167A+E179A+E189Q, Y200A+Y275A, Y200A+Y276A, Y200A+C282A, Y200A+F300A, Y275A+Y276A, L55H+L56T+E163A+R167A+Y200H, E163A+R167A+E179A+E189Q+Y200H, L55H+L56T+E163A+R167A+E179A+E189Q+Y200H, S237L+R354Q+A367V, and L55H+L56T+E163A+R167A+Y200H+S237L+R354Q+A367V.

The polypeptide may lyse *S. aureus, S. aureus* (MRSA), *S. epidermidis, S. haemolyticus, S. simulans, S. saprophyticus, S. chromogenes, S. hyicus, S. warneri* and/or *S. xylosus*. The polypeptide may comprise biotin or Streptavidin as additional marker moiety. The polypeptide may further comprise a HA-tag, His-tag, Strep-tag, Myc-tag or GST-tag, such a is denoted in SEQ ID NO: 9 or SEQ ID NO: 13.

In another particular embodiment, the present invention provides a polypeptide comprising the sequence as depicted in SEQ ID NO:15, 18, 20 or 22 or variant thereof.

In still another particular embodiment, there is provided a nucleic acid molecule comprising a sequence encoding a polypeptide comprising the sequence as depicted in SEQ ID NO:1 or variant thereof, said variant being:
 a) a polypeptide comprising a sequence in which the CBD of SEQ ID NO:1 has been replaced by a CBD domain of another *Staphlococci* specific endolysin; or b) a polypeptide comprising the sequence of SEQ ID NO:1 except for at least the first N-terminal amino acid and at most the first 28 N-terminal amino acids of SEQ ID NO:1; or
c) a polypeptide comprising one or more point mutations or amino acid substitutions in the sequence of SEQ ID NO:1; or
d) a polypeptide comprising in addition to the sequence of SEQ ID NO: 1 sequences representing marker moieties, tags or other functional polypeptide sequences; or
e) a polypeptide comprising one or more additional amino acid residues inserted into the amino acid sequence according to SEQ ID NO:1; or
f) a polypeptide comprising a polypeptide sequence representing any combination of variants a), b), c), d) and e).

The nucleic acid molecule may comprise a sequence selected from SEQ ID NOs: 2, 4, 6, 8, 10, 12, 14, 16, 17, 19, 21, or 23. Also provided are a vector comprising these nucleic acids, a host cell comprising these nucleic acids, and a host cell comprising these vectors.

In still yet another embodiment, there is provided a pharmaceutical composition comprising, dispersed in a pharmaceutical buffer, diluent or medium, a polypeptide comprising the sequence as depicted in SEQ ID NO:1 or variant thereof, said variant being:
a) a polypeptide comprising a sequence in which the CBD of SEQ ID NO:1 has been replaced by a CBD domain of another *Staphlococci* specific endolysin; or
b) a polypeptide comprising the sequence of SEQ ID NO:1 except for at least the first N-terminal amino acid and at most the first 28 N-terminal amino acids of SEQ ID NO:1; or
c) a polypeptide comprising one or more point mutations or amino acid substitutions in the sequence of SEQ ID NO:1; or
d) a polypeptide comprising in addition to the sequence of SEQ ID NO: 1 sequences representing marker moieties, tags or other functional polypeptide sequences; or
e) a polypeptide comprising one or more additional amino acid residues inserted into the amino acid sequence according to SEQ ID NO:1; or
f) a polypeptide comprising a polypeptide sequence representing any combination of variants a), b), c), d) and e).

In a further embodiment, there is provided a method of treating or preventing a *Staphylococcus* infection comprising administering to a subject a composition comprising a polypeptide comprising the sequence as depicted in SEQ ID NO:1 or variant thereof, said variant being:
a) a polypeptide comprising a sequence in which the CBD of SEQ ID NO:1 has been replaced by a CBD domain of another *Staphlococci* specific endolysin; or
b) a polypeptide comprising the sequence of SEQ ID NO:1 except for at least the first N-terminal amino acid and at most the first 28 N-terminal amino acids of SEQ ID NO:1; or
c) a polypeptide comprising one or more point mutations or amino acid substitutions in the sequence of SEQ ID NO:1; or
d) a polypeptide comprising in addition to the sequence of SEQ ID NO: 1 sequences representing marker moieties, tags or other functional polypeptide sequences; or
e) a polypeptide comprising one or more additional amino acid residues inserted into the amino acid sequence according to SEQ ID NO:1; or
f) a polypeptide comprising a polypeptide sequence representing any combination of variants a), b), c), d) and e).

The *Staphylococcus* infection may result from infection by *S. aureus*, *S. aureus* (MRSA), *S. epidermidis*, *S. haemolyticus*, *S. simulans*, *S. saprophyticus*, *S. chromogenes*, *S. hyicus*, *S. warneri* and/or *S. xylosus*, which in turn may result in a disease state, such as bacteremia, endocarditis, keratitis, endoplastitis or bovine mastitis. The composition may be administered topically, orally or by IV injection.

In still a further embodiment, there is provided a method of sanitizing a surface comprising contacting said surface with a polypeptide comprising the sequence as depicted in SEQ ID NO:1 or variant thereof, said variant being:
a) a polypeptide comprising a sequence in which the CBD of SEQ ID NO:1 has been replaced by a CBD domain of another *Staphlococci* specific endolysin; or
b) a polypeptide comprising the sequence of SEQ ID NO:1 except for at least the first N-terminal amino acid and at most the first 28 N-terminal amino acids of SEQ ID NO:1; or
c) a polypeptide comprising one or more point mutations or amino acid substitutions in the sequence of SEQ ID NO:1; or
d) a polypeptide comprising in addition to the sequence of SEQ ID NO: 1 sequences representing marker moieties, tags or other functional polypeptide sequences; or
e) a polypeptide comprising one or more additional amino acid residues inserted into the amino acid sequence according to SEQ ID NO:1; or
f) a polypeptide comprising a polypeptide sequence representing any combination of variants a), b), c), d) and e).

The surface may be a food processing device. Contacting may comprise contacting said surface with the peptide or variant, or a host cell comprising a nucleic acid encoding said polypeptide or variant.

In yet a further embodiment, there is provided a cosmeceutical composition comprising a cosmetic diluent, carrier or excipient and a polypeptide comprising the sequence as depicted in SEQ ID NO:1 or variant thereof, said variant being:
a) a polypeptide comprising a sequence in which the CBD of SEQ ID NO:1 has been replaced by a CBD domain of another *Staphlococci* specific endolysin; or
b) a polypeptide comprising the sequence of SEQ ID NO:1 except for at least the first N-terminal amino acid and at most the first 28 N-terminal amino acids of SEQ ID NO:1; or
c) a polypeptide comprising one or more point mutations or amino acid substitutions in the sequence of SEQ ID NO:1; or
d) a polypeptide comprising in addition to the sequence of SEQ ID NO:1 sequences representing marker moieties, tags or other functional polypeptide sequences; or
e) a polypeptide comprising one or more additional amino acid residues inserted into the amino acid sequence according to SEQ ID NO:1; or
f) a polypeptide comprising a polypeptide sequence representing any combination of variants a), b), c), d) and e).

The cosmeceutical composition may alternatively comprise a cosmetic diluent, carrier or excipient and a host cell comprising a nucleic acid encoding the same.

Another embodiment comprises a method of treating or preventing a *Staphylococcus* infection comprising administering to a subject a composition comprising a nucleic acid encoding a polypeptide comprising the sequence as depicted in SEQ ID NO:1 or variant thereof, said variant being:
a) a polypeptide comprising a sequence in which the CBD of SEQ ID NO:1 has been replaced by a CBD domain of another *Staphylococci* specific endolysin; or b) a polypeptide comprising the sequence of SEQ ID NO:1 except for at least the first N-terminal amino acid and at most the first 28 N-terminal amino acids of SEQ ID NO:1; or c) a polypeptide comprising one or more point mutations or amino acid substitutions in the sequence of SEQ ID NO:1; or d) a polypeptide comprising in addition to the sequence of SEQ ID NO: 1 sequences representing marker moieties, tags or other functional polypeptide sequences; or e) a polypeptide comprising one or more additional amino acid residues inserted into the amino acid sequence according to SEQ ID NO:1; or f) a polypeptide comprising a polypeptide sequence representing any combination of variants a), b), c), d) and e).

The *Staphylococcus* infection may result from infection by *S. aureus*, *S. aureus* (MRSA), *S. epidermidis*, *S. haemolyticus*, *S. simulans*, *S. saprophyticus*, *S. chromogenes*, *S. hyicus*, *S. warneri* and/or *S. xylosus*, which in turn may result in a disease state, such as bacteremia, endocarditis, keratitis, endoplastitis or bovine mastitis. The composition may be administered topically, orally or by IV injection.

Yet another embodiment comprises a method of preventing or treating staphylococcal contamination of foodstuff, of food processing equipment, of food processing plants, or of surfaces coming into contact with foodstuff comprising contacting foodstuff, food processing equipment, food processing plants, or surfaces coming into contact with foodstuff with a polypeptide comprising the sequence as depicted in SEQ ID NO:1 or variant thereof, said variant being:

a) a polypeptide comprising a sequence in which the CBD of SEQ ID NO:1 has been replaced by a CBD domain of another *Staphlococci* specific endolysin; or b) a polypeptide comprising the sequence of SEQ ID NO:1 except for at least the first N-terminal amino acid and at most the first 28 N-terminal amino acids of SEQ ID NO:1; or c) a polypeptide comprising one or more point mutations or amino acid substitutions in the sequence of SEQ ID NO:1; or d) a polypeptide comprising in addition to the sequence of SEQ ID NO: 1 sequences representing marker moieties, tags or other functional polypeptide sequences; or e) a polypeptide comprising one or more additional amino acid residues inserted into the amino acid sequence according to SEQ ID NO:1; or f) a polypeptide comprising a polypeptide sequence representing any combination of variants a), b), c), d) and e).

Contacting may comprise contacting said foodstuff, food processing equipment, food processing plants, or surfaces with the polypeptide or variant, or host cell comprising a nucleic acid encoding said polypeptide or variant.

Still yet another embodiment comprises a method for diagnosing staphylococcal contamination of medicine, food, feedstock or an environment comprising contacting a medicine, food, feedstock or environmental sample with a polypeptide comprising the sequence as depicted in SEQ ID NO:1 or variant thereof, said variant being:

a) a polypeptide comprising a sequence in which the CBD of SEQ ID NO:1 has been replaced by a CBD domain of another *Staphlococci* specific endolysin; or b) a polypeptide comprising the sequence of SEQ ID NO:1 except for at least the first N-terminal amino acid and at most the first 28 N-terminal amino acids of SEQ ID NO:1; or c) a polypeptide comprising one or more point mutations or amino acid substitutions in the sequence of SEQ ID NO:1; or d) a polypeptide comprising in addition to the sequence of SEQ ID NO: 1 sequences representing marker moieties, tags or other functional polypeptide sequences; or e) a polypeptide comprising one or more additional amino acid residues inserted into the amino acid sequence according to SEQ ID NO:1; or f) a polypeptide comprising a polypeptide sequence representing any combination of variants a), b), c), d) and e).

Also provided is a diagnostic kit comprising a polypeptide comprising the sequence as depicted in SEQ ID NO:1 or variant thereof, said variant being:

a) a polypeptide comprising a sequence in which the CBD of SEQ ID NO:1 has been replaced by a CBD domain of another *Staphlococci* specific endolysin; or b) a polypeptide comprising the sequence of SEQ ID NO:1 except for at least the first N-terminal amino acid and at most the first 28 N-terminal amino acids of SEQ ID NO:1; or c) a polypeptide comprising one or more point mutations or amino acid substitutions in the sequence of SEQ ID NO:1; or d) a polypeptide comprising in addition to the sequence of SEQ ID NO: 1 sequences representing marker moieties, tags or other functional polypeptide sequences; or e) a polypeptide comprising one or more additional amino acid residues inserted into the amino acid sequence according to SEQ ID NO:1; or f) a polypeptide comprising a polypeptide sequence representing any combination of variants a), b), c), d) and e).

Other objects, features and advantages of the present invention will become apparent from the following detailed description. It should be understood, however, that the detailed description and the specific examples, while indicating particular embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

A. Definitions

Figure 1:
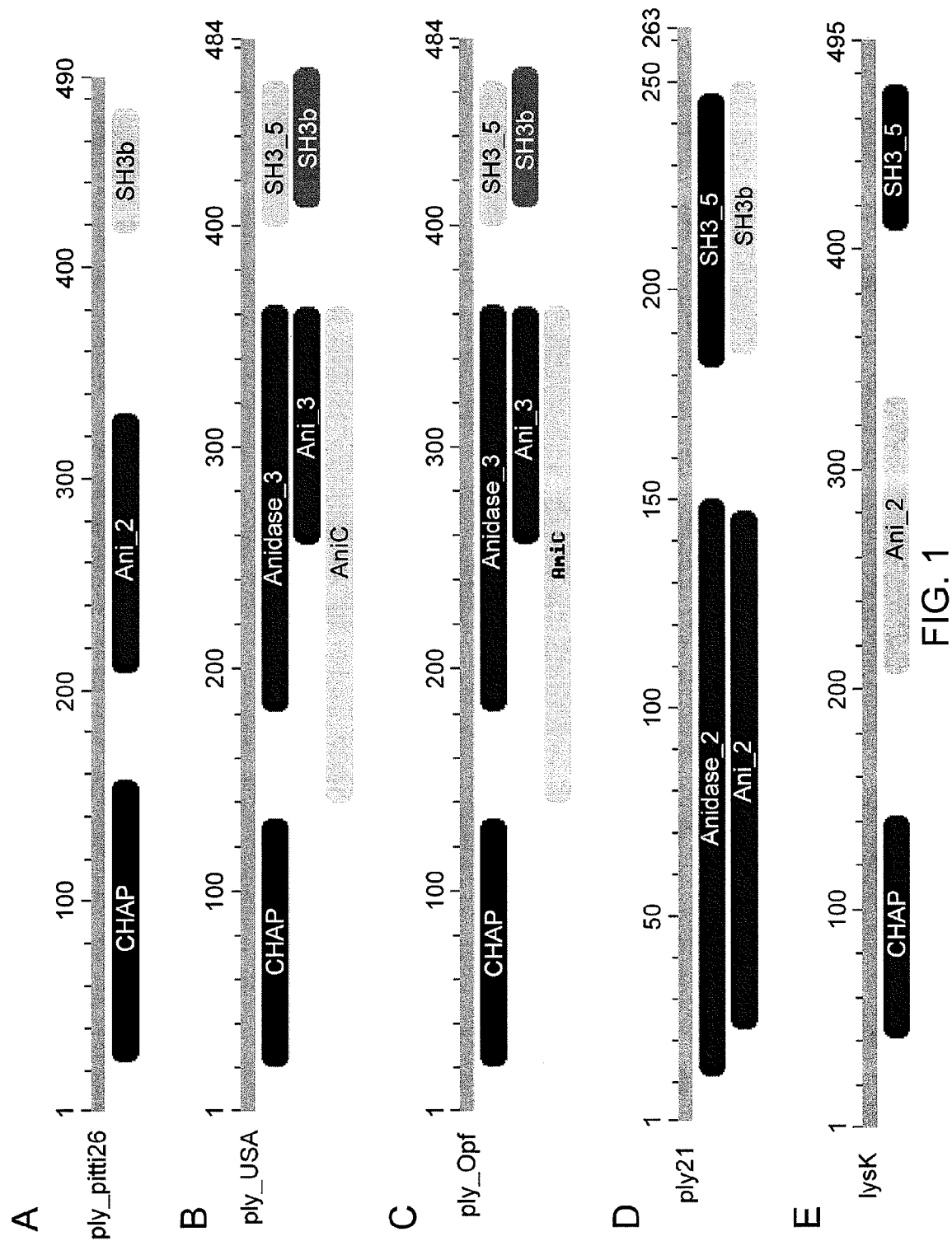
FIG. 1—A schematic representation of the modular organization of different *Staphylococcus* endolysins. The endolysins are built up from CHAP (cysteine, histidine-dependent amidohydrolases/peptidases), and amidase (N-acetyl-muramyl-L-alanine amidase, ami) enzymatic domains, and SH3-modules as cell binding domains (CBDs).

The term "endolysin" or "peptidoglycan hydrolase" as used herein refers to an enzyme which is suitable to hydrolyse bacterial cell walls. The enzyme comprises at least one of the following activities of which the "enzymatically-active domains" (EADs) of the endolysins are constituted: endopeptidase, carboxypeptidase, N-acetyl-muramoyl-L-alanine-amidase (amidase), N-acetyl-muramidase (lysozyme or lytic transglycosylase) or N-acetyl-glucosaminidase. Either, the enzyme is phage or prophage encoded or it is derived from related enzymes coded by bacteria, the so-called "autolysins." In addition, the endolysins usually contain also regions which are enzymatically-inactive, and bind to the cell wall of the host bacteria, the so-called CBDs (cell wall binding domains). The term endolysin refers also to lysostaphin and ALE-1 which contain an endopeptidase domain and a CBD.

The term "module" as used herein refers to a subunit of an endolysin which is ascribed a specific function. Generally, a module is a relatively small functional unit like CHAP-, ami- or SH3-modules.

The term "domain" as used herein refers to a subunit of an endolysin which is ascribed a specific function and can also coincide with structural domains. The term domain is used to describe the antagonism between EAD which can be composed of more than one module and CBD domains.

The term "CBD" as used herein refers to the cell wall binding domain or cell wall targeting domain of an endolysin, which is often found at the C-terminus of the protein. CBD domains have no enzymatic activity in terms of hydrolyzing the cell wall, but often mediate binding of the endolysin to the bacterial cell wall. CBD may contain an SH3 domain.

The term "EAD" as used herein refers to the enzymatically active domain of an endolysin which is responsible for hydrolysis of the bacterial peptidoglycan. It contains at least one of the enzymatic activities of an endolysin. The EAD can also be composed of more than one enzymatically-active module.

A "CHAP" domain (cysteine, histidine-dependent amidohydrolases/peptidases) is a region between 110 and 140 amino acids that is found in proteins from bacteria, bacteriophages, archaea and eukaryotes of the Trypanosomidae family. The proteins may function mainly in peptidoglycan hydrolysis. The CHAP domain is commonly associated with bacterial type SH3 domains and with several families of amidase domains. CHAP domain containing proteins may utilize a catalytic cysteine residue in a nucleophilic-attack mechanism. The CHAP domain contains two invariant amino acid residues, a cysteine and a histidine. These residues form part of the putative active site of CHAP domain containing proteins.

The term "ami" as used herein describes an enzymatically defined module which exhibits amidase activity, i.e., it hydrolyzes the amide bond between N-acetylmuramine in the peptidoglycan backbone and the adjacent amino acid which is usually L-ala in the peptide linker. The amidase are often metal ion dependent for activity.

The term "peptidase_M23" as used herein refers to a zinc-dependent metallopeptidase domain which cleaves glycyl-glycyl peptide bonds as an endopeptidase. Peptidase_M23 domains are found for example in lysostaphin and ALE-1.

The term "SH3" domain which is sometimes also called Src homology 3 domain as used herein describes a small non-catalytic protein domain of about 60 amino acids which is characteristic for proteins which interact with other binding partners. It is identified via a proline-rich consensus motif. The SH3 domain is usually located within the CBD. SH3 domains found in peptidoglycan hydrolases are often of the SH3b or SH3_5 type.

The term "shuffling" as used herein refers to the combination of different fragments of polypeptides from different enzymes into new chimeric polypeptide constructs. In this context, the enzymes may be endolysins, and the fragments may be modules. Usually, the fragments are combined by molecular biological methods on nucleic acid level. Small linker sequences may be introduced between the fragments for structural or cloning reasons.

The term "wild-type" as used herein refers to a naturally-occurring amino acid sequence of a protein or polypeptide or to a nucleotide sequence of a nucleic acid molecule encoding the protein or polypeptide.

The term "variant" as used herein refers to a modified form of a naturally occurring protein. Variants are generated by shuffling of polypeptides or mutations of polypeptides or addition of a tag or a marker or a combination of the different possibilities. Suitable mutations to generate a variant are deletions of amino acids, additions of amino acids or substitutions (amino acid exchanges, point mutations). The number of amino acids to be deleted, added or exchanged varies from 1 to several hundred. The respective modifications of the nucleic acids coding for the protein variants are determined by the genetic code.

B. Bacteriophage and Lysins

The inventors isolated several lytic bacteriophages from sewage samples which were active against *Staphylococci* using standard techniques for bacteriophage isolation (Adams, 1959). Several lysogenic phages were identified using molecular biological techniques within *Staphylococcus aureus* strains isolated from epidemic strains.

One isolated phage was named pitti26. Within the phage genomes of the isolated lysogenic phages endolysin proteins were identified and isolated. One particular endolysin was isolated from the lytic phage pitti26 and was named ply_pitti26 (SEQ ID NO:1). A further endolysin was identified within the lytic phage pitti20 and named ply_pitti20. A prophage derived endolysin, plyUSA, was identified in the genome of the prophage ΦSA2usa which was integrated into the genome of the methicillin-resistant *Staphylococcus aureus* strain USA300 (Diep et al., 2006; databank entry NC_007793).

Endolysins of bacteriophages specific to *Staphylococcus* bacteria are typically composed of two enzymatically active domains, namely a CHAP domain, and an amidase domain (ami), and a cell binding domain (CBD) which often is defined as an SH3-domain of the SH3b or SH3_5 type.

Lysostaphin and ALE-1, a homologue of lysostaphin, are peptidoglycan hydrolases that specifically lyse *Staphylococcus aureus* cell walls as both proteins comprise an endopeptidase domain (peptidase_M23) which cleaves the pentaglycine linkages between peptidoglycan chains, and a C-terminal SH3b domain which functions as a CBD or targeting domain. Lysostaphin is secreted by *Staphylococcus simulans* biovar *staphylolyticus*, and ALE-1 by *Staphylococcus capitis* EPK1. Lysostaphin is produced as a precursor protein which upon maturation loses tandem repeats at the N-terminus. ALE-1 comprises an N-terminal repeat domain which is not processed post-translationally. The cell wall targeting domain of ALE-1 was determined to consist of the 92 C-terminal amino acids (residues 271 to 362) (Lu et al., 2006). This domain is very similar to the C-terminal SH3b domain of lysostaphin (82% identity).

The inventors of the present invention combined the CHAP and the amidase domain of the endolysin plypitti26 with the cell binding domain of the prophage endolysin plyUSA, with the cell binding domain of the endolysin plypitti20, the cell wall targeting domain of lysostaphin, and the cell wall targeting domain of ALE-1 to generate chimeric endolysins having new properties for use of the endolysin variants as a therapeutic or prophylactic agent against staphylococcal infections, as an antimicrobial agent for disinfection or sanitation against *Staphylococcus* or as a means in *Staphylococcus* diagnostics. New properties are, e.g., a higher activity of the chimeric endolysins in buffer systems, in therapeutically relevant solutions like blood or serum, an increased host range of recognition within the genus *Staphylococcus* or the species *Staphylococcus aureus*, including the MRSA strains, a higher solubility of the chimeric endolysins including after expression, and a higher protein stability including thermostability, long-term stability or stability against proteases. The isolated endolysin plypitti26, as well as the chimeric enzymes, can be used to lyse bacteria of the genus *Staphylococcus*.

C. Lysin Polypeptides and Variants Thereof

In one aspect the present invention relates to a polypeptide termed ply_pitti26 comprising the sequence as depicted in SEQ ID NO: 1.

In a further aspect the present invention relates to variants of this polypeptide termed ply_pitti26 comprising the sequence as depicted in SEQ ID NO:1. The following embodiments are considered to be variants of ply_pitti26:

a) polypeptides comprising a sequence in which the CBD of ply_pitti26 has been replaced by a CBD domain of another *Staphlococci* specific endolysin or lysostaphin or ALE-1, b) polypeptides comprising the sequence of ply_pitti26 except for at least the first N-terminal and at most the first 28 N-terminal amino acids of ply_pitti26, c) polypeptides comprising one or more point mutations or substitutions in the sequence of ply_pitti26, d) polypeptides comprising in addition to SEQ ID NO: 1 marker moieties, tags or other functional polypeptide sequences, and e) polypeptides comprising one or more additional amino acid residues inserted into the amino acid sequence according to SEQ ID NO:1 f) any combinations of a), b), c), d) and e).

As mentioned above, the present invention relates to a polypeptide comprising the sequence of SEQ ID NO: 1 as well as variants thereof. The polypeptide as well as variants thereof are considered to be the polypeptides according to the present invention. All of them share the common feature to function as an endolysin capable to lyse *Staphylococcus* bacteria. The specificity for *Staphylococci* can be tested by a plurality of methods which are known in the art or described as set forth below, e.g., by adding the recombinant endolysin variant to a sample comprising one or more of the *Staphylococcus* species and determining the change in turbidity after addition of the (recombinant) endolysin.

In a particular embodiment, the variant of ply_pitti26 is a polypeptide wherein the CBD domain of the ply_pitti26 has been replaced by the CBD of another endolysin. In principle, there is no restraint with regard to choosing other CBD domains from anti-staphylococcal endolysins as long as the resulting (recombinant) endolysin retains a specificity for *Staphylococcus* bacteria, in particular for *S. aureus, S. aureus* (MRSA), *S. epidermidis, S. haemolyticus, S. simulans, S. saprophyticus, S. chromogenes, S. hyicus, S. warneri* and/or *S. xylosus*. In a particularly embodiment, the recombinant endolysin comprises an endolysin cell binding domain of the SH3 type. Particularly, the CBD domains are selected from the endolysin CBD domains of ply_USA or ply_pitti20 or lysostaphin or ALE-1. As CBD of ply_USA in particular the sequence as denoted in SEQ ID NO: 3 is exemplified. As CBD of ply_pitti20 in particular the sequence as denoted in SEQ ID NO: 5 is exemplified. Examples for such recombinant endolysin variants of ply_pitti26 with exchanged CBD are given in SEQ ID NOs: 7 and 11.

In a further particular embodiment, the variant of ply_pitti26 comprises the sequence of ply_pitti 26 except for a certain number of N-terminal residues. The inventors of the present invention discovered, that if more than 28 N-terminal amino acid residues are removed from SEQ ID NO:1 then the endolysin activity is lost. Therefore, suitable variants of ply_pitti26 comprise in principle the sequence of SEQ ID NO:1 but lack 1, 2, 3, 4, 5, 6, 7, 8, 9, 10, 11, 12, 13, 14, 15, 16, 17, 18, 19, 20, 21, 22, 23, 24, 25, 26, 27 or 28 N-terminal amino acid residues of SEQ ID NO:1. Particularly identified are variants which lack 4, 9 or 28 of the N-terminal amino acid residues of ply_pitti26.

In a particular embodiment, the variants of the polypeptide termed ply_pitti26 exhibit single or multiple substitutions with regard to SEQ ID NO: 1. In particular, the sites to be substituted for other amino acid residues are F19, W22, W36, F42, Y44, L55, L56, F67, L74, Y78, W107, Y115, I116, Y119, W123, W128, W137, W139, W154, E163, R167, E179, E189, Y200, Y275, Y276, C282, F300, C303 and/or W310. All positions are indicated with regard to SEQ ID NO: 1.

In an even more particular embodiment, hydrophobic amino acid residues such as F, W, Y, I, and L, especially the ones supposed to lie on the surface of the protein are exchanged against less hydrophobic amino acids such as R, D, E, N, K, Q, H, S, T, M, G, A, wherein A is particularly identified. As hydrophobic proteins tend to aggregate the substitutions increase the solubility of the protein. The potential surface exposure of amino acid residues can be predicted from a high resolution structure of the protein or from a model, if the structure of homologous proteins or modules is known. Charged amino acids such as E, D and R, K are preferentially exchanged against uncharged amino acids (e.g., Q or A for E, N or A for D, A for R or K) as charged amino acids are often recognition sites for proteases. Cysteines are preferentially exchanged against A or S as cysteines tend to build disulfide bridges under oxidising conditions which is potentially deleterious for enzyme structure and function.

Particular variations in the sequence of SEQ ID NO: 1 selected from the following group of mutations. All substitutions are given with regard to the position in SEQ ID NO:1: W22R, F42A, Y44A L55H, L56T, F67T, Y115S, W123M, W137A, W139A, W154H, E163Q, E163A, R167A, E179Q, E179A, E187Q, E189Q, Y200A, Y200H, Y275A, Y275M, Y276A, C282A, F300A, C303S, W310A and/or W310M. Said substitutions may be single mutants of SEQ ID NO:1 or may be a combination of two or more of said substitutions. Particular multiple mutants of SEQ ID NO:1 are selected form the group comprising the following multiple mutants: L55H+L56T, F67T+Y115S, F67T+W137A, F67T+W139A, F67T+W154H, Y115S+W137A, Y15S+W139A, E163Q+R167A, E163A+R167A, E163Q+R169A, E163A+R169A, E163Q+R167A+E189Q, E163A+R167A+E189Q, E163Q+R167A+Y200H, E163A+R167A+Y200H, E163Q+R167A+E179Q+E189Q, E163Q+R167A+E179A+E189Q, E163A+R167A+E179Q+E189Q, E163A+R167A+E179A+E189Q, Y200A+Y275A, Y200A+Y276A, Y200A+C282A, Y200A+F300A, Y275A+Y276A, Y275A+F300A, C282A+F300A, Y200A+Y275A+Y276A, Y275A+Y276A+F300A, L55H+

L56T+E163Q+R167A+Y200H, L55H+L56T+E163A+R167A+Y200H, E163Q+R167A+E179A+E189Q+Y200H, E163A+R167A+E189Q+Y200H, L55H+L56T+E163Q+R167A+E179A+E189Q+Y200H, L55H+L56T+E163A+R167A+E179A+E189Q+Y200H, and S237L+R354Q+A367V, L55H+L56T+E163A+R167A+Y200H+S237L+R354Q+A367V and L55H+L56T+E163Q+R167A+Y200H+S237L+R354Q+A367V.

In a further particular embodiment, the variant of ply_pitti26 comprises additional marker moieties such as biotin or streptavidin or tags such as HA-tag (amino acid sequence EQKLISEEDL), His-tag (Nieba et al., 1997), Strep-tag (Voss & Skerra, 1997), Myc-tag (Evan et al., 1985), GST-tag (Peng et al., 1993), JS-tag (WO 2008/077397), cysteine tag (EP 1399551) or other tags known in the art. Particular other functional polypeptide sequences are, for example, protease cleavage sites. In some embodiments, the above-mentioned variants of ply_pitti26 may serve for facilitating the biotechnological production of ply_pitti26 or the variants.

In a further particular embodiment, the variant of ply_pitti26 comprises one or more additional amino acid residues. Particularly, the polypeptide according to the present invention comprises one, two, three or four additional amino acid residues, wherein the residues may be contiguous residues or they may be inserted into independent positions. Disclosed is the addition of one or two amino acid residues, preferably of one, as is the addition of one amino acid residue after position one of a sequence, preferably the addition of the single Ala residue. If one or more amino acid residues have been inserted into ply_pitti26, the position set forth above being particular positions for amino acid substitutions have to be adjusted to the number and position of inserted amino acid residues. Exemplary, if an amino acid residue is inserted in position two the position F19 will be F20, W22 will be W23 and so on. If more than one amino acid residue is inserted, the new positions have to be adjusted accordingly.

It should understood that the above illustrated variants of ply_pitti26 must not be considered as strictly separate embodiments but instead may be combined. For example, a variant of ply_pitti26 according to the present invention may comprise one or more of the variants selected from the group of a N-terminal truncation of SEQ ID NO:1, one or more substitutions as indicated above, the CBD domain of another endolysin, one or more amino acid additions as well as for example a His-tag with the proviso that such recombinant endolysin is still specific for *staphylococci*. The person skilled in the art will readily realize which of the variants is suitable for his purposes and can always test such variants for activity against *staphylococci* by routine methods in the art, for example by assaying the effect of lysis activity on the optical density of a *staphylococci* containing solution. Illustrative examples for such combinatorial variants are given in SEQ ID NO: 9 (ply_pitti26 with CBD of plyUSA and additional C-terminal His-tag) and SEQ ID NO: 13 (ply_pitti26 with CBD of ply_pitti20 and additional C-terminal His-tag).

An illustrative example of a ply_pitti26 variant having a replaced CBD and further one amino acid addition at position two is given in SEQ ID NO:28 (ply_pitti26 with CBD of plyUSA and additional amino acid residue A at position two) designated EADplypitti26_CBDplyUSA-Add2.

Further illustrative examples of ply_pitti26 variants having a replaced CBD, one or more amino acid substitutions and further an additional amino acid residue at position two are described below. Particularly identified is the polypeptide having an amino acid sequence according to SEQ ID NO:15. The polypeptide is derived from ply_pitti26 with the CDB of plyUSA as depicted in SEQ ID NO:7 having the following five single amino acid substitutions L56H, L57T, E164A, R168A and Y201H and one additional A2. The variant is named EADplypitti26_CBDplyUSA-Add2_M5. The annotation "_M5" stands for every construct comprising the particular combination of the five single amino acid substitutions L56H, L57T, E164A, R168A and Y201H within the EAD of ply_pitti26. The annotation "Add2" stands for every construct comprising the additional single amino acid residue at position two of the EAD of ply_pitti26. A further particular embodiment is a variant combining the EAD of ply_pitti26 with the CBD of lysostaphin named EADplypitti26_CBDLS-Add2_M5 and having the amino acid sequence as depicted in SEQ ID NO. 20 or the variant combining the EAD of ply_pitti26 with the CBD of ALE-1 lysin named EADplypitti26_CBDALE1-Add2_M5 and having the amino acid sequence as depicted in SEQ ID NO. 22.

Particularly disclosed is in addition the polypeptide having the amino acid sequence according to SEQ ID NO:18. The polypeptide is derived from ply_pitti26 with the CDB of plyUSA as depicted in SEQ ID NO:7 having the following eight single amino acid substitutions L56H, L57T, E164A, R168A, Y201H, S238L, R355Q, and A368V and one additional A2. The variant is named EADplypitti26_CBDplyUSA-Add2_M8.

In another aspect the present invention relates to a nucleic acid molecule encoding one of the polypeptides of the invention. It is apparent to a person skilled in the art that there may be many ways of constructing nucleic acid molecules encoding for one of the polypeptides according to the present invention, for example in view of the degenerate genetic code. A person skilled in the art with knowledge about the amino acid sequence of the polypeptide of the present invention is capable of choosing an adequate nucleotide sequence which suits his purposes most, for example in which the codon usage has been adapted to the codon usage of his desired expression host. A nucleic acid molecule comprising a sequence encoding for a polypeptide of the invention is considered to be the nucleic acid or nucleotide sequence, respectively, of the present invention.

In a particular embodiment, the nucleic acid molecule encodes for the endolysin comprising the sequence of SEQ ID NO: 1. Particularly, the nucleic acid comprises the nucleotide sequence as depicted in SEQ ID NO: 2.

In another particular embodiment, the polypeptide to be encoded is a variant of ply_pitti26, in particular a variant wherein the CBD domain is replaced by a CBD of another staphylococcal bacteriophage endolysin. Illustrative examples for nucleotide sequences encoding the CBD of plyUSA or ply_pitti20 or lysostaphin or ALE-1 are given in SEQ ID NOs: 4 and 6, and 25 and 27 respectively. Further examples illustrating nucleotide sequences of the present invention are given in SEQ ID NOs: 8 (encoding for ply_pitti26 with CBD of ply_USA), 10 (encoding for ply_pitti26 with CBD of ply_USA plus additional C-terminal His-tag), 12 (encoding for ply_pitti26 with CBD of ply_pitti20) and 14 (encoding for ply_pitti26 with CBD of ply_pitti20 plus additional C-terminal His-tag), respectively.

In a particular embodiment the nucleic acid molecule encodes for the polypeptide comprising the sequence of SEQ ID NO:15, namely, EADplypitti26_CBDplyUSA-Add2_M5. Particularly, the nucleotide comprises the nucleotide sequence as depicted in SEQ ID NO:16 and 17. SEQ ID NO:16 is the nucleotide sequence isolated from the phage pitti26 and prophage ΦSA2usa, respectively, with modifications of those nucleotide codons which encode the amino acid residues which have been substituted, i.e., L56H, L57T, E164A, R168A and Y201H and with an inserted codon encoding the additional amino acid residue A2. SEQ ID NO:17 is derived from SEQ ID NO:16 but has been codon optimized for expression in *E. coli* K12. Further particular embodiments are the nucleotide sequences SEQ ID NO:19 which is codon optimized also, SEQ ID NO:21, and SEQ ID NO:23, encoding for the polypeptides according to the invention EADplypitti26_CBDplyUSA-Add2_M8, EADplypitti26_CBDLS-Add2_M5, and EADplypitti26_CBDALE1-Add2_M5, respectively.

In a further aspect, the present invention relates to a vector comprising a nucleic acid sequence of the invention. Particularly, the vector provides for the expression of the polypeptide of the invention in a suitable host cell. The host cell may be selected due to mere biotechnological reasons, e.g., yield, solubility, costs, etc. but may be also selected from a medical point of view, e.g., a non-pathological bacteria or yeast, human cells, if the cells are to be administered to a subject. The vector may provide for the constitutive or inducible expression of the polypeptides according to the present invention.

In a further aspect of the present invention, the above-mentioned polypeptides and/or cells are employed in a method for the treatment or prophylaxis of *Staphylococcus* infections in a subject, in particular for the treatment or prophylaxis of infections by *S. aureus*, *S. aureus* (MRSA), *S. epidermidis*, *S. haemolyticus*, *S. simulans*, *S. saprophyticus*, *S. chromogenes*, *S. hyicus*, *S. warneri* and/or *S. xylosus*. The subject may be a human subject or an animal, in particular animals used in livestock farming and/or dairy farming such as cattle. The method of treatment encompasses the application of the polypeptide of the present invention to the site of infection or site to be prophylactically treated against infection in a sufficient amount.

In particular, said method of treatment may be for the treatment or prophylaxis of infections, in particular by *Staphylococcus aureus*, of the skin, of soft tissues, of bacteremia and/or endocarditis.

In a further particular embodiment, a polypeptide according to the present invention is employed in a method for the treatment of keratitis, in particular of keratitis caused by *S. haemolyticus*.

In a further preferred embodiment a polypeptide according to the present invention is used to treat or prevent endoplastitis, in particular endoplatitis caused by *S. epidermidis*.

In a further preferred embodiment a polypeptide according to the present invention is used to treat or prevent urinary tract infections, in particular endoplatitis caused by *S. saprophyticus*.

In a further particular embodiment, a polypeptide according to the present invention is used in a method of treatment (or prophylaxis) of staphylococcal infections in animals, in particular in livestock and dairy cattle. In particular, a polypeptide of the present application is suitable for use in methods of treatment (or prophylaxis) of bovine mastitis, in particular of bovine mastitis caused by *S. aureus*, *S. epidermidis*, *S. simulans*, *S. chromogenes*, *S. hyicus*, *S. warneri* and *S. xylosus*.

Furthermore, a polypeptide of the present invention may be used prophylactically as sanitizing agent, in particular before or after surgery, or for example during hemodialysis. Similarly, premature infants and immunocompromised persons, or those subjects with need for prosthetic devices can be treated with a polypeptide of the present invention, either prophylactically or during acute infection. In the same context, nosocomial infections by *Staphylococcus*, in particular by *S. aureus* or *S. aureus* (MRSA), may be treated prophylactically or during acute phase with a polypeptide of the present invention. In this embodiment, a polypeptide of the present invention may be used as a disinfectant also in combination with other ingredients useful in a disinfecting solution like detergents, tensids, solvents, antibiotics, lanthibiotics, or bacteriocins.

In a particular embodiment, a polypeptide of the present invention is used for medical treatment, if the infection to be treated (or prevented) is caused by multiresistant *Staphylococcus* strains, in particular by strains resistant against vancomycin, linezolid or daptomycin. Furthermore, a polypeptide of the present invention can be used in methods of treatment by administering them in combination with conventional antibacterial agents, such as antibiotics, lanthibiotics, bacteriocins other endolysins, etc.

The dosage and route of administration used in a method of treatment (or prophylaxis) according to the present invention depends on the specific disease/site of infection to be treated. The route of administration may be for example in particular embodiments oral, topical, nasopharyngeal, parenteral, intravenous, rectal or any other route of administration.

For application of a polypeptide of the present invention to a site of infection (or site endangered to be infected) a polypeptide of the present invention may be formulated in such manner that the endolysin is protected from environmental influences such as proteases, oxidation, immune response etc., until it reaches the site of infection.

Therefore, a polypeptide of the present invention may be formulated as capsule, dragee, pill, suppository, injectable solution or any other medical reasonable galenic formulation. In some embodiments these galenic formulation may comprise suitable carriers, stabilizers, flavourings, buffers or other suitable reagents.

For example, for topical application a polypeptide of the present invention may be administered by way of a lotion or plaster.

For nasopharyngeal application a polypeptide according to the present invention may be formulated in saline in order to be applied via a spray to the nose.

For treatment of the intestine, for example in bovine mastitis, suppository formulation can be envisioned. Alternatively, oral administration may be considered. In this case, the polypeptide of the present invention has to be protected from the harsh digestive environment until the site of infection is reached. This can be accomplished for example by using bacteria as carrier, which survive the initial steps of digestion in the stomach and which secret later on a polypeptide of the present invention into the intestinal environment.

All medical applications rely on the effect of the polypeptides of the present invention to lyse specifically and immediately staphylococcal bacteria when encountered. This has an immediate impact on the health status of the treated subject by providing a reduction in pathogenic bacteria and bacterial load and simultaneously relieves the immune system. Thus, the major task a person skilled in the art faces is to formulate the polypeptides of the present invention accurately for the respective disease to be treated. For this purpose usually the same galenic formulation as employed for conventional medicaments for these applications can be used.

In a further aspect of the present invention the above mentioned polypeptides and/or cells are a component of a pharmaceutical composition, which optionally comprises a carrier substance.

In an even further aspect the polypeptides and/or cells are part of a cosmetics composition. As mentioned above, several staphylococcal species can cause irritations on environmentally exposed surfaces of the patient's body such as the skin.

In order to prevent such irritations or in order to eliminate minor manifestations of the staphylococcal pathogens, special cosmetic preparations may be employed, which comprise sufficient amounts of polypeptides of the present invention in order to lyse already existing or freshly settling *Staphylococci*.

In a further aspect the present invention relates to the use of the polypeptides according to the present invention in foodstuff, on food processing equipment, in food processing plants, on surfaces coming into contact with foodstuff such as shelves and food deposit areas and in all other situations, where staphylococcal bacteria can potentially infest food material.

A further aspect of the present invention relates to the use of the polypeptides according to the present invention in diagnostics of *Staphylococcus*. In this aspect the polypeptides according to the invention are used as a means to specifically lyse *Staphylococcus* bacteria. The lysis of the bacterial cells by the polypeptides according to the present invention may be supported by the addition of detergents like Triton X-100 or other additives which weaken the bacterial cell envelope like polymyxin B. Specific cell lysis is needed as an initial step for subsequent specific detection of *Staphylococcus* bacteria using nucleic acid based methods like PCR, nucleic acid hybridization or NASBA (Nucleic Acid Sequence Based Amplification), immunological methods like IMS, immunfluorescence or ELISA techniques, or other methods relying on the cellular content of the bacterial cells like enzymatic assays using proteins specific for *Staphylococcus* bacteria.

A further aspect of the present invention relates to a diagnostic kit comprising the polypeptide according to the present invention, detergents like Triton X-100 or other additives which weaken the bacterial cell envelope like polymyxin B. The kit may contain furthermore means and substances for the detection like PCR means, means for nucleic acid hybridization or NASBA (Nucleic Acid Sequence Based Amplification), immunological methods like IMS, immunfluorescence or ELISA techniques, or other methods relying on the cellular content of the bacterial cells like enzymatic assays using proteins specific for *Staphylococcus* bacteria.

D. EXAMPLES

All cloning procedures were performed using standard techniques according to Sambrook et al. (1989). Mutations and deletions were also introduced using standard techniques.

Example 1

Cloning of the Endolysins According to the Invention

For EADplypitti26_CBDplyUSA, the nucleotide sequence of the CHAP-Ami2 domain was amplified from the lytic phage pitti26 (own isolate) and the CBD sequence was amplified from plyUSA. For EADplypitti26_CBDplypitti20, the CBD was derived from plypitti20 (own isolate). The fragments were combined by ligation, and cloned into the expression vector pET14b via the restriction sites NcoI and BamHI. In order to add a C-terminal His-tag to the sequence, the new construct was cloned into the expression vector pQE60 via the restriction sites NcoI and BamHI. This construct contains an additional sequence of Ser-Arg-Ser-(His6) at the C-terminus.

Example 2

Expression and Solubility Testing of the Endolysins According to the Invention

For expression of the cloned constructs E. coli HMS174 (DE3) (pET14b construct) and E. coli M15 (pQE construct) were used, respectively. Cells were grown in LB medium containing ampicillin and rifampicin (HMS174(DE3)) or ampicillin (M15) at 30° C. or 37° C. with shaking and induced with 1 mM IPTG at $OD_{600}$ nm 0.4-0.6 (mid log phase). After shaking for further 3-4 hours the cells were harvested by centrifugation and frozen at −20° C.

For solubility testing, harvested cells were resuspended in lysis buffer (20 mM Tris/HCl pH 8.0, 5 mM EDTA), sonicated (2×30 sec) and centrifuged. The pellet was solved in exactly the same volume of buffer as the supernatant. Identical sample volumes of pellet and supernatant fractions were analyzed with 12% SDS-PAGE.

Whereas upon expression at 37° C. the solubility of recombinantly produced endolysins was generally poor, the solubility of EADplypitti26_CBDplyUSA was significantly higher than that of wild-type plypitti26 at 30° C. Whereas almost all protein was found in the insoluble pellet fraction with plypitti26, a soluble fraction of around 30% to 40% was found upon expression of EADplypitti26_CBDplyUSA. This holds similar for EADplypitti26_CBDplypitti20.

Example 3

Purification of the Endolysins According to the Invention

For the purification of the soluble His-tagged versions of the endolysin constructs according to the invention a Ni-NTA-Sepharose column (Amersham) was used according to the manufacturer's instructions. The cell pellet was resuspended in equilibration buffer (25 mM Tris/HCl pH 8.0, 500 mM NaCl, 20 mM imidazole, 0.1% Tween 20, 10% glycerol), centrifuged and added to the column equilibrated with the same buffer. Elution of the protein was carried out in elution buffer (25 mM Tris/HCl pH 8.0, 500 mM imidazole, 0.1% Tween 20, 10% glycerol), and the eluted fractions were analyzed with SDS-PAGE. The combined fractions containing purified endolysins were dialyzed against storage buffer (20 mM Tris/HCl pH 7.5, 10 mM DTE, 0.1 mM $ZnSO_4$) and stored at −20° C.

The purification of the soluble version of the endolysins according to the invention without His-tag followed standard purification procedures with anion exchange chromatography, size exclusion chromatography and hydrophobic chromatography using for example Streamline HST, Superdex, and HiTrap Capto MMC columns (GE Healthcare).

The amount of active endolysin can be increased if insoluble endolysin material deposited in inclusion bodies (pellet fraction of Example 2) is solubilized under denaturing conditions and subsequently refolded. The amount of protein deposited in inclusion bodies can be increased by increasing expression temperature to 37° C., for example. Suitable conditions for solubilization and refolding are described for example in Navarre et al. (1999).

Example 4

Agar Plate Activity Assay

An overnight culture of a *staphylococcus* strain which was growing for about 18 hours at 37° C. in Brain Heart Infusion medium (Oxoid), was collected by centrifugation, the cell pellet was resuspended in 1×DPBS (Merck) thereby reducing the original volume by a factor of 100 and heat-inactivated at 80° C. for 20 minutes. The cells were sonicated and solved in LB topagar including ampicillin and IPTG (0.7% agar (Bacto); 100 µg/ml ampicillin (Sigma); 1 mM IPTG (Roth)), and used for the preparation of "lysis plates." These plates can be overlayed with protein solutions or solutions of *E. coli*-harboring plasmids which code for the desired proteins. A lysis zone on the plate is visible if the lytic protein is active respectively is expressed at least partly in soluble and active form.

The agar plate assay was used to test the lysis activity of EADplypitti26_CBDplyUSA in comparison with the wild-type form of pitti26 using different coagulase-positive (*Staphylococcus aureus*) and coagulase-negative (e.g., *S. epidermidis, S. haemolyticus, S. saprophyticus, S. simulans*) *Staphylococcus* strains. This was done in an agar plate lysis assay. Concentrated heat inactivated (e.g., 20 min at 80° C.) *Staphylococcus* cells are fixed in a top agar layer in a way that a dense bacterial lawn is achieved. Either isolated endolysin solution (5 µl to 10 µl) or *E. coli* transformants harboring the respective endolysin containing plasmids are stippled onto the surface of the top agar layer. The plates are incubated at 30° C. for several hours (1 h to 12 h), and then checked for lysis zones around the endolysin spots. Normally, an increase in the lysis zone diameter also coincides with a clearing of the lysis zone indicating more efficient cell lysis. The results are depicted in Table 1.

with diagnosed staphylococcal infection. DSMZ numbers represent strains that can be ordered from the "Deutsche Sammlung für Mikroorganismen und Zellkulturen" (Braunschweig) the remaining being own isolates from our laboratory. The lysis assay demonstrated that the activity of EADplypitti26_CBDplyUSA is often better than the activity of the wild-type enzyme plypitti26, especially on the coagulase-negative non-*S. aureus* strains. This means also that EADplypitti26_CBDplyUSA has a broader host range compared to plypitti26. Coagulase-negative *staphylococci* (species other than *Staphylococcus aureus*) are involved in infections in weakened and immune-compromised persons, cause problems in biofilm formation in persons wearing indwelling devices or other implants, and are involved in mastitis. *S. saprophyticus* causes special problems in urinary tract infections.

Example 5

Turbidity Assay to Control Lysis Activity

The second activity test we use for endolysin function is a turbidity test, where lysis of bacterial cells is measured "online" in a photometer. The absorption at 600 nm is a measure for the density of the cell culture and decreases upon cell lysis when the sample also becomes visibly clear. In contrast to the agar plate assay described above, this assay uses non-heat-treated bacterial cells, and is therefore more stringent and closer to reality in medical applications. Lysis of

TABLE 1

Host range for lysis by EADplypitti26_CBDplyUSA and plypitti26

| PROFOS culture collection Nr. | Origin | *Staphylococcus* species | plypitti26 | EADplypitti26_CBDplyUSA |
|---|---|---|---|---|
| S462 | Clinical isolate | *S. aureus* | +++ | +++ |
| S460 | Clinical isolate | *S. aureus* | ++ | +++ |
| S1516 | Clinical isolate | *S. aureus* | +++ | +++ |
| S459 | Clinical isolate | *S. aureus* | +++ | +++ |
| S457 | Clinical isolate | *S. aureus* | +++ | +++ |
| S456 | Clinical isolate | *S. aureus* | +++ | +++ |
| S1519 | Clinical isolate | *S. aureus* | +++ | +++ |
| S463 | Clinical isolate | *S. aureus* | +++ | +++ |
| S1551 | DSMZ346 | *S. aureus* | ++ | +++ |
| S1517 | Clinical isolate | *S. aureus* | +++ | +++ |
| S458 | Clinical isolate | *S. aureus* | +++ | +++ |
| S1550 | DSMZ20231 | *S. aureus* | ++ | ++ |
| S467 | Clinical isolate | *S. aureus*, MRSA | + | +++ |
| S469 | Clinical isolate | *S. aureus*, MRSA | +++ | +++ |
| S468 | Clinical isolate | *S. aureus*, MRSA | +++ | +++ |
| S1573 | Own isolate, patient | *S. epidermidis* | − | +++ |
| S1508 | Clinical isolate | *S. epidermidis* | +++ | +++ |
| S1510 | Clinical isolate | *S. epidermidis* | +++ | +++ |
| S1546 | DSMZ20044 | *S. epidermidis* | + | +++ |
| S27 | Own isolate | *S. haemolyticus* | + | +++ |
| S1548 | DSMZ20228 | *S. haemolyticus* | + | +++ |
| S1509 | Clinical isolate | *S. haemolyticus* | − | +++ |
| S1549 | DSMZ20263 | *S. haemolyticus* | + | +++ |
| S1429 | Own isolate, food | *S. saprophyticus* | − | +++ |
| S1512 | Clinical isolate | *S. simulans* | ++ | +++ |

Figure 2:
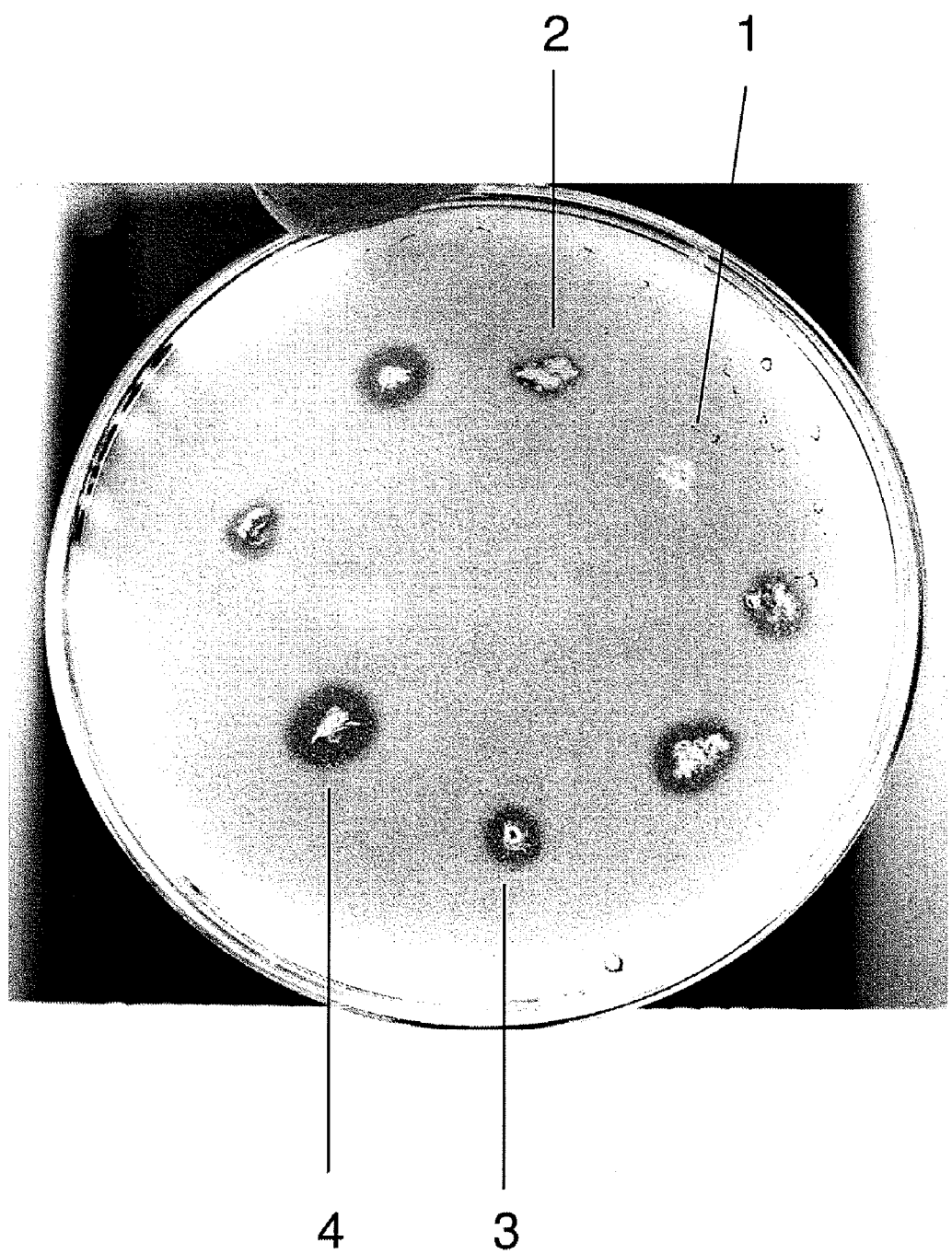
FIG. 2—Agar plate showing lysis zones in an activity test on heat inactivated *staphylococcus* cells. Lysis plates include the respective *staphylococcus* strain to be tested in a top agar layer. Either *E. coli* strains harbouring plasmids of the endolysin constructs to be tested or preparations of isolated endolysins are stippled to the top of the plates. Lysis zones appear after incubation depending on the lysing activity on the respective host bacterium. Number 1 depicts an example, where no lysis occurred (−). Numbers 2, 3, and 4 mark weak (+), medium (++) or strong (+++) lytic activity of the respective endolysin variant. The agar plate in the figure exemplarily shows an assay, where the activity of several point mutations in EADplypitti26_CBDplyUSA were tested.
Figure 3:
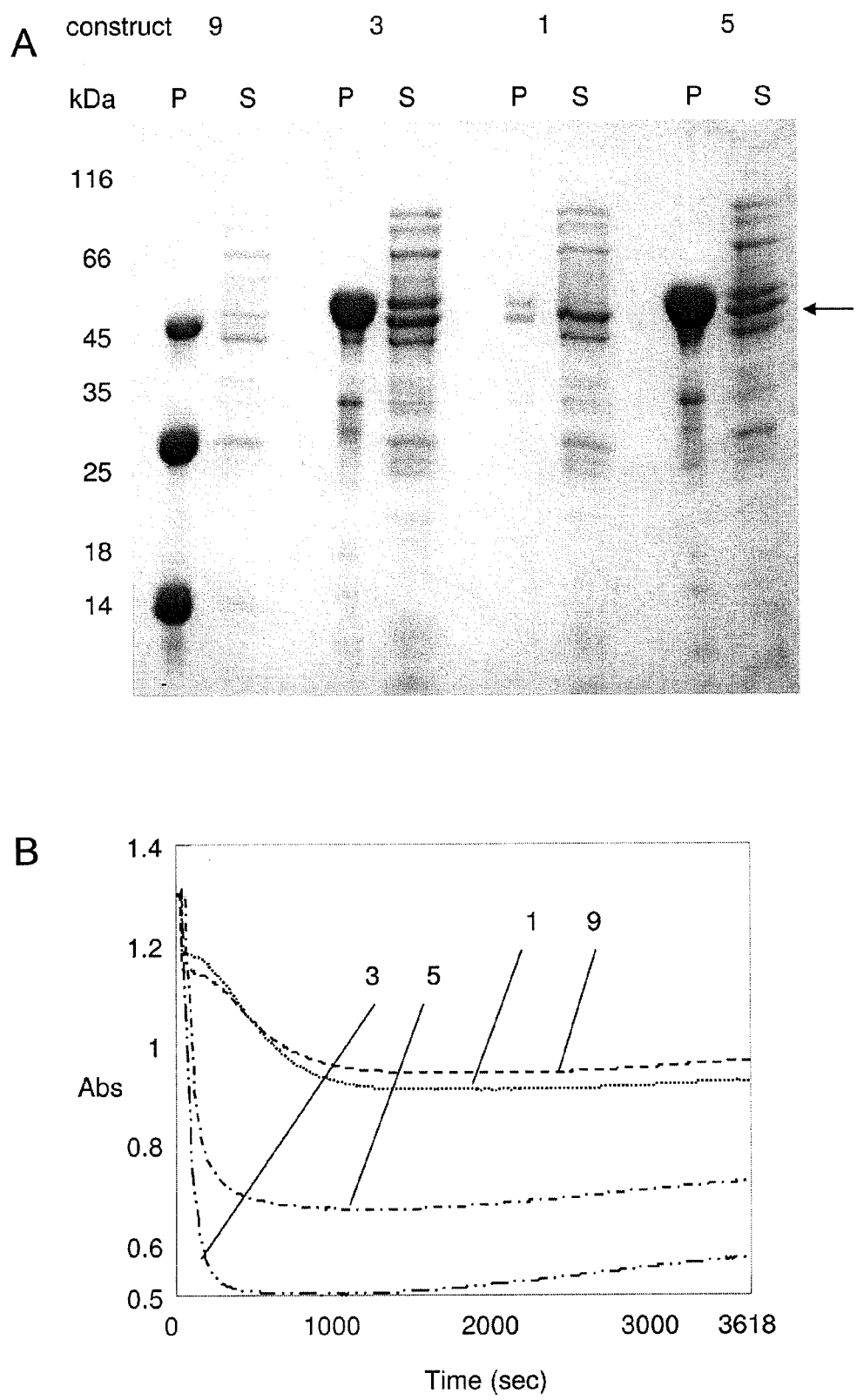
FIGS. 3A
Figure 4:
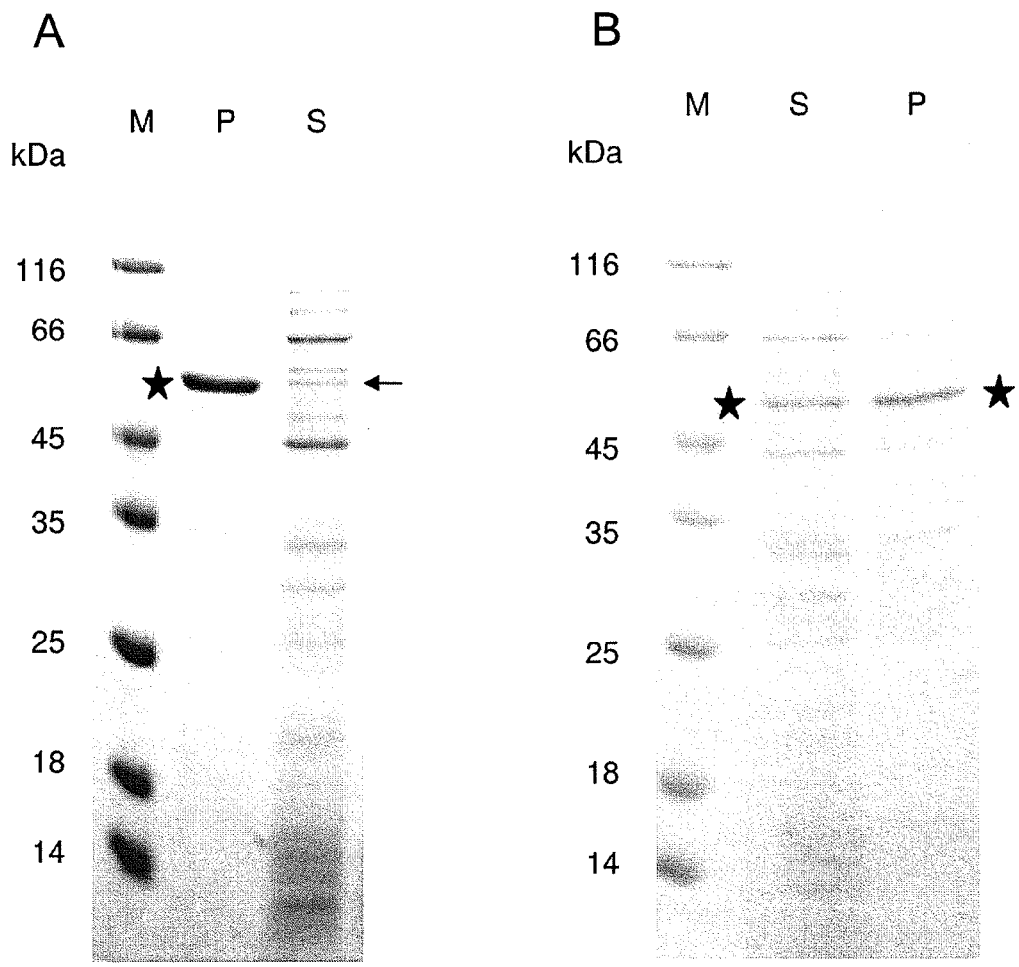
Figure 5:
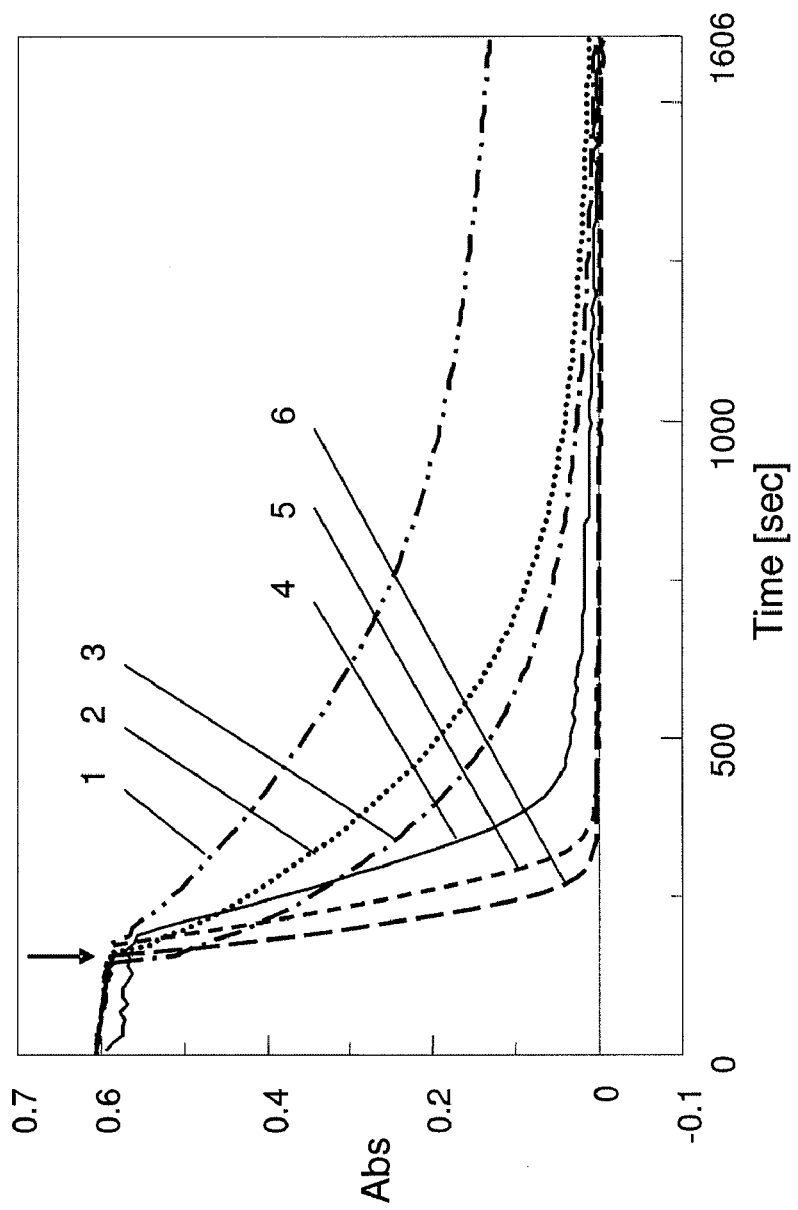
Figure 6:
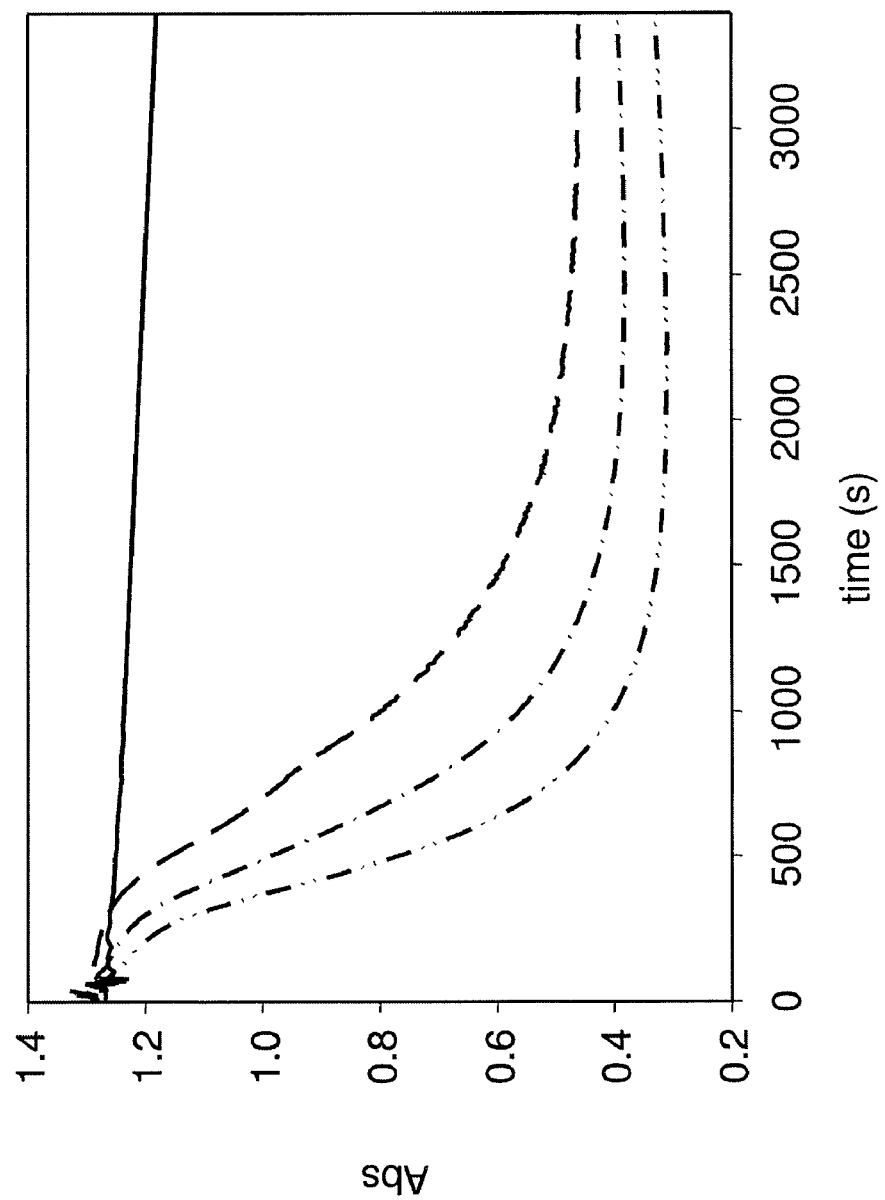
Figure 8:
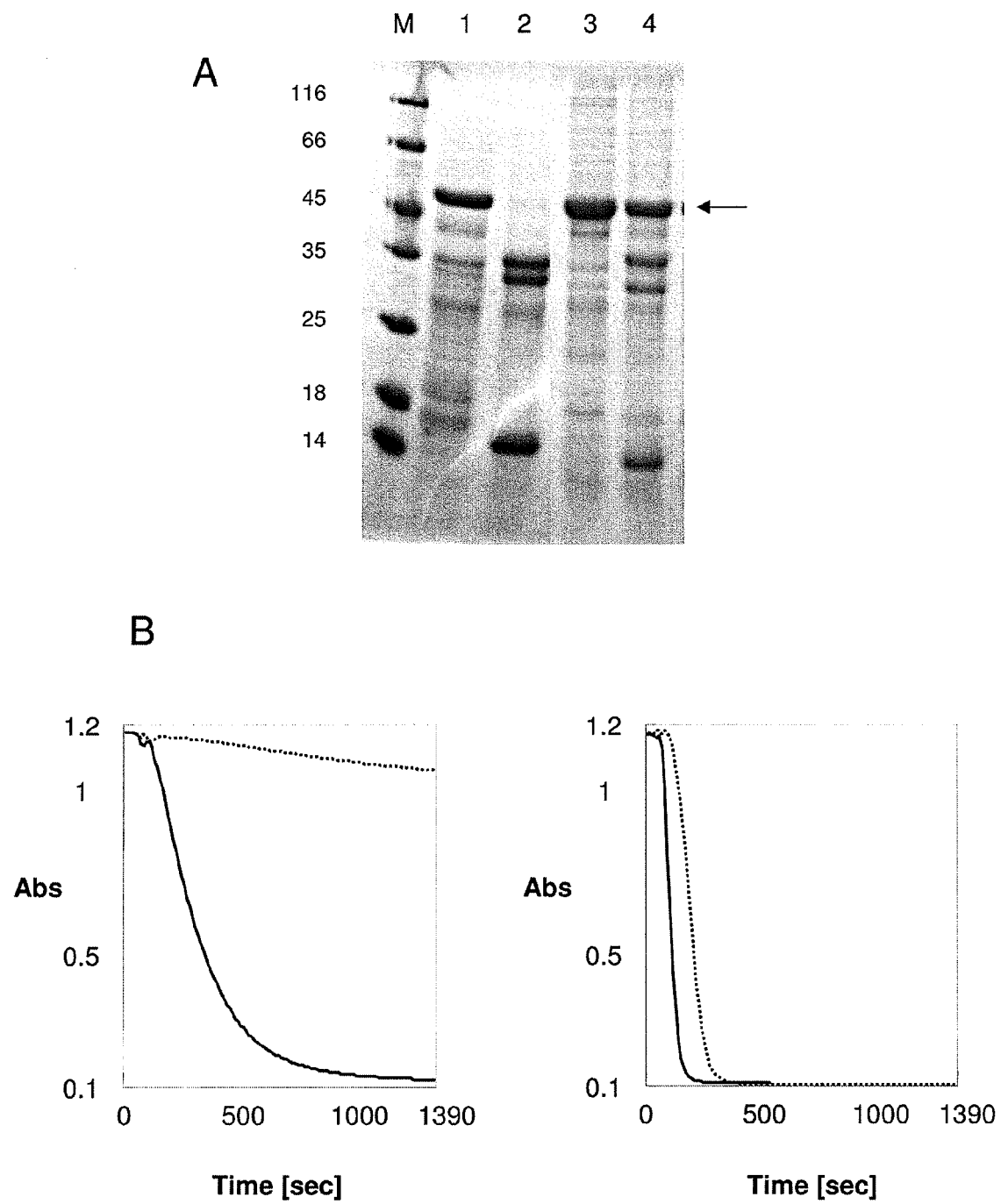
Figure 9:
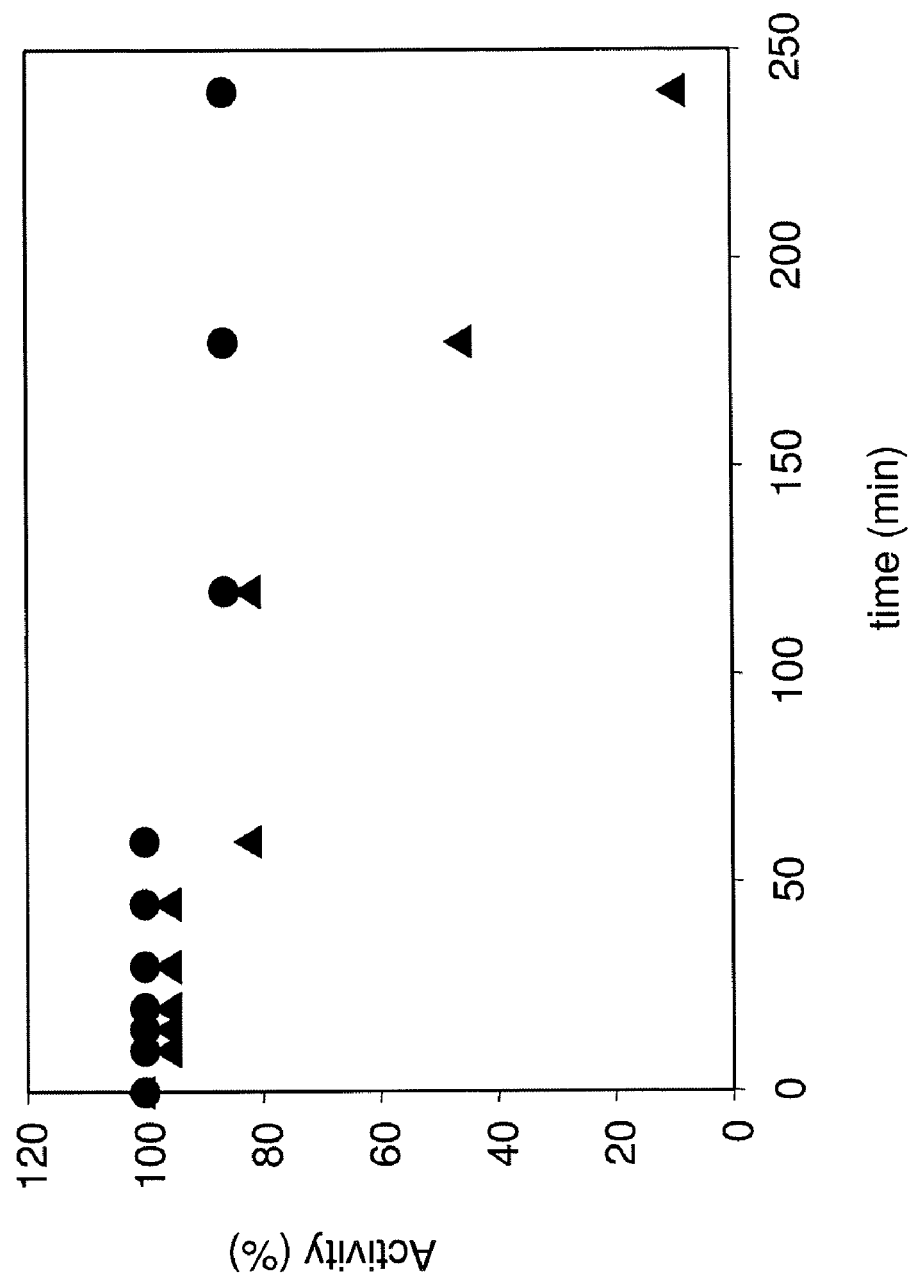
Figure 11:
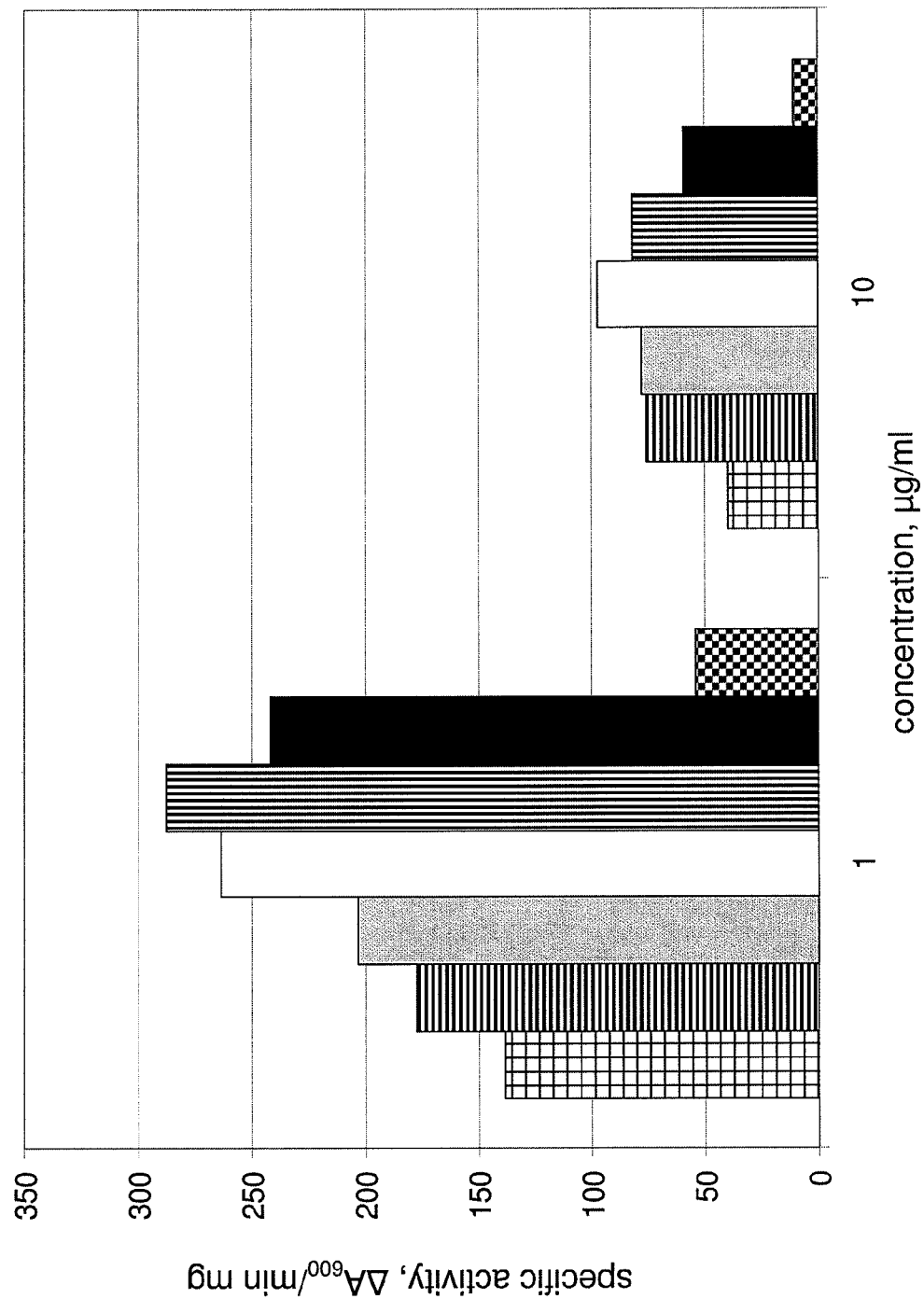
Figure 12:
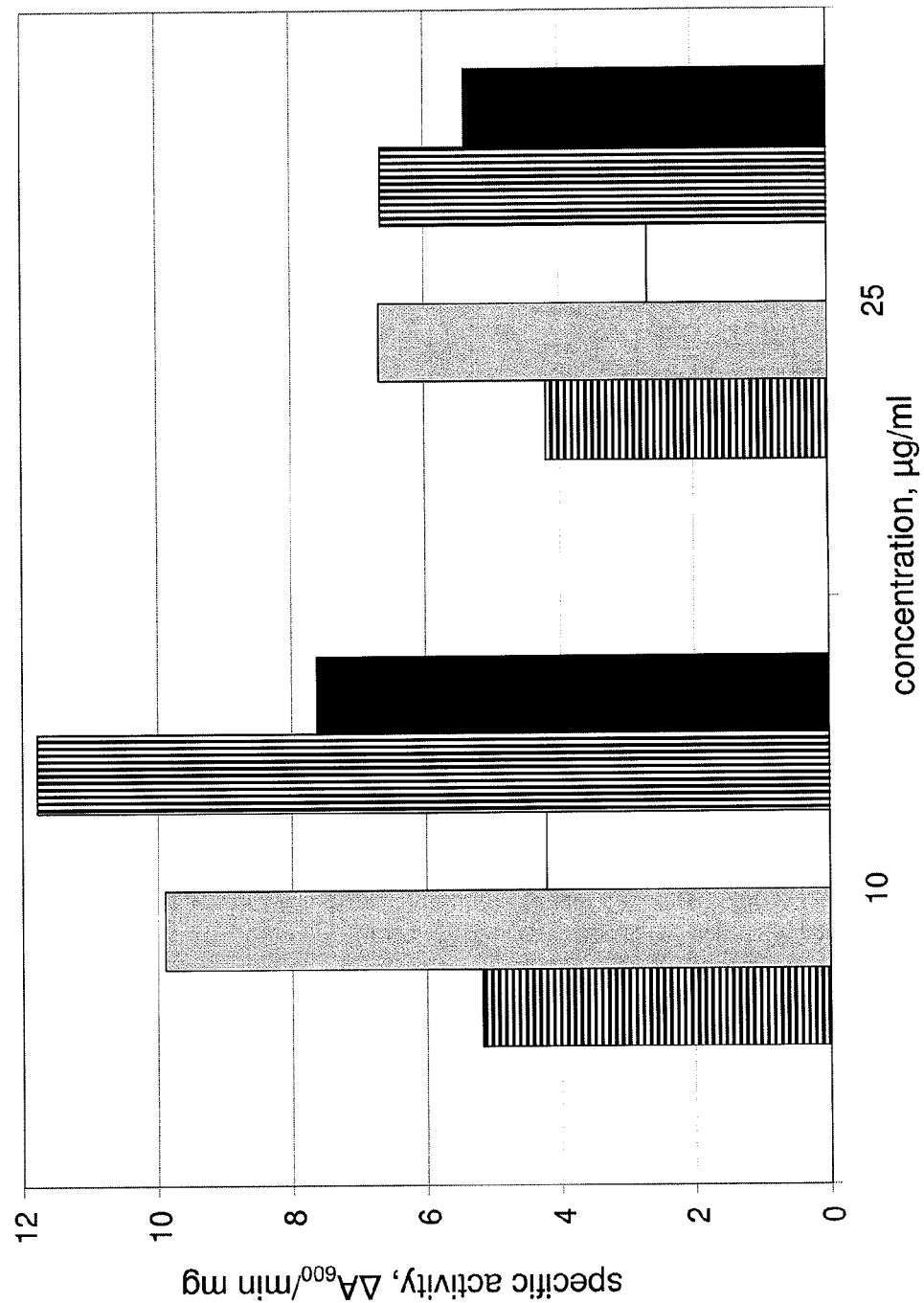
Figure 13:
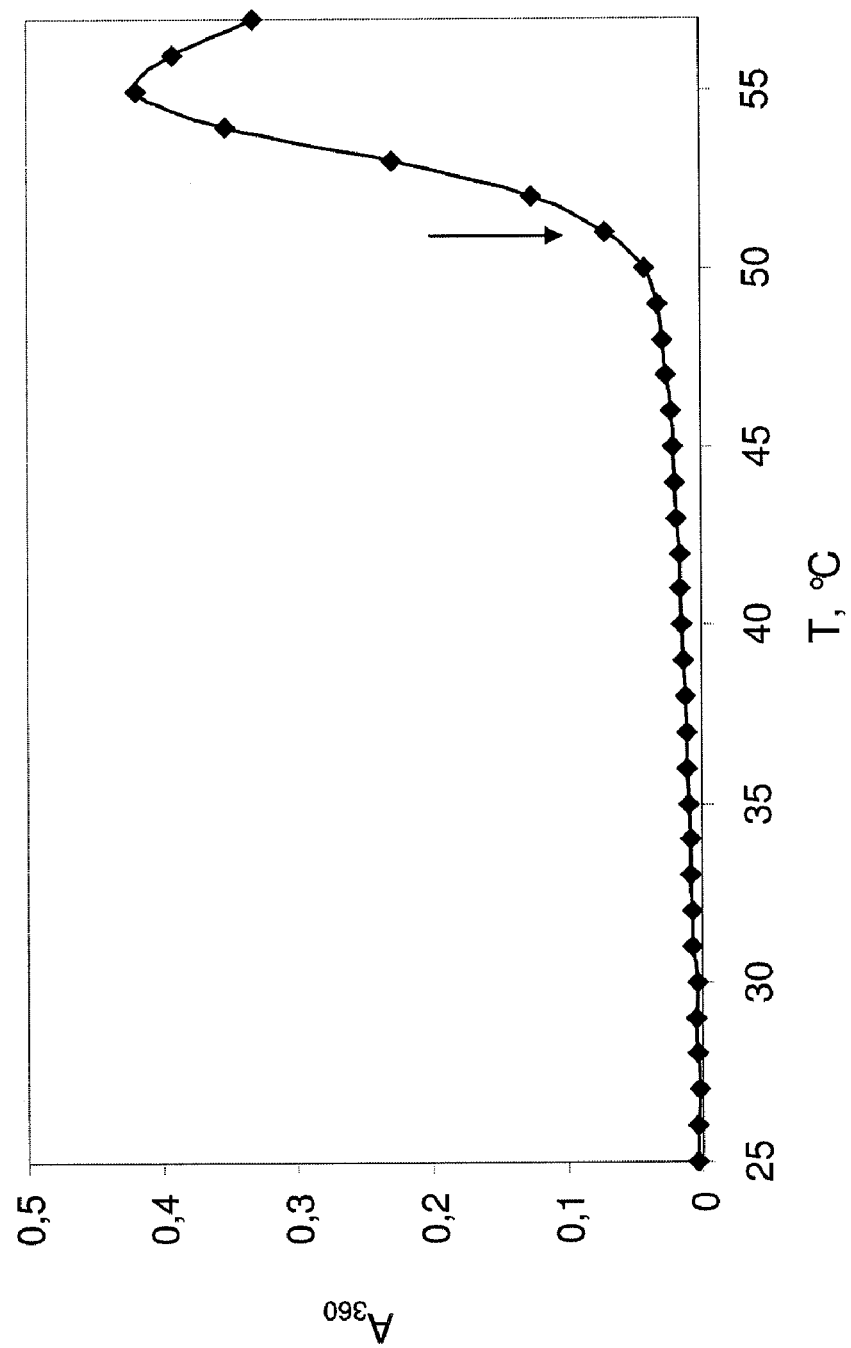

Table 1 depicts the host range for the EADplypitti26_CBDplyUSA compared to the wild-type endolysin Pitti26. Lysis activity on different *Staphylococcus* strains was tested with the agar plate activity assay. Strong (+++), medium (++), weak (+) and no (−) lysis are defined as described in the legend of FIG. 2. The first column depicts the strain number corresponding to the PROFOS culture collection. The second column mentions the origin of the respective strain. "Clinical isolate" means a strain isolated from a patient bacteria by the phage endolysins results in a drop of optical density (OD) which is measured by the turbidity assay. Target bacteria were grown in Brain Heart Infusion (Oxoid) until an $OD_{600}$ of around 0.8 is reached (exponential phase). The cells were harvested and resuspended in TBST buffer (20 mM Tris/HCl pH 7.5, 60 mM NaCl, 0.1% Tween) plus 2 mM $CaCl_2$ to an $OD_{600}$ of 1. Small volumes of concentrated endolysin solutions are added to final protein concentrations as indicated in the figures. Changes in $OD_{600}$ were followed at 30° C. in a sample volume of 1 ml in a photometer (Jasco) until a stable baseline is reached. The addition of the test proteins occurred without interruption of the measurement.

Different concentrations of isolated plypitti26 and EADplypitti26_CBDplyUSA endolysin were tested on *Staphylococcus aureus* cells. EADplypitti26_CBDplyUSA generally showed higher activity at the same protein concentration than plypitti26, again indicating superior properties compared to the naturally-occurring endolysin. With respect to the relatively low protein concentrations used in the assay, complete lysis (indicated by no residual absorption) is achieved in a very short time spam of several minutes with EADplypitti26_CBDplyUSA. The test was also performed with protein concentrations as low as 1 µg, 0.5 µg and even 0.2 µg, resulting also in complete lysis over a longer period of time. The resulting specific activity, defined as $\Delta OD_{600}$ per mg protein and minute, was calculated for EADplypitti26_CBDplyUSA as a value of ca. 50 units. Comparing this specific activity with state of the art full-length and truncated versions of phi11 endolysin, which are between 0.8 and 1.5 units (Donovan et al., 2006, FEMS Microbiol. Lett, 265, 133-139), EADplypitti26_CBDplyUSA turns out to be an extremely efficient staphylococcal endolysin. Even plypitti26 is significantly better than the phi11 endolysin.

Example 6

Activity Assay in Human Blood Serum

The activity of EADplypitti26_CBDplyUSA in blood serum was tested with the photometric turbidity assay according to Example 5. Log phase *S. aureus* cells were resuspended in blood serum and subsequently lysis assays with different concentrations of EADplypitti26_CBDplyUSA were performed. This assay allows a direct measuring of lysis of *S. aureus* cells in human blood serum. For efficient lysis in serum around 10-fold the amount of protein is required in comparison to lysis in osmolytically optimized lysis buffer. In addition, the kinetics of lysis are slower in blood serum than in buffer.

The activity of EADplypitti26_CBDplyUSA was tested in human blood serum. It could be demonstrated that EADplypitti26_CBDplyUSA is also an efficient lysin on *S. aureus* cells under conditions existent in human plasma, albeit a somewhat higher protein concentration is needed than under optimized standard assay conditions, and the lysis is somewhat slower.

Example 7

Stability During Long Term Incubation at Room Temperature

The stability of EADplypitti26_CBDplyUSA in comparison to plypitti26 was tested after incubation in storage buffer (20 mM Tris/HCl pH 7.5, 10 mM DTE, 0.1 mM $ZnSO_4$) at 25° C. for up to one week. Degradation of the proteins was monitored by SDS-PAGE and in turbidity assays. Whereas EADplypitti26_CBDplyUSA was stable over the whole time period tested as no changes were observed, plypitti26 was obviously degraded at incubation times longer than 9 hrs, and no full-length protein was visible after 120 h of incubation, but protein bands corresponding to smaller fragments became visible.

Remaining activity of the tested proteins was recorded using the turbidity assay under standard conditions (see Example 5). In accordance with the stability data obtained by SDS-PAGE, EADplypitti26_CBDplyUSA shows a slower decrease in activity in comparison to plypitti26. EADplypitti26_CBDplyUSA remains fully active for a long time, whereas the activity of the plypitti26 drops significantly already after 4 hrs.

This correlated with the decrease in activity, suggesting that only full-length endolysins were enzymatically active under these conditions. The experiment demonstrated, that especially EADplypitti26_CBDplyUSA is stable for reasonable periods of time even at room temperature. The stability extends a lot when the proteins are stored at lower temperatures, e.g., at 4° C. in a refrigerator or at temperatures of −20° C. or −80° C. in a deep freezer.

Example 8

Protease Stability Against Thrombin and V8 Protease

For the protease stability assay 50 µg thrombin were incubated overnight at 25° C. with the respective proteins at a final concentration of 1.1 mg/ml. The incubation buffer was 20 mM Tris/HCl pH 7.5, 10 mM DTE, 0.1 mM $ZnSO_4$. On the next day, the protein samples were analyzed on SDS-gels and in the turbidity assay. Whereas only a small amount of EADplypitti26_CBDplyUSA is degraded during the time of the assay, no full-length protein of plypitti26 is left under the same conditions. This means that EADplypitti26_CBDplyUSA is still highly active after incubation with thrombin whereas plypitti26 loses its activity completely. EADplypitti26_CBDplyUSA exhibits thrombin resistance as a property which renders it helpful for application in wounds or intravenous.

Protease stability against V8 protease was tested incubating endolysin (concentration 0.2 mg/ml) and V8 protease (1 µg/ml) in the following buffer: 20 mM Tris/HCl, 100 mM NaCl, pH 8.0 at 25° C. over night. On the next day, the protein samples were analyzed on SDS gels and in the turbidity assay.

Example 9

Stability in Human Blood

Activity was measured with the turbidity assay (Example 5) after preincubation of EADplypitti26_CBDplyUSA at 37° C. for the times indicated in either storage buffer (20 mM Tris/HCl pH 7.5, 10 mM DTE, 0.1 mM $ZnSO_4$) or human EDTA-blood. Human blood samples are centrifuged to sediment red blood cells at the times indicated, and 100 µl of protein solution from the supernatant are added to start the turbidity assay. Up to 2 h of incubation time, there is almost identical activity measured after preincubation in buffer and in blood. EADplypitti26_CBDplyUSA is inactivated almost completely after 4 h incubation in blood at 37° C., whereas there is 80% residual activity measured with the control incubation.

Example 10

Modified Endolysins

The inventors have generated several modified chimeric endolysins starting from the sequences of EADplypitti26_CBDplyUSA, EADplypitti26_CBDplypitti20, EADplypitti26_CBDALE1, and EADplypitti26_CBDLS.

N-terminal truncations. Several N-terminally truncated forms of EADplypitti26_CBDplyUSA were constructed and tested for activity in the agar plate assay. Two constructs that were N-terminally shortened by 4 and 9 amino acids, respectively, exhibited lytic activity in the plating assay, whereas a construct that was shortened by 29 amino acids did not exhibit activity any more.

Site-directed mutagenesis. In order to further stabilize and solubilize plypitti26, EADplypitti26_CBDplyUSA, EADplypitti26_CBDplypitti20, EADplypitti26_CBDALE1, and EADplypitti26_CBDLS, site-directed mutations at selected positions within the amino acid sequence were performed using specific primers for single amino acid substitutions, and the activity of the respective mutants was tested using the agar plate activity assay. The inventors substituted hydrophobic amino acids (F, W, Y, I, L) against the less hydrophobic amino acids R, D, E, N, K, Q, H, S, T, M, G, A by standard site directed mutagenesis methods. The charged amino acids E and R were exchanged against uncharged amino acids (Q or A for E, A for R). The C were exchanged against A or S. The substitutions as listed in Table 2 turned out to maintain the activity or to improve the properties of the endolysin as a therapeutic, diagnostic and prophylactic agent against staphylococcal infections.

TABLE 2

Modified endolysins exhibiting single amino acid mutations in plypitti26, EADplypitti26_CBDplyUSA, EADplypitti26_CBDplypitti20, EADplypitti26_CBDALE1, and EADplypitti26_CBDLS showing lytic activity against *Staphylococci*

Single amino acid mutations

| mutations | activity |
| --- | --- |
| W22R | Yes |
| F42A | Yes |
| Y44A | Yes |
| L55H | Yes |
| L56T | Yes |
| F67T | Yes |
| Y115S | Yes |
| W123M | Yes |
| W137A | Yes |
| W139A | Yes |
| W154H | Yes |
| E163Q | Yes |
| R167A | Yes |
| E179Q | Yes |
| E179A | Yes |
| E187Q | Yes |
| E189Q | Yes |
| Y200A | Yes |
| Y200H | Yes |
| Y275A | Yes |
| Y275M | Yes |
| Y276A | Yes |
| C282A | Yes |
| F300A | Yes |
| C303S | Yes |
| W310A | Yes |
| W310M | Yes |

Mutation of 2 to 7 residues

| Mutations | activity |
| --- | --- |
| L55H + L56T | yes |
| F67T + Y115S | yes |
| F67T + W137A | yes |
| F67T + W139A | yes |
| F67T + W154H | yes |
| Y115S + W137A | yes |
| Y115S + W139A | yes |
| E163Q + R167A | yes |
| E163Q + R169A | yes |
| E163A + R169A | yes |

TABLE 2-continued

Modified endolysins exhibiting single amino acid mutations in plypitti26, EADplypitti26_CBDplyUSA, EADplypitti26_CBDplypitti20, EADplypitti26_CBDALE1, and EADplypitti26_CBDLS showing lytic activity against *Staphylococci*

| | |
| --- | --- |
| E179A + E189Q | yes |
| E179Q + E189Q | yes |
| E163Q + R167A + E189Q | yes |
| E163A + R167A + E189Q | yes |
| E163Q + R167A + Y200H | yes |
| E163Q + R167A + E179Q + E189Q | yes |
| E163Q + R167A + E179A + E189Q | yes |
| E163A + R167A + E179Q + E189Q | yes |
| E163A + R167A + E179A + E189Q | yes |
| Y200A + Y275A | yes |
| Y200A + Y276A | yes |
| Y200A + C282A | yes |
| Y200A + F300A | yes |
| Y275A + Y276A | yes |
| Y275A + F300A | yes |
| C282A + F300A | yes |
| Y200A + Y275A + Y276A | yes |
| Y275A + Y276A + F300A | yes |
| L55H + L56T + E163A + R167A + Y200H | yes |
| E163A + R167A + E179A + E189Q + Y200H | yes |
| L55H + L56T + E163A + R167A + E179A + E189Q + Y200H | yes |
| S237L + R354Q + A367V | yes |

Example 11

Comparison of Lysis Activity in Buffer of Different Lysis Proteins Against *Staphylococcus aureus* Cells The assay was performed according to the protocol "turbidity assay to control lysis activity" described in Example 5. The specific activity ($\Delta A_{600}$/min mg) was calculated from the initial slopes of the lysis curves where the decrease in absorbance was almost linear. The assay was performed using lysis protein concentrations of 1 μg/ml and 10 μg/ml. It is seen that the specific activities are generally lower at a concentration of 10 μg/ml protein as the decrease in absorbance ($\Delta A_{600}$/min) measured has no linear correlation with the protein concentration. The following order of lysis activity in buffer resulted from the experiment: EADplypitti26_CBDLS-Add2_M5 better than EADplypitti 26_CBDplyUSA-Add2_M8 better than EADplypitti26_CBDALE1-Add2_M5 better than EADplypitti26_CBDplyUSA-Add2_M5 better than EADplypitti26_CBDplyUSA better than plypitti26 better than lysostaphin. Lysostaphin has the weakest performance in this assay, and plypitti26 the second weakest. Surprisingly however, a combination or the EAD of plypitti26 and the CBD of lysostaphin—EADplypitti26_CBDLS-Add2_M5— shows the second best performance. This is also reflected in the variant EADplypitti26_CBDALE1-Add2_M5, as ALE1 lysin is very similar to lysostaphin. The plypitti26 variants EADplypitti26_CBDplyUSA and EADplypitti26_CBDplyUSA-Add2_M5 show better lysis activity than plypitti26.

Example 12

Comparison of Lysis Activity in Human Blood Serum of Different Lysis Proteins Against *Staphylococcus aureus* Cells The assay was performed according to the protocol "activity assay in human blood serum" described in Example 6. The specific activity ($\Delta A_{600}$/min mg) was calculated from the initial slopes of the lysis curves where the decrease in absorbance was almost linear. The assay was performed using lysis protein concentrations of 10 μg/ml and 25 μg/ml. It is seen that the specific activities are somewhat lower at a concentration of 25 μg/ml protein as the decrease in absorbance ($\Delta A_{600}$/min) measured has no linear correlation with the protein concentration. The following order of lysis activity in human blood serum resulted from the experiment using 10 μg/ml lysis protein: EADplypitti26_CBDLS-Add2_M5 better than EADplypitti26_CBDplyUSA-Add2_M5 better than EADplypitti26_CBDALE1-Add2_M5 better than EADplypitti26_CBDplyUSA better than EADplypitti26_CBDplyUSA-Add2_M8. It turned out, that lysis efficiency of the different endolysin constructs in human blood serum is different from that measured in buffer. Endolysin plypitti26 exhibited no lytic activity on Stapylococcus aureus cells in human blood serum, but seems to be inhibited by an unknown factor. The modified variants of plypitti26 exhibiting the CBD of plyUSA, namely EADplypitti26_CBDplyUSA and EADplypitti26_CBDplyUSA-Add2_M5 and EADplypitti26_CBDplyUSA-Add2_M8 show specific lysis activities in human blood serum better than plypitti26. The construct EADplypitti26_CBDLS-Add2_M5 using the CBD of lysostaphin shows the best specific lysis activity in human blood serum although the lysis activity in buffer of lysostaphin was very poor. The construct EADplypitti26_CBDALE1-Add2_M5 using the CBD of ALE-1 lysin shows the third best specific lysis activity in human blood serum.

Example 13

Thermal Stability Assay

The thermal stability of the Staphylococcus endolysins was measured in a thermostability assay measuring aggregation of the protein at a wavelength of 360 nm in a photometer. The proteins (concentration 0.1 mg/ml) were dissolved in a buffer containing 20 mM Hepes, 10 mM $CaCl_2$, 50 mM arginin, pH 7.5. A cuvette containing the buffered protein solution was put in a photometer and heated in steps of 1° C. per min. The absorbance at 360 nm ($A_{360}$) was measured between room temperature and around 65° C. Without protein denaturation, the $A_{360}$ signal shows only a slight slope, but beginning from a specific temperature, the aggregation temperature $T_{aggr}$, the absorption line begins to rise and describes kind of a peak. This signal change coincides with aggregation and concomitant inactivation of the protein. Thus, the aggregation temperature $T_{aggr}$ observed is a measure for the thermal stability of the protein. A comparison of the $T_{aggr}$ for different Staphylococcus endolysin variant is given in Table 3.

TABLE 3

$T_{aggr}$ for different Staphylococcus endolysin variant

| Protein | $T_{aggr}$, ° C. |
|---|---|
| ply_pitti26 | 50 |
| EADplypitti26_CBDplyUSA | 55 |
| EADplypitti26_CBDplyUSA-Add2_M5 | 55 |
| EADplypitti26_CBDplyUSA-Add2_M8 | 55 |
| EADplypitti26_CBDLS-Add2_M5 | 56 |
| EADplypitti26_CBDALE1-Add2_M5 | 51 |

It turned out that ply_pitti26 is the least stable enzyme measured in this experiment. The exchange of the CBD of ply_pitti26 for the CBD from plyUSA or from lysostaphin increases the stability by 5° C. EADplypitti26_CBDLS-Add2_M5 is the most stable endolysin with a $T_{aggr}$ of 56° C., followed by EADplypitti26_CBDplyUSA-Add2_M5, EADplypitti26_CBDplyUSA, and EADplypitti26_CBDplyUSA-Add2_M8 exhibiting $T_{aggr}$ of 55° C., each. The exchange of the CBD of ply_pitti26 for the CBD from ALE-1 lysin results only in a marginal stabilisation of 1° C.

Example 14

Characterisation of plypitti26 and Variants thereof with Respect to Advantageous Properties for Use as a Therapeutic, Diagnostic and Prophylactic Agent Against Staphylococcal Infections Different chimeric endolysins derived from plypitti26, and modified proteins exhibiting up to 7 single amino acid mutations were compared with respect to different properties concerning activity and stability of the endolysins. Protease resistance was tested according to the protocol described in Example 8, lysis activity in buffer and serum according to Examples 5 and 6, respectively, the host range was determined in the agar plate assay (Example 4), and the stability during long term incubation with the assay described in Example 7. The results are summarized in a semi-quantitative manner in Table 4.

TABLE 4

Comparison of properties of different protein variants of Staphylococcus endolysin ply_pitti26 for a use according to the invention

| Endolysin construct Amino acid substitutions | | | EADpitti26_ CBDUSA E163A, R167A, Y200H | EADpitti26_ CBDUSA-Add2 E164A, R168A, E180A, E190Q, Y201H | EADpitti26_ CBDpitti20 | EADpitti26_ CBDUSA-Add2_M5 L56H, L57T, E164A, R168A, Y201H |
|---|---|---|---|---|---|---|
| property | assay | plypitti26 | | | | |
| thrombin resistance | SDS-PAGE | − | +++ | ++ | + | +++ |
| thrombin resistance | turbidity | − | − | − | + | ++ |
| V8 protease resistance | SDS-PAGE | − | − | + | − | − |
| activity in buffer | turbidity | + | + | +++ | + | +++ |
| activity in serum | turbidity | n.d. | n.d. | n.d. | n.d. | +++ |

TABLE 4-continued

Comparison of properties of different protein variants of *Staphylococcus* endolysin ply_pitti26 for a use according to the invention

| property | assay | | | | | |
|---|---|---|---|---|---|---|
| host range *Staphylococcus* | agar plate | ++ | +++ | +++ | + | +++ |
| host range *S. aureus* | agar plate | ++ | +++ | +++ | +++ | +++ |
| host range *S. aureus* MRSA | agar plate | ++ | +++ | +++ | + | +++ |
| storage stability | turbidity | + | n.d. | n.d. | n.d. | +++ |

| Endolysin construct Amino acid substitutions | | EADpitti26_CBDUSA-Add2 L56H, L57T, E164A, R168A, E180A, E190Q, Y201H | EADpitti26_CBDUSA-Add2 L56H, L57T, | EADpitti26_CBDUSA-Add2 E164A, R168A | EADpitti26_CBDUSA-Add2 |
|---|---|---|---|---|---|
| property | assay | | | | |
| thrombin resistance | SDS-PAGE | +++ | − | +++ | + |
| thrombin resistance | turbidity | ++ | − | − | + |
| V8 protease resistance | SDS-PAGE | + | − | − | − |
| activity in buffer | turbidity | +++ | ++ | + | +++ |
| activity in serum | turbidity | ++ | n.d. | n.d. | + |
| host range *Staphylococcus* | agar plate | +++ | +++ | +++ | +++ |
| host range *S. aureus* | agar plate | +++ | +++ | +++ | +++ |
| host range *S. aureus* MRSA | agar plate | +++ | +++ | +++ | +++ |
| storage stability | turbidity | ++ | +++ | ++ | +++ |

+++ - property measured in the respective assay very good compared with the other endolysin constructs measured
++ - property measured in the respective assay good compared with the other endolysin constructs measured
+ - property measured in the respective assay less pronounced compared with the other endolysin constructs measured
− − property not measurable under the conditions used in the respective assay compared with the other endolysin constructs measured
n.d. - property not determined with the respective endolysin construct All of the variants of plypitti26 constructed as described in this invention show advantages over the naturally occurring endolysin in stability or activity or both. The variants exhibiting the mutations E164A (or E163A in EADpitti26_CBDUSA) and R168A (or R167A in EADpitti26_CBDUSA), but also the chimeric constructs EADpitti26_CBDUSA, EADpitti26_CBDUSA-Add2 and EADpitti26_CBDpitti20 show better resistance to thrombin than plypitti26. In the variants EADpitti26_CBDUSA-Add2_M5 (L56H, L57T, E164A, R168A, Y201H) and EADpitti26_CBDUSA-Add2 (L56H, L57T, E164A, R168A, E180A, E190Q, Y201H) and to a lower degree in the variants EADpitti26_CBDUSA, EADpitti26_CBDUSA-Add2 and EADpitti26_CBDpitti20 this is also pronounced when testing the residual endolysin activity after thrombin digestion. This shows that two strategies lead to an improved resistance against proteases. First, the mutations of residues involved in the substrate recognition of the proteases, (in this case single amino acid substitutions like R168Q) and second, a change in the overall conformation of the protein in the was that the accessibility of the digestion site for the protease is probably reduced (in the case the construction of chimeric constructs by the exchange of CBDs). The lysis activity against *Staphylococcus* cells was superior to plypitti26 in the variant EADpitti26_CBDUSA-Add2 (L56H, L57T) and especially in the variants EADpitti26_CBDUSA-Add2, EADpitti26_CBDUSA-Add2 (E164A, R168A, E180A, E190Q, Y201H), EADpitti26_CBDUSA-Add2 (L56H, L57T, E164A, R168A, Y201H) and EADpitti26_CBDUSA-Add2 (L56H, L57T, E164A, R168A, E180A, E190Q, Y201H). The variants EADpitti26_CBDUSA-Add2 (L56H, L57T, E164A, R168A, Y201H) and EADpitti26_CBDUSA-Add2 (L56H, L57T, E164A, R168A, E180A, E190Q, Y201H) also show a very good to good lysis activity in human blood serum. It turned out that especially the mutations L56H, L57T, and Y201H are beneficial for the lysis activity of the protein. The host range of the plypitti26 variants was tested using 67 strains of the genus *Staphylococcus*, 32 strains of *Staphylococcus aureus*, and 12 *Staphylococcus aureus* MRSA strains. A very good sensitivity with respect to host range (+++) means the lysis of more than 80% of the *Staphylococcus* strains, more than 90% of the *Staphylococcus aureus* strains, and more than 75% of the *Staphylococcus aureus* MRSA strains, Almost all variants show a very good host range sensitivity towards *Staphylococcus* cells. Plypitti26 host range sensitivity is slightly reduced, and the sensitivity of the chimeric construct EADpitti26_CBDpitti20 is weaker towards cells from the genus *Staphylococcus*, and MRSA strains. Long-term stability at room temperature was improved in all the variants tested compared to plypitti26. Particularly mentioned with respect to storage stability are the variants EADpitti26_CBDUSA, EADpitti26_CBDUSA- Add2 (L56H, L57T) and EADpitti26_CBDUSA-Add2 (L56H, L57T, E164A, R168A, E180A, E190Q, Y201H). The mutations L56H and L57T have a positive effect on stability and solubility of plypitti26. In summary, all the variants presented show advantages over the naturally existing endolysin plypitti26. Other variants are EADpitti26_CBDUSA-Add2 (L56H, L57T, E164A, R168A, Y201H) and EADpitti26_CBDUSA-Add2 (L56H, L57T, E164A, R168A, E180A, E190Q, Y201H), which show the best performance over all properties tested.

Example 15

Immunogenicity Study

For a use of the endolysins as a therapeutic or prophylactic agent against staphylococcal infections, the immunogenicity of the proteins has to be tested in an animal model in order to get information about the immune response of the organisms elicited by the foreign proteins. Ten female Balb/c mice per group were used as an animal model for the immunogenicity study for IV-therapy. The plypitti26 endolysin variant EADplypitti26_CBDplyUSA-Add2_M5 was applied with a slow, low pressure IV bolus injection in formulation buffer (25 mM Tris pH 7.5, 10 mM citrate, 10 mM CaCl$_2$, 300 mM arginine) at t=0 h, 24 h and 48 h for the three groups at a doses of 15 mg/kg body weight. Endpoint serum withdrawal was after 2 or 4 or 8 weeks for the three groups, respectively. Three mice in each group achieved medication with buffer without endolysin as a control. Three female Balb/c mice per group were used as an animal model for the control immunogenicity study for IP-injection. Here, the plypitti26 endolysin variant EADplypitti26_CBDplyUSA-Add2_M5 was applied with IP injection with aduivans water/oil emulsion at t=0 h, 14 days and 28 days for the three groups at a dosis of 15 mg/kg body weight. Endpoint serum withdrawal was after 10 or 21 or 35 days for the three groups, respectively. The degree of immunogenicity was tested in an ELISA assay using EADplypitti26_CBDplyUSA-Add2_M5 coupled to microtiter plates and calorimetric signal detection using a secondary antibody against the diverse groups of antibodies resulting in the immune response. The results for the IV and IP injection are given in Tables 5 and 6. Depicted is the lowest antibody titer which still gives a signal significantly below the background signal which was derived from the controls.

TABLE 5

Antibody titers after IV injection of EADplypitti26_CBDplyUSA-Add2_M5

| Time | Antibody titer (1/x) | | | | |
|---|---|---|---|---|---|
| (weeks) | IgA | IgM | IgG1 | IgG2a | IgE |
| 0 | 0 | 0 | 0 | 0 | 0 |
| 2 | 100 | 100 | 400 | 400 | 100 |
| 4 | 6400 | 1600 | 6400 | 6400 | 400 |
| 8 | 6400 | 6400 | 25000 | 6400 | 6400 |

TABLE 6

Antibody titers after IP injection of EADplypitti26_CBDplyUSA-Add2_M5

| time | antibody titer (1/x) | | | | |
|---|---|---|---|---|---|
| (days) | IgA | IgM | IgG1 | IgG2a | IgE |
| 0 | 0 | 0 | 0 | 0 | 0 |
| 10 | 1600 | 6400 | 100000 | 25000 | 6400 |
| 21 | 100000 | 400000 | 400000 | 1600000 | 100000 |
| 35 | 1600000 | 1600000 | 1600000 | 1600000 | 1600000 |

It is seen that antibody titers were low after IV injection of EADplypitti26_CBDplyUSA-Add2_M5 compared to IP injection which was used as a control for a strong immune response.

Example 16

Neutralization of the Activity of EADplypitti26_CBDplyUSA-Add2_M5 by Mouse Antisera In order to test whether the antibodies built during the immune response after IV injection against EADplypitti26_CBDplyUSA-Add2_M5 are able to neutralize the activity of the endolysin, the lysis activity against a Staphylococcal cell wall preparation was tested in a microtiter plate turbidity assay. EADplypitti26_CBDplyUSA-Add2_M5 (0.1 mg/ml) in buffer 20 mM Hepes, 150 mM NaCl, pH 7.4 was incubated for 1 h at 30° C. with serial dilutions (dilution factors of 0, 0.5, 0.2, 0.1, 0.05, 0.1, 0.05, 0.01, 0.001, 0.0001) of mice antisera generated 4 and 8 weeks after IV injection according to the protocol described in example 15. 10 µl of the incubated solutions of the different serial dilutions were mixed with 190 ml staphylococcal cell wall preparation, and the decrease in absorption at 620 nm measured over time starting from an $A_{620}$ of ca. 2.0. The time needed for a decrease in absorption of $\Delta A_{620}=0.1$ is a measure for the activity of the endolysin. The activities measured for samples after addition of preimmune sera at the respective dilutions served as controls for activity. The activity values presented in table 7 represent mean values derived from the sera of the 7 mice each IV-injected with EADplypitti26_CBDplyUSA-Add2_M5 as described in Example 15.

TABLE 7

Endolysin activity against Staphylococcal cell wall preparations after neutralisation with sera derived from IV injection with EADplypitti26_CBDplyUSA-Add2_M5

| | Activity (%) | | |
|---|---|---|---|
| serum dilution | preimmune serum | serum 4 weeks | serum 8 weeks |
| 0 | 100.0 | 94.9 | 99.4 |
| 0.5 | 100.0 | 102.3 | 115.0 |
| 0.2 | 100.0 | 109.0 | 114.8 |
| 0.1 | 100.0 | 110.8 | 108.0 |
| 0.05 | 100.0 | 114.4 | 102.5 |
| 0.01 | 100.0 | 103.5 | 100.2 |
| 0.001 | 100.0 | 110.4 | 83.2 |
| 0.0001 | 100.0 | 109.1 | 100.0 |

The activity assay shows that the staphylococcal endolysin variant according to the invention EADplypitti26_CBDplyUSA-Add2_M5 is not inactivated by the antibodies generated after IV injection to a significant level. On the contrary, a slight activation of the endolysin activity is observed after addition of antisera in most of the samples. Thus, the antibodies generated during the immune response after IV injection are not able to neutralise the endolysin activity of EADplypitti26_CBDplyUSA-Add2_M5 to a significant degree.

Example 17

High Dose Toxicity of the Staphylococcal Endolysin Variant EADplypitti26_CBDplyUSA-Add2_M5 in Mice In order to test the potential toxicity of EADplypitti26_CBDplyUSA-Add2_M5, healthy female CFW1 mice were IV bolus injected with a dosis of 100 mg endolysin per kg body weight. Injection was repeated after time periods of 1 h, 6 h, and 22 h. The injection volume was 0.2 ml each in buffer 20 mM Tris, 10 mM $CaCl_2$, 10 mM citrate, 300 mM arginine, pH 7.5. The mice were controlled for clinical signs, body weight, and lethality daily during the next 5 days. In none of the mice tested, there was a loss of body weight or other clinical signs like fever or tremor during the next five days indicating that even a high dose of the staphylococcal endolysin variant EADplypitti26_CBDplyUSA-Add2_M5 was not toxic for healthy mice after repeated IV injection. From the animal model, the staphylococcal endolysin variant EADplypitti26_CBDplyUSA-Add2_M5 appears to be applicable for therapy or prevention of staphylococcal infections without toxic effects.

Example 18

Pharmacokinetic Study Using the Staphylococcal Endolysin Variant EADplypitti26_CBDplyUSA-Add2_M5

A pharmacokinetic study in rats was performed in order to determine the half-life of EADplypitti26_CBDplyUSA-Add2_M5 in a living organism. Twenty-four male Sprague Dawley (CD) rats were inoculated IV into the leg vein with a doses of 12 mg endolysin per kg body weight. EADplypitti26_CBDplyUSA_M5 was dissolved in buffer 20 mM Tris, 10 mM $CaCl_2$, 10 mM citrate, 300 mM arginine, pH 7.5. 3 animals each were killed 5 min, 15 min, 30 min, 60 min, 120 min, 240 min or 480 min after IV injection. 3 animals of the control group received only buffer for injection. After killing, blood samples were taken immediately, serum prepared, and frozen in liquid nitrogen. In addition, the organs heart, kidney, liver, spleen and lung were prepared and also frozen in liquid nitrogen. The residual activity of the endolysin variant EADplypitti26_CBDplyUSA-Add2_M5 was determined in a turbidity assay performed in a microtiter plate format. 20 µl serum was mixed with 200 µl staphylococcal cell wall preparation which had an absorption at 620 nm of $A_{620}$=2.0. The time needed for the decrease of $A_{620}$ of 0.1 ($\Delta A_{620}$=0.1) was taken as a measure for the activity of the endolysin. As controls, the activity of respective concentrations (150 µg/ml) of EADplypitti26_CBDplyUSA-Add2_M5 endolysin in buffer and pre-immune serum were measured. A second assay for determination of the half-life of EADplypitti26_CBDplyUSA-Add2_M5 endolysin was a Western-blot analysis of the protein using polyclonal anti EADplypitti26_CBDplyUSA-Add2_M5 endolysin rabbit antiserum in a dilution of 1:$10^5$ and an alkaline phosphatase goat anti-rabbit IgG conjugate as secondary antibody. This Western-blot analysis was also used for the organ extracts, which were prepared by homogenisation of the thawed organs using glass beads and spatula. Organ extracts, blood and serum samples were applied to SDS-polyacrylamide gels, and the separated polypeptide bands blotted to PVDF membranes and developed using the antibodies described.

From the activity assay described the half-life of the variant EADplypitti26_CBDplyUSA-Add2_M5 after IV injection in rat was about 60 min. 2 h after application there was almost no residual activity measurable. A comparison of the first sample taken after 5 minutes to the activity of the protein in pre-immune serum and formulation buffer showed that there is almost no loss of activity directly after application, which could be due to adsorption of the protein to blood cells or epithelial cells of the blood vessels. From the Western blot assay which was also performed in samples taken from the different organs, it became evident that the disappearance of the protein band for EADplypitti26_CBDplyUSA-Add2_M5 coincided with the loss of activity. Very similar pharmacokinetics were observed in blood, serum and the organs examined suggesting that clearance of the protein is similar in different parts of the body. The only difference observed was that the endolysin was visible as the full-length form in blood, serum, heart, lung, liver, and spleen samples, whereas fragments of the protein were detected at all time points in the kidney sample. The endolysin variant EADplypitti26_CBDplyUSA-Add2_M5 seems to be digested in rat kidney by proteases present in that organ. The pharmacokinetic study identified the staphylococcal endolysin variant EADplypitti26_CBDplyUSA-Add2_M5 as a potential pharmaceutical agent suitable for use in therapy and prevention of staphylococcal infections.

Example 19

Efficacy Study of Endolysin EADpitti26_CBDUSA-Add2_M5 After Systemic Infection of Mice with *Staphylococcus aureus* Cells In order to test the efficacy of endolysin EADpitti26_CBDUSA-Add2_M5 as a therapeutic agent against *Staphylococcus* infections, mice were IV infected with *Staphylococcus aureus* cells, and the IV treatment with endolysin EADpitti26_CBDUSA-Add2_M5 was compared with other treatments with respect to survival of the test animals. 48 female healthy CFW1 mice were IV inoculated with 2×$10^8$ *Staphylococcus aureus* cells of the strain DSMZ 11823 per mouse. The mice were divided into 7 groups of 6 animals. The first three groups of mice were treated with high (100 mg protein per kg body weight), medium (25 mg protein per kg body weight), or low (5 mg protein per kg body weight) dosages of endolysin EADpitti26_CBDUSA-AAd2_M5 which were given in three IV injections 1 h, 6 h, and 22 h post infection. One group of mice received the same injections of formulation buffer (20 mM Tris, 10 mM $CaCl_2$, 10 mM citrate, 300 mM arginine, pH 7.5). Three groups of mice were treated with high (20 mg protein per kg body weight), medium (5 mg protein per kg body weight), or low (1.25 mg protein per kg body weight) dosages of the antibiotic vancomycin. One group of mice did not receive any treatment, and served as a control for the virulence of the *Staphylococcus aureus* cells. The survival of the mice was observed for the next 5 days after infection. The results are summarized in Table 8.

TABLE 8

Survival of mice after *Staphylococcus aureus* infection achieving different treatments

| Treatment | Concentration (mg/kg) | Survival (number of animals) | | | | | |
|---|---|---|---|---|---|---|---|
| | | day 0 | day 1 | day 2 | day 3 | day 4 | day 5 |
| EADpitti26_CBDUSA-Add2_M5: high dosage | 100 | 6 | 6 | 6 | 6 | 6 | 6 |
| EADpitti26_CBDUSA-Add2_M5: medium dosage | 25 | 6 | 6 | 6 | 6 | 6 | 6 |
| EADpitti26_CBDUSA-Add2_M5: low dosage | 5 | 6 | 6 | 6 | 6 | 6 | 6 |
| Formulation buffer | — | 6 | 4 | 0 | 0 | 0 | 0 |
| Vancomycin: high dosage | 20 | 6 | 6 | 6 | 6 | 6 | 6 |
| Vancomycin: medium dosage | 5 | 6 | 6 | 6 | 6 | 6 | 6 |
| Vancomycin: low dosage | 1.25 | 4 | 4 | 4 | 4 | 4 | 2 |
| Control | — | 6 | 6 | 2 | 0 | 0 | 0 |

It turned out that IV application of endolysin EADpitti26_CBDUSA-Add2_M5 after IV inoculation of mice with *Staphylococcus aureus* cells at a concentration of $2 \times 10^8$ cells guaranteed survival of all mice within the observation period at all three dosages tested. Without treatment, all the animals from the control group had died on day 3. The formulation buffer for the endolysin itself seemed to have a somewhat negative effect, as in this group all the animals had died already on day 2. After treatment with the antibiotic vancomycin all the animals survived in the groups treated with high and medium dosages, but some animals died in the group treated with the low dosage of antibiotic. From the efficacy study, endolysin EADpitti26_CBDUSA-Add2_M5 appears a good tool for treatment of *Staphylococcus aureus* infections, and an alternative to treatment with antibiotics were often resistances occur.

\* \* \* \* \* \* \* \* \* \* \* \* \* \* \*

All of the compositions and/or methods disclosed and claimed herein can be made and executed without undue experimentation in light of the present disclosure. While the compositions and methods of this invention have been described in terms of particular embodiments, it will be apparent to those of skill in the art that variations may be applied to the compositions and/or methods in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,997,862

U.S. Patent Publn. 2007/077235

Adams, In: *Bacteriophages*, Interscience Pub., NY, 447-451, 1959.

Cheng et al., *Antimicrob. Agents Chemother.*, 49:111-117, 2005.

Croux et al., *Molec. Microbiol.* 9:1019-1025, 1993.

Diaz et al., *Proc. Natl. Acad. Sci. USA*, 87:8125-8129, 1990.

Diep et al., *The Lancet*, 367:731-739, 2006.

Donovan et al., *Appl. Environm. Microbiol.*, 72:2988-2996, 2006.

Entenza et al., *Antimicrob. Agents Chemother.*, 49:4789-4792, 2005.

EP 1399551

Evan et al., *Mol. Cell Biol.*, 5:3610-3616, 1985.

Fischetti, *BMC Oral Health*, 6:16-19, 2006.

GB 2,255,561

Loeffler et al., *Science*, 94:2170-2172, 2001.

Loessner et al., *FEMS Microbiol. Lett.*, 162:265-274, 1998.

Lu et al., *J. Biol. Chem.*, 281:549-558, 2006.

Navarre et al., *J. Biol. Chem.*, 274:15847-15856, 1999.

Nelson & Fischetti, *Proc. Natl. Acad. Sci. USA*, 98:4107-4112, 2001.

Nieba et al., *Anal. Biochem.*, 252:217-228, 1997.

PCT Appln. WO 2008/077397

Peng et al., *Protein Expr. Purif.*, 412:95-100, 1993.

Sambrook et al., Molecular cloning. A laboratory manual; $2^{nd}$ Ed., Cold Spring Harbor Laboratory Press, 1989.

Sass & Bierbaum, *Appl. Environm. Microbiol.*, 73:347-352, 2007.

Schuch et al., *Nature*, 418:884-889, 2002.

Takac et al., *Antimicrob. Agents Chemother.*, 49, 2934-2940, 2005.

Voss & Skerra, *Protein Eng.*, 10:975-982, 1997.

Yokoi et al., *Gene*, 351:97-108, 2005.

What is claimed:

1. A purified and isolated polypeptide comprising the sequence as depicted in SEQ ID NO:1 or variant thereof, said variant being:
   a) a polypeptide comprising a sequence in which the CBD of SEQ ID NO:1 has been replaced by a CBD domain of another *Staphylococci* specific endolysin; or
   b) a polypeptide comprising the sequence as depicted in SEQ ID NO:1 lacking 1, 2, 3, 5, 6, 7, 8, 10, 11, 12, 13, 14, 15, 16, 17, 18, 19, 20, 21, 22, 23, 24, 25, 26, 27 or 28 N-terminal amino acid residues of SEQ ID NO:1; or
   c) a polypeptide comprising the sequence of SEQ ID NO:1 except for at least the first N-terminal amino acid and at most the first 28 N-terminal amino acids of SEQ ID NO:1 and wherein the sequence as depicted in SEQ ID NO:1 exhibits single or multiple substitutions with regard to SEQ ID NO: 1, wherein
      i) the substituted residues are selected from the following amino acid residues of SEQ ID NO:1: F19, W22, W36, F42, Y44, L55, L56, F67, L74, Y78, W107, Y115, I116, Y119, W123, W128, W137, W139, W154, E163, R167, E179, E189, Y200, Y275, Y276, C282, F300 and C303, or
      ii) wherein one or more substitutions are selected from the group comprising: W22R, F42A, Y44A, F67T, Y115S, W123M, W137A, W139A, W154H, E163A, E179Q, E179A, E187Q, Y200A, Y200H, Y275A, Y275M, Y276A, C282A, F300A, C303S, W310A and W310M, or
      iii) wherein one or more substitutions are selected from the group comprising: F67T+Y115S, F67T+W137A, F67T+W139A, F67T+W154H, Y115S+W137A, Y115S+W139A, E163Q+R169A, E163A+R169A, E163Q+R167A+E189Q, E163A+R167A+E189Q, E163Q+R167A+E179Q+E189Q, E163Q+R167A+E179A+E189Q, E163A+R167A+E179Q+E189Q, E163A+R167A+E179A+E189Q, Y200A+Y275A, Y200A+Y276A, Y200A+C282A, Y200A+F300A, Y275A+Y276A, L55H+L56T+E163A+R167A+Y200H, E163A+R167A+E179A+E189Q+Y200H, L55H ±L56T+E163A+R167A+E179A+E189Q+Y200H, S237L+R354Q+A367V, and L55H+L56T+E163A+R167A+Y200H+S237L+R354Q+A367V; or
   d) a polypeptide comprising one or more amino acid substitutions in the sequence of SEQ ID NO:1 i) wherein the substituted residues are selected from the following amino acid residues of SEQ ID NO:1: F19, W22, W36, F42, Y44, L55, L56, F67, L74, Y78, W107, Y115, I116, Y119, W123, W128, W137, W139, W154, E163, R167, E179, E189, Y200, Y275, Y276, C282, F300 and C303, or ii) wherein one or more substitutions are selected from the group comprising: W22R, F42A, Y44A, F67T, Y115S, W123M, W137A, W139A, W154H, E163A, E179Q, E179A, E187Q, Y200A, Y200H, Y275A, Y275M, Y276A, C282A F300A, C303S, W310A and W310M, or iii) wherein one or more substitutions are selected from the group comprising: F67T+Y115S, F67T+W137A, F67T+W139A, F67T+W154H, Y115S+W137A, Y115S+W139A, E163Q+R169A, E163A+R169A, E163Q+R167A+E189Q, E163A+R167A+E189Q, E163Q+R167A+E179Q+E189Q, E163Q+R167A+E179A+E189Q, E163A+R167A+E179Q+E189Q, E163A+R167A+E179A+E189Q, Y200A+Y275A, Y200A+Y276A, Y200A+C282A, Y200A+F300A, Y275A+Y276A, L55H+L56T+E163A+R167A+Y200H, E163A+R167A+E179A+E189Q+Y200H, L55H+L56T+E163A+R167A+E179A+E189Q+Y200H, S237L+R354Q+A367V, and L55H+L56T+E163A+R167A+Y200H+S237L+R354Q+A367V; or e) a polypeptide comprising in addition to the sequence of SEQ ID NO: 1 sequences representing marker moieties, tags or other functional polypeptide sequences; or f) a polypeptide comprising one or more additional amino acid residues inserted into the amino acid sequence according to SEQ ID NO:1; or g) a polypeptide comprising a polypeptide sequence representing any combination of variants a), b), c), d), e) and f).

2. The polypeptide according to claim 1, wherein the polypeptide lyses *S. aureus, S. aureus (MRSA), S. epidermidis, S. haemolyticus, S. simulans, S. saprophyticus, S. chromogenes, S. hyicus, S. warneri* and/or *S. xylosus*.

3. The polypeptide according to claim 1, wherein the variant of the polypeptide comprising the sequence as depicted in SEQ ID NO:1 comprises an endolysin cell binding domain of the SH3 type.

4. The polypeptide according to claim 1, wherein the variant of the polypeptide comprising the sequence as depicted in SEQ ID NO:1 comprises a CBD domain selected from the endolysin CBD domains of ply_USA or ply_pitti20.

5. The polypeptide according to claim 4, wherein the variant of the polypeptide comprising the sequence as depicted in SEQ ID NO:1 comprises a CBD domain as denoted in SEQ ID NOs: 3 or 5.

6. The polypeptide according to claim 5, comprising the sequence as denoted in SEQ ID NOs: 7 or 11.

7. The polypeptide according to claim 1 in part c)i), wherein replacements of amino acids residues F, W, Y, I, L are exchanged for amino acids residues R, D, E, N, K, Q, H, S, T, M, G or A.

8. The polypeptide according to claim 1, in part d)i), wherein replacements of amino acids residues F, W, Y, I, L are exchanged for amino acids residues R, D, E, N, K, Q, H, S, T, M, G or A.

9. The polypeptide according to claim 1, wherein the polypeptide comprises biotin or Streptavidin as additional marker moiety.

10. The polypeptide according to claim 1, wherein the polypeptide further comprises a HA-tag, His-tag, Strep-tag, Myc-tag or GST-tag.

11. The polypeptide according to claim 10, wherein the polypeptide comprises the sequence as denoted in in SEQ ID NO: 9 or SEQ ID NO: 13.

12. The polypeptide according to claim 1 dispered in a pharmaceutical buffer, diluent or medium.

13. The polypeptide of claim 1 dispersed in a cosmetic diluent, carrier or excipient.

14. A purified and isolated polypeptide comprising the sequence as depicted in SEQ ID NO:15, 18, 20 or 22.

* * * * *

UNITED STATES PATENT AND TRADEMARK OFFICE
CERTIFICATE OF CORRECTION

PATENT NO.       : 8,058,225 B2
APPLICATION NO.  : 12/194320
DATED            : November 15, 2011
INVENTOR(S)      : Michael Forchheim et al.

It is certified that error appears in the above-identified patent and that said Letters Patent is hereby corrected as shown below:

In claim 11, column 86, line 30, delete "in in" and insert --in-- therefor.

In claim 12, column 86, line 32, delete "dispered" and insert --dispersed-- therefor.

Signed and Sealed this
Sixth Day of March, 2012

David J. Kappos
*Director of the United States Patent and Trademark Office*

SEQUENCE LISTING

<160> NUMBER OF SEQ ID NOS: 28

<210> SEQ ID NO 1
<211> LENGTH: 490
<212> TYPE: PRT
<213> ORGANISM: unknown
<220> FEATURE:
<223> OTHER INFORMATION: pitti26

<400> SEQUENCE: 1

Met Ser Ile Ile Met Glu Val Ala Thr Met Gln Ala Lys Leu Thr Lys
1               5                   10                  15

Lys Glu Phe Ile Glu Trp Leu Lys Thr Ser Glu Gly Lys Gln Phe Asn
                20                  25                  30

Val Asp Leu Trp Tyr Gly Phe Gln Cys Phe Asp Tyr Ala Asn Ala Gly
            35                  40                  45

Trp Lys Val Leu Phe Gly Leu Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Arg Ile Glu Gln Pro Gly Trp Gly Trp Glu Lys Val Thr Arg
    130                 135                 140

Arg Gln His Ala Tyr Asp Phe Pro Met Trp Phe Ile Arg Pro Asn Phe
145                 150                 155                 160

Lys Ser Glu Thr Ala Pro Arg Ser Ile Gln Ser Pro Thr Gln Ala Ser
                165                 170                 175

Lys Lys Glu Thr Ala Lys Pro Gln Pro Lys Ala Val Glu Leu Lys Ile
            180                 185                 190

Ile Lys Asp Val Val Lys Gly Tyr Asp Leu Pro Lys Arg Gly Gly Asn
        195                 200                 205

Pro Lys Gly Ile Val Ile His Asn Asp Ala Gly Ser Lys Gly Ala Thr
    210                 215                 220

Ala Glu Ala Tyr Arg Asn Gly Leu Val Asn Ala Pro Ser Ser Arg Leu
225                 230                 235                 240

Glu Ala Gly Ile Ala His Ser Tyr Val Ser Gly Asn Thr Val Trp Gln
                245                 250                 255

Ala Leu Asp Glu Ser Gln Val Gly Trp His Thr Ala Asn Gln Leu Gly
            260                 265                 270

Asn Lys Tyr Tyr Tyr Gly Ile Glu Val Cys Gln Ser Met Gly Ala Asp
        275                 280                 285

Asn Ala Thr Phe Leu Lys Asn Glu Gln Ala Thr Phe Gln Glu Cys Ala
    290                 295                 300

Arg Leu Leu Lys Lys Trp Gly Leu Pro Ala Asn Arg Asn Thr Ile Arg
305                 310                 315                 320

Leu His Asn Glu Phe Thr Ser Thr Ser Cys Pro His Arg Ser Ser Val
                325                 330                 335

Leu His Thr Gly Phe Asp Pro Val Thr Arg Gly Leu Leu Pro Glu Asp
            340                 345                 350

Lys Arg Leu Gln Leu Lys Asp Tyr Phe Ile Lys Gln Ile Arg Ala Tyr
        355                 360                 365

Met Asp Gly Lys Ile Pro Val Ala Thr Val Ser Asn Glu Ser Ser Ala
    370                 375                 380

Ser Ser Asn Thr Val Lys Pro Val Ala Ser Ala Trp Lys Arg Asn Lys
385                 390                 395                 400

Tyr Gly Thr Tyr Tyr Met Glu Glu Ser Ala Arg Phe Thr Asn Gly Asn
                405                 410                 415

Gln Pro Ile Thr Val Arg Lys Ile Gly Pro Phe Leu Ser Cys Pro Val
            420                 425                 430

Ala Tyr Gln Phe Gln Pro Gly Gly Tyr Cys Asp Tyr Thr Glu Val Met
        435                 440                 445

Leu Gln Asp Gly His Val Trp Val Gly Tyr Thr Trp Glu Gly Gln Arg
    450                 455                 460

Tyr Tyr Leu Pro Ile Arg Thr Trp Asn Gly Ser Ala Pro Pro Asn Gln
465                 470                 475                 480

Ile Leu Gly Asp Leu Trp Gly Glu Ile Ser
            485                 490

<210> SEQ ID NO 2
<211> LENGTH: 1473
<212> TYPE: DNA
<213> ORGANISM: unknown
<220> FEATURE:
<223> OTHER INFORMATION: pitti26
<220> FEATURE:
<221> NAME/KEY: misc_feature
<222> LOCATION: (1221)..(1221)
<223> OTHER INFORMATION: n is a, c, g, or t

<400> SEQUENCE: 2
atgagtatca tcatggaggt ggcgacaatg caagcaaaat taactaaaaa agagtttata      60
gagtggttga aaacttctga gggaaaacaa ttcaatgtgg acttatggta tggatttcaa     120
tgctttgatt atgccaatgc tggttggaaa gttttgtttg gattacttct gaaaggttta     180
ggtgcaaaag atataccatt tgcaaacaat ttcgatggac tagctactgt ataccaaaat     240
acaccggact ttttggcaca acccggcgac atggttgtat cggtagcaa ttacggtgca      300
ggatacggac acgtagcatg ggtaattgaa gcaactttag attatatcat tgtatatgag     360
cagaattggc taggcggtgg ctggactgac agaatcgaac aacccggctg gggttgggaa     420
aaagttacaa gacgacaaca tgcttacgat ttccctatgt ggtttatccg tcctaacttc     480
aaaagcgaaa cagctccacg atcaatacaa tctcctacgc aagcatctaa aaaggaaaca     540
gctaagccac aacctaaagc ggtagaactt aaaattatca aagatgtggt taaaggttat     600
gaccttccta acgtggtgg taatcctaag ggtatagtta ttcataacga cgcaggaagc      660
aaaggggcaa cagcagaagc gtatcgaaac ggattagtta acgcaccttc atcaagatta     720
gaagcgggta ttgcgcatag ttatgtatca ggtaacacag tgtggcaagc tttagatgaa     780
tcgcaagtag gttggcatac tgctaaccaa ttaggcaata atattatta cggtattgaa      840
gtgtgtcaat caatgggagc ggataatgcg acgttttta aaaatgaaca ggcgactttc      900
caagaatgcg ctagattgtt gaaaaaatgg ggattaccag caaacagaaa tacaatcaga     960
ttacacaacg aattcacttc aacatcatgc ccacacagaa gctcagtatt gcacactggt    1020
tttgacccag taactcgcgg tctattgcca gaagacaagc ggttgcaact taaagactac    1080
tttatcaagc agattagggc gtacatggat ggtaaaatac cggttgccac tgtctctaat    1140
gagtcaagcg cttcaagtaa tacagttaaa ccagttgcaa gtgcatggaa acgtaataaa    1200

```
tatggtactt actacatgga ngaaagtgct agattcacaa acggtaatca accaatcact    1260
gtaagaaaaa taggaccatt cttatcatgc ccggtagctt accaattcca acctggtgga    1320
tattgtgatt atacagaagt gatgttacaa gatggtcatg tttgggtagg atatacatgg    1380 gagggcaac gttattactt gcctattaga acatggaatg gttctgcccc acctaatcag    1440
atattaggtg acttatgggg agaaatcagt tag                                 1473

<210> SEQ ID NO 3
<211> LENGTH: 101
<212> TYPE: PRT
<213> ORGANISM: unknown
<220> FEATURE:
<223> OTHER INFORMATION: prophage SA2USA

<400> SEQUENCE: 3

Met Pro Pro Val Pro Ala Gly Tyr Thr Leu Asp Lys Asn Asn Val Pro
1               5                   10                  15

Tyr Lys Lys Glu Gln Gly Asn Tyr Thr Val Ala Asn Val Lys Gly Asn
                20                  25                  30

Asn Val Arg Asp Gly Tyr Ser Thr Asn Ser Arg Ile Thr Gly Val Leu
            35                  40                  45

Pro Asn Asn Thr Thr Ile Thr Tyr Asp Gly Ala Tyr Cys Ile Asn Gly
        50                  55                  60

Tyr Arg Trp Ile Thr Tyr Ile Ala Asn Ser Gly Gln Arg Arg Tyr Ile
65                  70                  75                  80

Ala Thr Gly Glu Val Asp Ile Ala Gly Asn Arg Ile Ser Ser Phe Gly
                85                  90                  95

Lys Phe Ser Ala Val
            100

<210> SEQ ID NO 4
<211> LENGTH: 303
<212> TYPE: DNA
<213> ORGANISM: unknown
<220> FEATURE:
<223> OTHER INFORMATION: prophage SA2USA

<400> SEQUENCE: 4
atgccaccag tgccagcagg ttatacactc gataagaata atgtccctta taaaaagaa     60 caaggcaatt acacagtagc taatgttaaa ggtaataatg taagagacgg ttattcaact   120
aattcaagaa ttcagggggt attacccaac aacacaacaa ttacgtatga cggtgcatat   180
tgtattaatg gttatagatg gattacttat attgctaata gtggacaacg tcgctatatt   240
gcgaccggag aggtagacat agcaggcaac cgaataagca gttttggtaa gtttagtgca   300
gtt                                                                 303

<210> SEQ ID NO 5
<211> LENGTH: 96
<212> TYPE: PRT
<213> ORGANISM: unknown
<220> FEATURE:
<223> OTHER INFORMATION: pitti20

<400> SEQUENCE: 5

Met Lys Arg Lys Lys Pro Lys Gly Trp Ser Glu Asn Pro Tyr Gly Thr
1               5                   10                  15

Tyr Tyr Lys Lys Val Asp Lys Thr Phe Ile Val Gly Ser Glu Lys Ile
                20                  25                  30
```

```
Glu Thr Arg Ile Gly Ser Pro Phe Leu Ser Ala Pro Ser Gly Gly His
        35                  40                  45

Val Thr Pro Asn Gln Lys Met Thr Phe Asp Tyr Leu Ala Gln Gln Asp
 50                  55                  60

Gly Tyr Glu Trp Gly Gln Leu Glu Asn Asn Arg Gly Gln Gln Glu Phe
 65                  70                  75                  80

Val Pro Ile Arg Pro Leu Ser Gln Lys Glu Tyr Trp Gly Ile Leu Lys
                 85                  90                  95

<210> SEQ ID NO 6
<211> LENGTH: 288
<212> TYPE: DNA
<213> ORGANISM: unknown
<220> FEATURE:
<223> OTHER INFORMATION: pitti20

<400> SEQUENCE: 6
atgaaacgta aaaacctaa aggttggagt gaaaatcctt atggtactta ctataaaaaa     60
gttgataaaa catttattgt aggttcagaa aaaattgaaa cacgaattgg ttcaccttc   120 ttatctgcac caagtggagg acacgtgaca ccaaatcaaa aatgacctt tgactattta   180 gcacaacaag atggttatga atggggacaa cttgaaaata atagaggaca acaagaattt   240
gtaccaatta gaccattaag tcaaaaagaa tattgggggta ttttaaaa              288

<210> SEQ ID NO 7
<211> LENGTH: 496
<212> TYPE: PRT
<213> ORGANISM: artificial sequence
<220> FEATURE:
<223> OTHER INFORMATION: Synthetic peptide

<400> SEQUENCE: 7

Met Ser Ile Ile Met Glu Val Ala Thr Met Gln Ala Lys Leu Thr Lys
 1               5                  10                  15

Lys Glu Phe Ile Glu Trp Leu Lys Thr Ser Glu Gly Lys Gln Phe Asn
             20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Lys Gly Leu Gly Ala Lys Asp
 50                  55                  60

Ile Pro Phe Ala Asn Asn Phe Asp Gly Leu Ala Thr Val Tyr Gln Asn
 65                  70                  75                  80

Thr Pro Asp Phe Leu Ala Gln Pro Gly Asp Met Val Val Phe Gly Ser
                 85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Arg Ile Glu Gln Pro Gly Trp Gly Trp Glu Lys Val Thr Arg
    130                 135                 140

Arg Gln His Ala Tyr Asp Phe Pro Met Trp Phe Ile Arg Pro Asn Phe
145                 150                 155                 160

Lys Ser Glu Thr Ala Pro Arg Ser Ile Gln Ser Pro Thr Gln Ala Ser
                165                 170                 175

Lys Lys Glu Thr Ala Lys Pro Gln Pro Lys Ala Val Glu Leu Lys Ile
            180                 185                 190

Ile Lys Asp Val Val Lys Gly Tyr Asp Leu Pro Lys Arg Gly Gly Asn
        195                 200                 205
```

Pro Lys Gly Ile Val Ile His Asn Asp Ala Gly Ser Lys Gly Ala Thr
    210                 215                 220

Ala Glu Ala Tyr Arg Asn Gly Leu Val Asn Ala Pro Ser Ser Arg Leu
225                 230                 235                 240

Glu Ala Gly Ile Ala His Ser Tyr Val Ser Gly Asn Thr Val Trp Gln
                245                 250                 255

Ala Leu Asp Glu Ser Gln Val Gly Trp His Thr Ala Asn Gln Leu Gly
            260                 265                 270

Asn Lys Tyr Tyr Tyr Gly Ile Glu Val Cys Gln Ser Met Gly Ala Asp
        275                 280                 285

Asn Ala Thr Phe Leu Lys Asn Glu Gln Ala Thr Phe Gln Glu Cys Ala
    290                 295                 300

Arg Leu Leu Lys Lys Trp Gly Leu Pro Ala Asn Arg Asn Thr Ile Arg
305                 310                 315                 320

Leu His Asn Glu Phe Thr Ser Thr Ser Cys Pro His Arg Ser Ser Val
                325                 330                 335

Leu His Thr Gly Phe Asp Pro Val Thr Arg Gly Leu Leu Pro Glu Asp
            340                 345                 350

Lys Arg Leu Gln Leu Lys Asp Tyr Phe Ile Lys Gln Ile Arg Ala Tyr
        355                 360                 365

Met Asp Gly Lys Ile Pro Val Ala Thr Val Ser Asn Glu Ser Ser Ala
    370                 375                 380

Ser Ser Asn Thr Val Lys Pro Val Ala Glu Leu Met Pro Pro Val Pro
385                 390                 395                 400

Ala Gly Tyr Thr Leu Asp Lys Asn Asn Val Pro Tyr Lys Lys Glu Gln
                405                 410                 415

Gly Asn Tyr Thr Val Ala Asn Val Lys Gly Asn Val Arg Asp Gly
            420                 425                 430

Tyr Ser Thr Asn Ser Arg Ile Thr Gly Val Leu Pro Asn Asn Thr Thr
        435                 440                 445

Ile Thr Tyr Asp Gly Ala Tyr Cys Ile Asn Gly Tyr Arg Trp Ile Thr
    450                 455                 460

Tyr Ile Ala Asn Ser Gly Gln Arg Arg Tyr Ile Ala Thr Gly Glu Val
465                 470                 475                 480

Asp Ile Ala Gly Asn Arg Ile Ser Ser Phe Gly Lys Phe Ser Ala Val
                485                 490                 495

<210> SEQ ID NO 8
<211> LENGTH: 1497
<212> TYPE: DNA
<213> ORGANISM: artificial sequence
<220> FEATURE:
<223> OTHER INFORMATION: Synthetic primer

<400> SEQUENCE: 8
atgagtatca tcatggaggt ggcgacaatg caagcaaaat taactaaaaa agagtttata      60
gagtggttga aacttctga gggaaaacaa ttcaatgtgg acttatggta tggatttcaa     120
tgctttgatt atgccaatgc tggttggaaa gttttgtttg gattacttct gaaaggttta     180
ggtgcaaaag ataccatt tgcaaacaat ttcgatggac tagctactgt ataccaaaat     240
acaccggact ttttggcaca acccggcgac atggttatat cggtagcaa ttacggtgca     300 ggatacggac acgtagcatg ggtaattgaa gcaactttag attatatcat tgtatatgag     360
cagaattggc taggcggtgg ctggactgac agaatcgaac aacccggctg gggttgggaa     420
aaagttacaa gacgacaaca tgcttacgat ttccctatgt ggtttatccg tcctaacttc     480

```
aaaagcgaaa cagctccacg atcaatacaa tctcctacgc aagcatctaa aaaggaaaca      540
gctaagccac aacctaaagc ggtagaactt aaaattatca aagatgtggt taaaggttat      600
gaccttccta acgtggtgg taatcctaag ggtatagtta ttcataacga cgcaggaagc       660 aaagggcaa cagcagaagc gtatcgaaac ggattagtta acgcaccttc atcaagatta       720
gaagcgggta ttgcgcatag ttatgtatca ggtaacacag tgtggcaagc tttagatgaa      780
tcgcaagtag gttggcatac tgctaaccaa ttaggcaata aatattatta cggtattgaa      840
gtgtgtcaat caatgggagc ggataatgcg acgtttttaa aaaatgaaca ggcgactttc      900
caagaatgcg ctagattgtt gaaaaaatgg ggattaccag caaacagaaa tacaatcaga      960
ttacacaacg aattcacttc aacatcatgc ccacacagaa gctcagtatt gcacactggt     1020
tttgacccag taactcgcgg tctattgcca gaagacaagc ggttgcaact taaagactac     1080
tttatcaagc agattagggc gtacatggat ggtaaaatac cggttgccac tgtctctaat     1140
gagtcaagcg cttcaagtaa tacagttaaa ccagttgcag agctcatgcc accagtgcca     1200
gcaggttata cactcgataa gaataatgtc ccttataaaa agaacaagg caattacaca      1260 gtagctaatg ttaaaggtaa aatgtaaga gacggttatt caactaattc aagaattaca     1320
ggggtattac ccaacaacac aacaattacg tatgacggtg catattgtat taatggttat      1380
agatggatta cttatattgc taatagtgga caacgtcgct atattgcgac cggagaggta      1440
gacatagcag gcaaccgaat aagcagtttt ggtaagttta gtgcagtttg ataataa          1497
```

<210> SEQ ID NO 9
<211> LENGTH: 506
<212> TYPE: PRT
<213> ORGANISM: artificial sequence
<220> FEATURE:
<223> OTHER INFORMATION: Synthetic peptide

<400> SEQUENCE: 9

Met Ser Ile Ile Met Glu Val Ala Thr Met Gln Ala Lys Leu Thr Lys
1               5                   10                  15

Lys Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Arg Ile Glu Gln Pro Gly Trp Gly Trp Glu Lys Val Thr Arg
    130                 135                 140

Arg Gln His Ala Tyr Asp Phe Pro Met Trp Phe Ile Arg Pro Asn Phe
145                 150                 155                 160

Lys Ser Glu Thr Ala Pro Arg Ser Ile Gln Ser Pro Thr Gln Ala Ser
                165                 170                 175

Lys Lys Glu Thr Ala Lys Pro Gln Pro Lys Ala Val Glu Leu Lys Ile
            180                 185                 190

Ile Lys Asp Val Val Lys Gly Tyr Asp Leu Pro Lys Arg Gly Gly Asn
        195                 200                 205

Pro Lys Gly Ile Val Ile His Asn Asp Ala Gly Ser Lys Gly Ala Thr
    210                 215                 220

Ala Glu Ala Tyr Arg Asn Gly Leu Val Asn Ala Pro Ser Ser Arg Leu
225                 230                 235                 240

Glu Ala Gly Ile Ala His Ser Tyr Val Ser Gly Asn Thr Val Trp Gln
                245                 250                 255

Ala Leu Asp Glu Ser Gln Val Gly Trp His Thr Ala Asn Gln Leu Gly
            260                 265                 270

Asn Lys Tyr Tyr Tyr Gly Ile Glu Val Cys Gln Ser Met Gly Ala Asp
        275                 280                 285

Asn Ala Thr Phe Leu Lys Asn Glu Gln Ala Thr Phe Gln Glu Cys Ala
    290                 295                 300

Arg Leu Leu Lys Lys Trp Gly Leu Pro Ala Asn Arg Asn Thr Ile Arg
305                 310                 315                 320

Leu His Asn Glu Phe Thr Ser Thr Ser Cys Pro His Arg Ser Ser Val
                325                 330                 335

Leu His Thr Gly Phe Asp Pro Val Thr Arg Gly Leu Leu Pro Glu Asp
            340                 345                 350

Lys Arg Leu Gln Leu Lys Asp Tyr Phe Ile Lys Gln Ile Arg Ala Tyr
        355                 360                 365

Met Asp Gly Lys Ile Pro Val Ala Thr Val Ser Asn Glu Ser Ser Ala
    370                 375                 380

Ser Ser Asn Thr Val Lys Pro Val Ala Glu Leu Met Pro Pro Val Pro
385                 390                 395                 400

Ala Gly Tyr Thr Leu Asp Lys Asn Asn Val Pro Tyr Lys Lys Glu Gln
                405                 410                 415

Gly Asn Tyr Thr Val Ala Asn Val Lys Gly Asn Asn Val Arg Asp Gly
            420                 425                 430

Tyr Ser Thr Asn Ser Arg Ile Thr Gly Val Leu Pro Asn Asn Thr Thr
        435                 440                 445

Ile Thr Tyr Asp Gly Ala Tyr Cys Ile Asn Gly Tyr Arg Trp Ile Thr
    450                 455                 460

Tyr Ile Ala Asn Ser Gly Gln Arg Arg Tyr Ile Ala Thr Gly Glu Val
465                 470                 475                 480

Asp Ile Ala Gly Asn Arg Ile Ser Ser Phe Gly Lys Phe Ser Ala Val
                485                 490                 495

Gly Ser Arg Ser His His His His His His
            500                 505

<210> SEQ ID NO 10
<211> LENGTH: 1521
<212> TYPE: DNA
<213> ORGANISM: artificial sequence
<220> FEATURE:
<223> OTHER INFORMATION: Synthetic primer

<400> SEQUENCE: 10
atgagtatca tcatggaggt ggcgacaatg caagcaaaat taactaaaaa agagtttata      60
gagtggttga aaacttctga gggaaaacaa ttcaatgtgg acttatggta tggatttcaa     120
tgctttgatt atgccaatgc tggttggaaa gttttgtttg gattacttct gaaaggttta     180
ggtgcaaaag atataccatt tgcaaacaat ttcgatggac tagctactgt ataccaaaat     240
acaccggact ttttggcaca acccggcgac atggttgtat tcggtagcaa ttacggtgca     300

```
ggatacggac acgtagcatg gtaattgaa gcaactttag attatatcat tgtatatgag    360
cagaattggc taggcggtgg ctggactgac agaatcgaac aacccggctg gggttgggaa    420
aaagttacaa gacgcaaca tgcttacgat ttccctatgt ggtttatccg tcctaacttc    480
aaaagcgaaa cagctccacg atcaatacaa tctcctacgc aagcatctaa aaaggaaaca    540
gctaagccac aacctaaagc ggtagaactt aaaattatca aagatgtggt taaaggttat    600
gaccttccta acgtggtgg taatcctaag ggtatagtta ttcataacga cgcaggaagc    660
aaaggggcaa cagcagaagc gtatcgaaac ggattagtta acgcaccttc atcaagatta    720
gaagcgggta ttgcgcatag ttatgtatca ggtaacacag tgtggcaagc tttagatgaa    780
tcgcaagtag gttggcatac tgctaaccaa ttaggcaata aatattatta cggtattgaa    840
gtgtgtcaat caatgggagc ggataatgcg acgttttta aaaatgaaca ggcgactttc    900
caagaatgcg ctagattgtt gaaaaaatgg ggattaccag caaacagaaa tacaatcaga    960
ttacacaacg aattcacttc aacatcatgc ccacacagaa gctcagtatt gcacactggt   1020
tttgacccag taactcgcgg tctattgcca gaagacaagc ggttgcaact taaagactac   1080
tttatcaagc agattagggc gtacatggat ggtaaaatac cggttgccac tgtctctaat   1140
gagtcaagcg cttcaagtaa tacagttaaa ccagttgcag agctcatgcc accagtgcca   1200
gcaggttata cactcgataa gaataatgtc ccttataaaa agaacaagg caattacaca   1260 gtagctaatg ttaaaggtaa taatgtaaga gacggttatt caactaattc aagaattaca   1320
ggggtattac ccaacaacac aacaattacg tatgacggtg catattgtat taatggttat   1380
agatggatta cttatattgc taatagtgga caacgtcgct atattgcgac cggagaggta   1440
gacatagcag gcaaccgaat aagcagtttt ggtaagttta gtgcagttgg atccagatct   1500
catcaccatc accatcacta a                                             1521

<210> SEQ ID NO 11
<211> LENGTH: 491
<212> TYPE: PRT
<213> ORGANISM: artificial sequence
<220> FEATURE:
<223> OTHER INFORMATION: Synthetic peptide

<400> SEQUENCE: 11

Met Ser Ile Ile Met Glu Val Ala Thr Met Gln Ala Lys Leu Thr Lys
1               5                   10                  15

Lys Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Trp
        115                 120                 125

Thr Asp Arg Ile Glu Gln Pro Gly Trp Gly Trp Glu Lys Val Thr Arg
    130                 135                 140
```

Arg Gln His Ala Tyr Asp Phe Pro Met Trp Phe Ile Arg Pro Asn Phe
145                 150                 155                 160

Lys Ser Glu Thr Ala Pro Arg Ser Ile Gln Ser Pro Thr Gln Ala Ser
            165                 170                 175

Lys Lys Glu Thr Ala Lys Pro Gln Pro Lys Ala Val Glu Leu Lys Ile
            180                 185                 190

Ile Lys Asp Val Val Lys Gly Tyr Asp Leu Pro Lys Arg Gly Gly Asn
            195                 200                 205

Pro Lys Gly Ile Val Ile His Asn Asp Ala Gly Ser Lys Gly Ala Thr
210                 215                 220

Ala Glu Ala Tyr Arg Asn Gly Leu Val Asn Ala Pro Ser Ser Arg Leu
225                 230                 235                 240

Glu Ala Gly Ile Ala His Ser Tyr Val Ser Gly Asn Thr Val Trp Gln
            245                 250                 255

Ala Leu Asp Glu Ser Gln Val Gly Trp His Thr Ala Asn Gln Leu Gly
            260                 265                 270

Asn Lys Tyr Tyr Tyr Gly Ile Glu Val Cys Gln Ser Met Gly Ala Asp
            275                 280                 285

Asn Ala Thr Phe Leu Lys Asn Glu Gln Ala Thr Phe Gln Glu Cys Ala
290                 295                 300

Arg Leu Leu Lys Lys Trp Gly Leu Pro Ala Asn Arg Asn Thr Ile Arg
305                 310                 315                 320

Leu His Asn Glu Phe Thr Ser Thr Ser Cys Pro His Arg Ser Ser Val
            325                 330                 335

Leu His Thr Gly Phe Asp Pro Val Thr Arg Gly Leu Leu Pro Glu Asp
            340                 345                 350

Lys Arg Leu Gln Leu Lys Asp Tyr Phe Ile Lys Gln Ile Arg Ala Tyr
            355                 360                 365

Met Asp Gly Lys Ile Pro Val Ala Thr Val Ser Asn Glu Ser Ser Ala
            370                 375                 380

Ser Ser Asn Thr Val Lys Pro Val Ala Glu Leu Met Lys Arg Lys Lys
385                 390                 395                 400

Pro Lys Gly Trp Ser Glu Asn Pro Tyr Gly Thr Tyr Tyr Lys Lys Val
            405                 410                 415

Asp Lys Thr Phe Ile Val Gly Ser Glu Lys Ile Glu Thr Arg Ile Gly
            420                 425                 430

Ser Pro Phe Leu Ser Ala Pro Ser Gly Gly His Val Thr Pro Asn Gln
            435                 440                 445

Lys Met Thr Phe Asp Tyr Leu Ala Gln Gln Asp Gly Tyr Glu Trp Gly
            450                 455                 460

Gln Leu Glu Asn Asn Arg Gly Gln Gln Glu Phe Val Pro Ile Arg Pro
465                 470                 475                 480

Leu Ser Gln Lys Glu Tyr Trp Gly Ile Leu Lys
            485                 490

<210> SEQ ID NO 12
<211> LENGTH: 1476
<212> TYPE: DNA
<213> ORGANISM: artificial sequence
<220> FEATURE:
<223> OTHER INFORMATION: Synthetic primer

<400> SEQUENCE: 12
atgagtatca tcatggaggt ggcgacaatg caagcaaaat taactaaaaa agagtttata    60
gagtggttga aaacttctga gggaaaacaa ttcaatgtgg acttatggta tggatttcaa   120

```
tgctttgatt atgccaatgc tggttggaaa gttttgtttg gattacttct gaaaggttta    180
ggtgcaaaag atataccatt tgcaaacaat ttcgatggac tagctactgt ataccaaaat    240
acaccggact ttttggcaca acccggcgac atggttgtat tcggtagcaa ttacggtgca    300
ggatacggac acgtagcatg gtaattgaa gcaactttag attatatcat tgtatatgag    360
cagaattggc taggcggtgg ctggactgac agaatcgaac aacccggctg gggttgggaa    420
aaagttacaa gacgcaaaca tgcttacgat ttccctatgt ggtttatccg tcctaacttc    480
aaaagcgaaa cagctccacg atcaatacaa tctcctacgc aagcatctaa aaggaaaca    540 gctaagccac aacctaaagc ggtagaactt aaaattatca agatgtggt taaaggttat    600 gaccttccta acgtggtgg taatcctaag ggtatagtta ttcataacga cgcaggaagc    660
aaaggggcaa cagcagaagc gtatcgaaac ggattagtta acgcaccttc atcaagatta    720
gaagcgggta ttgcgcatag ttatgtatca ggtaacacag tgtggcaagc tttagatgaa    780
tcgcaagtag gttggcatac tgctaaccaa ttaggcaata atattatta cggtattgaa    840 gtgtgtcaat caatgggagc ggataatgcg acgttttaa aaaatgaaca ggcgactttc    900
caagaatgcg ctagattgtt gaaaaaatgg ggattaccag caaacagaaa tacaatcaga    960
ttacacaacg aattcacttc aacatcatgc ccacacagaa gctcagtatt gcacactggt   1020
tttgacccag taactcgcgg tctattgcca gaagacaagc ggttgcaact taaagactac   1080
tttatcaagc agattagggc gtacatggat ggtaaaatac cggttgccac tgtctctaat   1140
gagtcaagcg cttcaagtaa tacagttaaa ccagttgcag agctcatgaa acgtaaaaaa   1200
cctaaaggtt ggagtgaaaa tccttatggt acttactata aaaagttga taaaacattt   1260 attgtaggtt cagaaaaaat tgaaacacga attggttcac ctttcttatc tgcaccaagt   1320
ggaggacacg tgacaccaaa tcaaaaaatg acctttgact atttagcaca acaagatggt   1380
tatgaatggg gacaacttga aaataataga ggacaacaag aatttgtacc aattagacca   1440
ttaagtcaaa aagaatattg gggtatttta aaatag                              1476
```

<210> SEQ ID NO 13
<211> LENGTH: 501
<212> TYPE: PRT
<213> ORGANISM: artificial sequence
<220> FEATURE:
<223> OTHER INFORMATION: Synthetic peptide

<400> SEQUENCE: 13

```
Met Ser Ile Ile Met Glu Val Ala Thr Met Gln Ala Lys Leu Thr Lys
1               5                   10                  15

Lys Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125
```

Thr Asp Arg Ile Glu Gln Pro Gly Trp Gly Trp Glu Lys Val Thr Arg
130                 135                 140

Arg Gln His Ala Tyr Asp Phe Pro Met Trp Phe Ile Arg Pro Asn Phe
145                 150                 155                 160

Lys Ser Glu Thr Ala Pro Arg Ser Ile Gln Ser Pro Thr Gln Ala Ser
                165                 170                 175

Lys Lys Glu Thr Ala Lys Pro Gln Pro Lys Ala Val Glu Leu Lys Ile
                180                 185                 190

Ile Lys Asp Val Val Lys Gly Tyr Asp Leu Pro Lys Arg Gly Gly Asn
            195                 200                 205

Pro Lys Gly Ile Val Ile His Asn Asp Ala Gly Ser Lys Gly Ala Thr
210                 215                 220

Ala Glu Ala Tyr Arg Asn Gly Leu Val Asn Ala Pro Ser Ser Arg Leu
225                 230                 235                 240

Glu Ala Gly Ile Ala His Ser Tyr Val Ser Gly Asn Thr Val Trp Gln
                245                 250                 255

Ala Leu Asp Glu Ser Gln Val Gly Trp His Thr Ala Asn Gln Leu Gly
                260                 265                 270

Asn Lys Tyr Tyr Tyr Gly Ile Glu Val Cys Gln Ser Met Gly Ala Asp
            275                 280                 285

Asn Ala Thr Phe Leu Lys Asn Glu Gln Ala Thr Phe Gln Glu Cys Ala
290                 295                 300

Arg Leu Leu Lys Lys Trp Gly Leu Pro Ala Asn Arg Asn Thr Ile Arg
305                 310                 315                 320

Leu His Asn Glu Phe Thr Ser Thr Ser Cys Pro His Arg Ser Ser Val
                325                 330                 335

Leu His Thr Gly Phe Asp Pro Val Thr Arg Gly Leu Leu Pro Glu Asp
                340                 345                 350

Lys Arg Leu Gln Leu Lys Asp Tyr Phe Ile Lys Gln Ile Arg Ala Tyr
            355                 360                 365

Met Asp Gly Lys Ile Pro Val Ala Thr Val Ser Asn Glu Ser Ser Ala
370                 375                 380

Ser Ser Asn Thr Val Lys Pro Val Ala Glu Leu Met Lys Arg Lys Lys
385                 390                 395                 400

Pro Lys Gly Trp Ser Glu Asn Pro Tyr Gly Thr Tyr Lys Lys Val
                405                 410                 415

Asp Lys Thr Phe Ile Val Gly Ser Glu Lys Ile Glu Thr Arg Ile Gly
                420                 425                 430

Ser Pro Phe Leu Ser Ala Pro Ser Gly Gly His Val Thr Pro Asn Gln
            435                 440                 445

Lys Met Thr Phe Asp Tyr Leu Ala Gln Gln Asp Gly Tyr Glu Trp Gly
450                 455                 460

Gln Leu Glu Asn Asn Arg Gly Gln Gln Glu Phe Val Pro Ile Arg Pro
465                 470                 475                 480

Leu Ser Gln Lys Glu Tyr Trp Gly Ile Leu Lys Gly Ser Arg Ser His
                485                 490                 495

His His His His
        500

<210> SEQ ID NO 14
<211> LENGTH: 1506
<212> TYPE: DNA
<213> ORGANISM: artificial sequence
<220> FEATURE:
<223> OTHER INFORMATION: Synthetic primer -continued

```
<400> SEQUENCE: 14
atgagtatca tcatggaggt ggcgacaatg caagcaaaat taactaaaaa agagtttata      60
gagtggttga aaacttctga gggaaaacaa ttcaatgtgg acttatggta tggatttcaa     120
tgctttgatt atgccaatgc tggttggaaa gttttgtttg gattacttct gaaaggttta     180
ggtgcaaaag atataccatt tgcaaacaat tcgatggac tagctactgt ataccaaaat      240
acaccggact ttttggcaca acccggcgac atggttgtat cggtagcaa ttacggtgca      300 ggatacggac acgtagcatg ggtaattgaa gcaactttag attatatcat tgtatatgag     360
cagaattggc taggcggtgg ctggactgac agaatcgaac aacccggctg gggttgggaa     420
aaagttacaa gacgacaaca tgcttacgat ttccctatgt ggtttatccg tcctaacttc     480
aaaagcgaaa cagctccacg atcaatacaa tctcctacgc aagcatctaa aaaggaaaca     540
gctaagccac aacctaaagc ggtagaactt aaaattatca agatgtggt taaaggttat       600 gaccttccta acgtggtgg taatcctaag ggtatagtta ttcataacga cgcaggaagc      660 aaagggcaa cagcagaagc gtatcgaaac ggattagtta acgcaccttc atcaagatta      720
gaagcgggta ttgcgcatag ttatgtatca ggtaacacag tgtggcaagc tttagatgaa     780
tcgcaagtag gttggcatac tgctaaccaa ttaggcaata aatattatta cggtattgaa     840
gtgtgtcaat caatgggagc ggataatgcg acgttttaa aaaatgaaca ggcgactttc       900
caagaatgcg ctagattgtt gaaaaaatgg ggattaccag caaacagaaa tacaatcaga     960
ttacacaacg aattcacttc aacatcatgc ccacacagaa gctcagtatt gcacactggt    1020
tttgacccag taactcgcgg tctattgcca gaagacaagc ggttgcaact taaagactac    1080
tttatcaagc agattagggc gtacatggat ggtaaaatac cggttgccac tgtctctaat    1140
gagtcaagcg cttcaagtaa tacagttaaa ccagttgcag agctcatgaa acgtaaaaaa    1200
cctaaaggtt ggagtgaaaa tccttatggt acttactata aaaagttga taaaacattt       1260 attgtaggtt cagaaaaaat tgaaacacga attggttcac ctttcttatc tgcaccaagt    1320
ggaggacacg tgacaccaaa tcaaaaaatg acctttgact atttagcaca acaagatggt    1380
tatgaatggg acaacttga aataatcaga ggacaacaag aatttgtacc aattagacca      1440
ttaagtcaaa aagaatattg gggtatttta aaaggatcca gatctcatca ccatcaccat    1500
cactaa                                                               1506
```

<210> SEQ ID NO 15
<211> LENGTH: 497
<212> TYPE: PRT
<213> ORGANISM: artificial sequence
<220> FEATURE:
<223> OTHER INFORMATION: Synthetic peptide

<400> SEQUENCE: 15

Met Ala Ser Ile Ile Met Glu Val Ala Thr Met Gln Ala Lys Leu Thr
1               5                   10                  15

Lys Lys Glu Phe Ile Glu Trp Leu Lys Thr Ser Glu Gly Lys Gln Phe
            20                  25                  30

Asn Val Asp Leu Trp Tyr Gly Phe Gln Cys Phe Asp Tyr Ala Asn Ala
        35                  40                  45

Gly Trp Lys Val Leu Phe Gly His Thr Leu Lys Gly Leu Gly Ala Lys
    50                  55                  60

Asp Ile Pro Phe Ala Asn Asn Phe Asp Gly Leu Ala Thr Val Tyr Gln
65                  70                  75                  80

Asn Thr Pro Asp Phe Leu Ala Gln Pro Gly Asp Met Val Val Phe Gly

```
                        85                  90                  95
Ser Asn Tyr Gly Ala Gly Tyr Gly His Val Ala Trp Val Ile Glu Ala
                100                 105                 110
Thr Leu Asp Tyr Ile Ile Val Tyr Glu Gln Asn Trp Leu Gly Gly Gly
                115                 120                 125
Trp Thr Asp Arg Ile Glu Gln Pro Gly Trp Gly Trp Glu Lys Val Thr
130             135                 140
Arg Arg Gln His Ala Tyr Asp Phe Pro Met Trp Phe Ile Arg Pro Asn
145                 150                 155                 160
Phe Lys Ser Ala Thr Ala Pro Ala Ser Ile Gln Ser Pro Thr Gln Ala
                165                 170                 175
Ser Lys Lys Glu Thr Ala Lys Pro Gln Pro Lys Ala Val Glu Leu Lys
                180                 185                 190
Ile Ile Lys Asp Val Val Lys Gly His Asp Leu Pro Lys Arg Gly Gly
                195                 200                 205
Asn Pro Lys Gly Ile Val Ile His Asn Asp Ala Gly Ser Lys Gly Ala
                210                 215                 220
Thr Ala Glu Ala Tyr Arg Asn Gly Leu Val Asn Ala Pro Ser Ser Arg
225                 230                 235                 240
Leu Glu Ala Gly Ile Ala His Ser Tyr Val Ser Gly Asn Thr Val Trp
                245                 250                 255
Gln Ala Leu Asp Glu Ser Gln Val Gly Trp His Thr Ala Asn Gln Leu
                260                 265                 270
Gly Asn Lys Tyr Tyr Tyr Gly Ile Glu Val Cys Gln Ser Met Gly Ala
                275                 280                 285
Asp Asn Ala Thr Phe Leu Lys Asn Glu Gln Ala Thr Phe Gln Glu Cys
                290                 295                 300
Ala Arg Leu Leu Lys Lys Trp Gly Leu Pro Ala Asn Arg Asn Thr Ile
305                 310                 315                 320
Arg Leu His Asn Glu Phe Thr Ser Thr Ser Cys Pro His Arg Ser Ser
                325                 330                 335
Val Leu His Thr Gly Phe Asp Pro Val Thr Arg Gly Leu Leu Pro Glu
                340                 345                 350
Asp Lys Arg Leu Gln Leu Lys Asp Tyr Phe Ile Lys Gln Ile Arg Ala
                355                 360                 365
Tyr Met Asp Gly Lys Ile Pro Val Ala Thr Val Ser Asn Glu Ser Ser
                370                 375                 380
Ala Ser Ser Asn Thr Val Lys Pro Val Ala Glu Leu Met Pro Pro Val
385                 390                 395                 400
Pro Ala Gly Tyr Thr Leu Asp Lys Asn Asn Val Pro Tyr Lys Lys Glu
                405                 410                 415
Gln Gly Asn Tyr Thr Val Ala Asn Val Lys Gly Asn Asn Val Arg Asp
                420                 425                 430
Gly Tyr Ser Thr Asn Ser Arg Ile Thr Gly Val Leu Pro Asn Asn Thr
                435                 440                 445
Thr Ile Thr Tyr Asp Gly Ala Tyr Cys Ile Asn Gly Tyr Arg Trp Ile
                450                 455                 460
Thr Tyr Ile Ala Asn Ser Gly Gln Arg Arg Tyr Ile Ala Thr Gly Glu
465                 470                 475                 480
Val Asp Ile Ala Gly Asn Arg Ile Ser Ser Phe Gly Lys Phe Ser Ala
                485                 490                 495
Val
```

```
<210> SEQ ID NO 16
<211> LENGTH: 1491
<212> TYPE: DNA
<213> ORGANISM: artificial sequence
<220> FEATURE:
<223> OTHER INFORMATION: Synthetic primer

<400> SEQUENCE: 16
atggcaagta tcatcatgga ggtggcgaca atgcaagcaa aattaactaa aaaagagttt      60
atagagtggt tgaaaacttc tgagggaaaa caattcaatg tggacttatg gtatggattt     120
caatgctttg attatgccaa tgctggttgg aaagttttgt ttggacatac actgaaaggt     180
ttaggtgcaa aagatatacc atttgcaaac aatttcgatg gactagctac tgtataccaa     240
aatacaccgg acttttttggc acaacccggc gacatggttg tattcggtag caattacggt     300
gcaggatacg gacacgtagc atgggtaatt gaagcaactt tagattatat cattgtatat     360
gagcagaatt ggctaggcgg tggctggact gacagaatcg aacaacccgg ctggggttgg     420 gaaaagtta caagacgaca acatgcttac gatttcccta tgtggtttat ccgtcctaac     480
ttcaaaagcg ctacagctcc agcttcaata caatctccta cgcaagcatc taaaaaggaa     540
acagctaagc cacaacctaa agcggtagaa cttaaaatta tcaaagatgt ggttaaaggt     600
catgaccttc ctaaacgtgg tggtaatcct aagggtatag ttattcataa cgacgcagga     660
agcaaagggg caacagcaga agcgtatcga acggattag ttaacgcacc ttcatcaaga     720
ttagaagcgg gtattgcgca tagttatgta tcaggtaaca cagtgtggca agctttagat     780
gaatcgcaag taggttggca tactgctaac caattaggca ataaatatta ttacggtatt     840
gaagtgtgtc aatcaatggg agcggataat gcgacgtttt taaaaaatga acaggcgact     900
ttccaagaat gcgctagatt gttgaaaaaa tggggattac cagcaaacag aaatacaatc     960
agattacaca acgaattcac ttcaacatca tgcccacaca gaagctcagt attgcacact    1020
ggttttgacc cagtaactcg cggtctattg ccagaagaca gcggttgca acttaaagac    1080 tactttatca agcagattag ggcgtacatg gatggtaaaa taccggttgc cactgtctct    1140
aatgagtcaa gcgcttcaag taatacagtt aaaccagttg cagagctcat gccaccagtg    1200
ccagcaggtt atacactcga taagaataat gtcccttata aaaaagaaca aggcaattac    1260
acagtagcta atgttaaagg taataatgta agagacggtt attcaactaa ttcaagaatt    1320
acaggggtat tacccaacaa cacaacaatt acgtatgacg gtgcatattg tattaatggt    1380
tatagatgga ttacttatat tgctaatagt ggacaacgtc gctatattgc gaccggagag    1440
gtagacatag caggcaaccg aataagcagt tttggtaagt ttagtgcagt t             1491

<210> SEQ ID NO 17
<211> LENGTH: 1491
<212> TYPE: DNA
<213> ORGANISM: artificial sequence
<220> FEATURE:
<223> OTHER INFORMATION: Synthetic primer

<400> SEQUENCE: 17
atggcgtcta ttattatgga agtggcgacc atgcaggcga aactgaccaa aaaagaattc      60
atcgaatggc tgaaaaccag cgaaggcaaa cagtttaacg tggatctgtg gtatggcttt     120
cagtgctttg attatgcgaa cgcgggctgg aaagtgctgt ttggccatac cctgaaaggc     180
ctgggcgcga agatattcc gtttgcgaat aactttgatg gcctggccac cgtgtatcag     240 aacacccccgg attttctggc ccagccgggc gatatggtgg tgtttggcag caactatggc     300
gcgggttatg gccatgtggc gtgggtgatt gaagcgaccc tggattatat catcgtgtac     360
```

```
gaacagaact ggctgggcgg tggctggacc gatcgtattg aacagccggg ctggggctgg    420
gaaaaagtga cccgtcgtca gcatgcgtac gatttccga tgtggtttat tcgcccgaac    480
tttaaatctg cgacggcccc ggcgagcatt cagagcccga cccaggcgag caaaaaagaa    540
accgcgaaac cgcagccgaa agcggtggaa ctgaaaatca tcaagatgt ggtgaaaggc    600 catgatctgc cgaaacgtgg cggcaatccg aaaggcattg tgattcataa cgatgcgggc    660
agcaaaggtg cgaccgcgga agcgtatcgt aacggcctgg tgaacgcgcc gagcagccgt    720
ctggaagcgg gcattgcgca tagctatgtg agcggcaaca ccgtgtggca ggcgctggat    780
gaaagccagg tgggctggca taccgcgaac cagctgggca caaatatta ttacggcatc    840 gaagtgtgcc agagcatggg cgcggataac gcgacctttc tgaaaaacga acaggcgacc    900
tttcaggaat gcgcgcgtct gctgaaaaaa tggggcctgc cggcgaaccg taacaccatt    960
cgtctgcata cgaatttac cagcaccagc tgcccgcatc gtagcagcgt gctgcatacc    1020
ggctttgatc cggtgacccg tggcctgctg ccggaagata acgtctgca gctgaaagat    1080 tatttcatca acaaatccg cgcgtatatg gatggcaaaa ttccggtggc gaccgtgagc    1140
aacgaaagca gcgcgagcag caataccgtg aaaccggtgg cggaactgat gccgccggtt    1200
ccggccggtt ataccctgga taaaaacaac gtgccgtata aaaagaaca gggcaactat    1260 accgtggcga acgtgaaagg caacaacgtg cgtgatggct atagcaccaa cagccgtatt    1320
accggcgtgc tgccgaacaa caccaccatt acctatgatg cgcgtattg cattaacggc    1380 tatcgctgga ttacctatat cgcgaacagc ggccagcgtc gttatattgc gaccggcgaa    1440
gtggatattg cggcaaccg tattagcagc tttggtaaat ttagcgcggt g              1491

<210> SEQ ID NO 18
<211> LENGTH: 497
<212> TYPE: PRT
<213> ORGANISM: artificial sequence
<220> FEATURE:
<223> OTHER INFORMATION: Synthetic peptide

<400> SEQUENCE: 18

Met Ala Ser Ile Ile Met Glu Val Ala Thr Met Gln Ala Lys Leu Thr
1               5                  10                  15

Lys Lys Glu Phe Ile Glu Trp Leu Lys Thr Ser Glu Gly Lys Gln Phe
            20                  25                  30

Asn Val Asp Leu Trp Tyr Gly Phe Gln Cys Phe Asp Tyr Ala Asn Ala
        35                  40                  45

Gly Trp Lys Val Leu Phe Gly His Thr Leu Lys Gly Leu Gly Ala Lys
    50                  55                  60

Asp Ile Pro Phe Ala Asn Asn Phe Asp Gly Leu Ala Thr Val Tyr Gln
65                  70                  75                  80

Asn Thr Pro Asp Phe Leu Ala Gln Pro Gly Asp Met Val Val Phe Gly
                85                  90                  95

Ser Asn Tyr Gly Ala Gly Tyr Gly His Val Ala Trp Val Ile Glu Ala
            100                 105                 110

Thr Leu Asp Tyr Ile Ile Val Tyr Glu Gln Asn Trp Leu Gly Gly Gly
        115                 120                 125

Trp Thr Asp Arg Ile Glu Gln Pro Gly Trp Gly Trp Glu Lys Val Thr
    130                 135                 140

Arg Arg Gln His Ala Tyr Asp Phe Pro Met Trp Phe Ile Arg Pro Asn
145                 150                 155                 160

Phe Lys Ser Ala Thr Ala Pro Ala Ser Ile Gln Ser Pro Thr Gln Ala
```

Ser Lys Lys Glu Thr Ala Lys Pro Gln Pro Lys Ala Val Glu Leu Lys
165                 170                 175

Ile Ile Lys Asp Val Val Lys Gly His Asp Leu Pro Lys Arg Gly Gly
        180                 185                 190

Asn Pro Lys Gly Ile Val Ile His Asn Asp Ala Gly Ser Lys Gly Ala
    195                 200                 205

Thr Ala Glu Ala Tyr Arg Asn Gly Leu Val Asn Ala Pro Leu Ser Arg
210                 215                 220

Leu Glu Ala Gly Ile Ala His Ser Tyr Val Ser Gly Asn Thr Val Trp
225                 230                 235                 240

Gln Ala Leu Asp Glu Ser Gln Val Gly Trp His Thr Ala Asn Gln Leu
        245                 250                 255

Gly Asn Lys Tyr Tyr Tyr Gly Ile Glu Val Cys Gln Ser Met Gly Ala
    260                 265                 270

Asp Asn Ala Thr Phe Leu Lys Asn Glu Gln Ala Thr Phe Gln Glu Cys
275                 280                 285

Ala Arg Leu Leu Lys Lys Trp Gly Leu Pro Ala Asn Arg Asn Thr Ile
290                 295                 300

Arg Leu His Asn Glu Phe Thr Ser Thr Ser Cys Pro His Arg Ser Ser
305                 310                 315                 320

Val Leu His Thr Gly Phe Asp Pro Thr Arg Gly Leu Leu Pro Glu
        325                 330                 335

Asp Lys Gln Leu Gln Leu Lys Asp Tyr Phe Ile Lys Gln Ile Arg Val
    340                 345                 350

Tyr Met Asp Gly Lys Ile Pro Val Ala Thr Val Ser Asn Glu Ser Ser
355                 360                 365

Ala Ser Ser Asn Thr Val Lys Pro Val Ala Glu Leu Met Pro Pro Val
370                 375                 380

Pro Ala Gly Tyr Thr Leu Asp Lys Asn Asn Val Pro Tyr Lys Lys Glu
385                 390                 395                 400

Gln Gly Asn Tyr Thr Val Ala Asn Val Lys Gly Asn Asn Val Arg Asp
        405                 410                 415

Gly Tyr Ser Thr Asn Ser Arg Ile Thr Gly Val Leu Pro Asn Asn Thr
    420                 425                 430

Thr Ile Thr Tyr Asp Gly Ala Tyr Cys Ile Asn Gly Tyr Arg Trp Ile
435                 440                 445

Thr Tyr Ile Ala Asn Ser Gly Gln Arg Arg Tyr Ile Ala Thr Gly Glu
450                 455                 460

Val Asp Ile Ala Gly Asn Arg Ile Ser Ser Phe Gly Lys Phe Ser Ala
465                 470                 475                 480

Val
        485                 490                 495

<210> SEQ ID NO 19
<211> LENGTH: 1497
<212> TYPE: DNA
<213> ORGANISM: artificial sequence
<220> FEATURE:
<223> OTHER INFORMATION: Synthetic primer

<400> SEQUENCE: 19
atggcgtcta ttattatgga agtggcgacc atgcaggcga aactgaccaa aaaagaattc    60
atcgaatggc tgaaaaccag cgaaggcaaa cagtttaacg tggatctgtg gtatggcttt    120
cagtgctttg attatgcgaa cgcgggctgg aaagtgctgt ttggccatac cctgaaaggc    180

```
ctgggcgcga aagatattcc gtttgcgaat aactttgatg gcctggccac cgtgtatcag    240
aacaccccgg attttctggc ccagccgggc gatatggtgg tgtttggcag caactatggc    300
gcgggttatg gccatgtggc gtgggtgatt gaagcgaccc tggattatat catcgtgtac    360
gaacagaact ggctgggcgg tggctggacc gatcgtattg aacagccggg ctggggctgg    420
gaaaaagtga cccgtcgtca gcatgcgtac gattttccga tgtggtttat cgcccgaac    480 tttaaatctg cgacggcccc ggcgagcatt cagagcccga cccaggcgag caaaaaagaa    540
accgcgaaac cgcagccgaa agcggtggaa ctgaaaatca tcaaagatgt ggtgaaaggc    600
catgatctgc cgaaacgtgg cggcaatccg aaaggcattg tgattcataa cgatgcgggc    660
agcaaaggtg cgaccgcgga agcgtatcgt aacggcctgg tgaacgcgcc gctgagccgt    720
ctggaagcgg gcattgcgca tagctatgtg agcggcaaca ccgtgtggca ggcgctggat    780
gaaagccagg tgggctggca taccgcgaac cagctgggca caaatatta ttacggcatc    840 gaagtgtgcc agagcatggg cgcggataac gcgacctttc tgaaaaacga acaggcgacc    900
tttcaggaat gcgcgcgtct gctgaaaaaa tggggcctgc cggcgaaccg taacaccatt    960
cgtctgcata cgaatttac cagcaccagc tgcccgcatc gtagcagcgt gctgcatacc    1020
ggctttgatc cggtgacccg tggcctgctg ccggaagata acagctgca gctgaaagat    1080 tatttcatca acaaatccg cgtgtatatg gatggcaaaa ttccggtggc gaccgtgagc    1140
aacgaaagca gcgcgagcag caataccgtg aaaccggtgg cggaactgat gccgccggtt    1200
ccggccggtt ataccctgga taaaaacaac gtgccgtata aaaagaaca gggcaactat    1260 accgtggcga acgtgaaagg caacaacgtg cgtgatggct atagcaccaa cagccgtatt    1320
accggcgtgc tgccgaacaa caccaccatt acctatgatg cgcgtattg cattaacggc    1380 tatcgctgga ttacctatat cgcgaacagc ggccagcgtc gttatattgc gaccggcgaa    1440
gtggatattg cgggcaaccg tattagcagc tttggtaaat ttagcgcggt gtaataa      1497
```

<210> SEQ ID NO 20
<211> LENGTH: 520
<212> TYPE: PRT
<213> ORGANISM: artificial sequence
<220> FEATURE:
<223> OTHER INFORMATION: Synthetic peptide

<400> SEQUENCE: 20

```
Met Ala Ser Ile Ile Met Glu Val Ala Thr Met Gln Ala Lys Leu Thr
1               5                   10                  15

Lys Lys Glu Phe Ile Glu Trp Leu Lys Thr Ser Glu Gly Lys Gln Phe
            20                  25                  30

Asn Val Asp Leu Trp Tyr Gly Phe Gln Cys Phe Asp Tyr Ala Asn Ala
        35                  40                  45

Gly Trp Lys Val Leu Phe Gly His Thr Leu Lys Gly Leu Gly Ala Lys
    50                  55                  60

Asp Ile Pro Phe Ala Asn Asn Phe Asp Gly Leu Ala Thr Val Tyr Gln
65                  70                  75                  80

Asn Thr Pro Asp Phe Leu Ala Gln Pro Gly Asp Met Val Val Phe Gly
                85                  90                  95

Ser Asn Tyr Gly Ala Gly Tyr Gly His Val Ala Trp Val Ile Glu Ala
            100                 105                 110

Thr Leu Asp Tyr Ile Ile Val Tyr Glu Gln Asn Trp Leu Gly Gly Gly
        115                 120                 125

Trp Thr Asp Arg Ile Glu Gln Pro Gly Trp Gly Trp Glu Lys Val Thr
    130                 135                 140
```

Arg Arg Gln His Ala Tyr Asp Phe Pro Met Trp Phe Ile Arg Pro Asn
145                 150                 155                 160

Phe Lys Ser Ala Thr Ala Pro Ala Ser Ile Gln Ser Pro Thr Gln Ala
            165                 170                 175

Ser Lys Lys Glu Thr Ala Lys Pro Gln Pro Lys Ala Val Glu Leu Lys
        180                 185                 190

Ile Ile Lys Asp Val Val Lys Gly His Asp Leu Pro Lys Arg Gly Gly
            195                 200                 205

Asn Pro Lys Gly Ile Val Ile His Asn Asp Ala Gly Ser Lys Gly Ala
        210                 215                 220

Thr Ala Glu Ala Tyr Arg Asn Gly Leu Val Asn Ala Pro Ser Ser Arg
225                 230                 235                 240

Leu Glu Ala Gly Ile Ala His Ser Tyr Val Ser Gly Asn Thr Val Trp
                245                 250                 255

Gln Ala Leu Asp Glu Ser Gln Val Gly Trp His Thr Ala Asn Gln Leu
            260                 265                 270

Gly Asn Lys Tyr Tyr Tyr Gly Ile Glu Val Cys Gln Ser Met Gly Ala
        275                 280                 285

Asp Asn Ala Thr Phe Leu Lys Asn Glu Gln Ala Thr Phe Gln Glu Cys
290                 295                 300

Ala Arg Leu Leu Lys Lys Trp Gly Leu Pro Ala Asn Arg Asn Thr Ile
305                 310                 315                 320

Arg Leu His Asn Glu Phe Thr Ser Thr Ser Cys Pro His Arg Ser Ser
                325                 330                 335

Val Leu His Thr Gly Phe Asp Pro Val Thr Arg Gly Leu Leu Pro Glu
            340                 345                 350

Asp Lys Arg Leu Gln Leu Lys Asp Tyr Phe Ile Lys Gln Ile Arg Ala
        355                 360                 365

Tyr Met Asp Gly Lys Ile Pro Val Ala Thr Val Ser Asn Glu Ser Ser
370                 375                 380

Ala Ser Ser Asn Thr Val Lys Pro Val Ala Glu Leu Met Ser Asn Ser
385                 390                 395                 400

Thr Ala Gln Asp Pro Met Pro Phe Leu Lys Ser Ala Gly Tyr Gly Lys
                405                 410                 415

Ala Gly Gly Thr Val Thr Pro Thr Pro Asn Thr Gly Trp Lys Thr Asn
            420                 425                 430

Lys Tyr Gly Thr Leu Tyr Lys Ser Glu Ser Ala Ser Phe Thr Pro Asn
        435                 440                 445

Thr Asp Ile Ile Thr Arg Thr Thr Gly Pro Phe Arg Ser Met Pro Gln
450                 455                 460

Ser Gly Val Leu Lys Ala Gly Gln Thr Ile His Tyr Asp Glu Val Met
465                 470                 475                 480

Lys Gln Asp Gly His Val Trp Val Gly Tyr Thr Gly Asn Ser Gly Gln
                485                 490                 495

Arg Ile Tyr Leu Pro Val Arg Thr Trp Asn Lys Ser Thr Asn Thr Leu
            500                 505                 510

Gly Val Leu Trp Gly Thr Ile Lys
        515                 520

<210> SEQ ID NO 21
<211> LENGTH: 1563
<212> TYPE: DNA
<213> ORGANISM: artificial sequence
<220> FEATURE:
<223> OTHER INFORMATION: Synthetic primer

<400> SEQUENCE: 21

```
atggcaagta tcatcatgga ggtggcgaca atgcaagcaa aattaactaa aaaagagttt      60
atagagtggt tgaaaacttc tgagggaaaa caattcaatg tggacttatg gtatggattt     120
caatgctttg attatgccaa tgctggttgg aaagttttgt ttggacatac actgaaaggt     180
ttaggtgcaa agatatacc  atttgcaaac aatttcgatg gactagctac tgtataccaa     240
aatacaccgg acttttggc  acaacccggc gacatggttg tattcggtag caattacggt     300
gcaggatacg gacacgtagc atgggtaatt gaagcaactt tagattatat cattgtatat     360
gagcagaatt ggctaggcgg tggctggact gacagaatcg aacaacccgg ctggggttgg     420
gaaaaagtta caagacgaca catgcttac  gatttcccta tgtggtttat ccgtcctaac     480
ttcaaaagcg ctacagctcc agcttcaata caatctccta cgcaagcatc taaaaaggaa     540
acagctaagc acaacctaa  agcggtagaa cttaaaatta tcaaagatgt ggttaaaggt     600
catgaccttc ctaaacgtgg tggtaatcct aagggtatag ttattcataa cgacgcagga     660
agcaaagggg caacagcaga agcgtatcga acggattag  ttaacgcacc ttcatcaaga     720
ttagaagcgg tgattgcgca tagttatgta tcaggtaaca cagtgtggca gctttttagat    780
gaatcgcaag taggttggca tactgctaac caattaggca ataaatatta ttacggtatt     840
gaagtgtgtc aatcaatggg agcggataat gcgacgtttt taaaaaatga acaggcgact     900
ttccaagaat gcgctagatt gttgaaaaaa tggggattac cagcaaacag aaatacaatc     960
agattacaca cgaattcac  ttcaacatca tgcccacaca gaagctcagt attgcacact    1020
ggttttgacc cagtaactcg cggtctattg ccagaagaca gcggttgca  acttaaagac    1080
tactttatca gcagattag  ggcgtacatg gatggtaaaa taccggttgc cactgtctct    1140
aatgagtcaa gcgcttcaag taatacagtt aaaccagttg cagagctcat gtctaatagc    1200
accgcgcagg acccgatgcc gttcttgaag tcggcgggct atggcaaagc aggcggcacc    1260
gtgactccga ccccgaacac gggctggaaa accaacaagt acggtactct ttacaaaagc    1320
gagagcgcat ctttttacgcc aaacacggac atcatcacgc gcaccaccgg cccatttcgc    1380
agcatgccac agagcggcgt cttgaaagcg gccagacca  ttcactacga tgaagttatg    1440
aaacaggacg ccatgtgtg  ggtgggctat accggcaaca gcggccagcg tatttattta    1500
ccggttcgca cctggaataa aagcaccaat accttaggcg tgttatgggg taccattaag    1560
taa                                                                  1563
```

<210> SEQ ID NO 22
<211> LENGTH: 521
<212> TYPE: PRT
<213> ORGANISM: artificial sequence
<220> FEATURE:
<223> OTHER INFORMATION: Synthetic peptide

<400> SEQUENCE: 22

```
Met Ala Ser Ile Ile Met Glu Val Ala Thr Met Gln Ala Lys Leu Thr
1               5                   10                  15

Lys Lys Glu Phe Ile Glu Trp Leu Lys Thr Ser Glu Gly Lys Gln Phe
            20                  25                  30

Asn Val Asp Leu Trp Tyr Gly Phe Gln Cys Phe Asp Tyr Ala Asn Ala
        35                  40                  45

Gly Trp Lys Val Leu Phe Gly His Thr Leu Lys Gly Leu Gly Ala Lys
    50                  55                  60

Asp Ile Pro Phe Ala Asn Asn Phe Asp Gly Leu Ala Thr Val Tyr Gln
```

```
                65                  70                  75                  80
Asn Thr Pro Asp Phe Leu Ala Gln Pro Gly Asp Met Val Val Phe Gly
                        85                  90                  95
Ser Asn Tyr Gly Ala Gly Tyr Gly His Val Ala Trp Val Ile Glu Ala
                100                 105                 110
Thr Leu Asp Tyr Ile Ile Val Tyr Glu Gln Asn Trp Leu Gly Gly Gly
                115                 120                 125
Trp Thr Asp Arg Ile Glu Gln Pro Gly Trp Gly Trp Glu Lys Val Thr
            130                 135                 140
Arg Arg Gln His Ala Tyr Asp Phe Pro Met Trp Phe Ile Arg Pro Asn
145                 150                 155                 160
Phe Lys Ser Ala Thr Ala Pro Ala Ser Ile Gln Ser Pro Thr Gln Ala
                165                 170                 175
Ser Lys Lys Glu Thr Ala Lys Pro Gln Pro Lys Ala Val Glu Leu Lys
                180                 185                 190
Ile Ile Lys Asp Val Val Lys Gly His Asp Leu Pro Lys Arg Gly Gly
                195                 200                 205
Asn Pro Lys Gly Ile Val Ile His Asn Asp Ala Gly Ser Lys Gly Ala
            210                 215                 220
Thr Ala Glu Ala Tyr Arg Asn Gly Leu Val Asn Ala Pro Ser Ser Arg
225                 230                 235                 240
Leu Glu Ala Gly Ile Ala His Ser Tyr Val Ser Gly Asn Thr Val Trp
                245                 250                 255
Gln Ala Leu Asp Glu Ser Gln Val Gly Trp His Thr Ala Asn Gln Leu
                260                 265                 270
Gly Asn Lys Tyr Tyr Tyr Gly Ile Glu Val Cys Gln Ser Met Gly Ala
                275                 280                 285
Asp Asn Ala Thr Phe Leu Lys Asn Glu Gln Ala Thr Phe Gln Glu Cys
            290                 295                 300
Ala Arg Leu Leu Lys Lys Trp Gly Leu Pro Ala Asn Arg Asn Thr Ile
305                 310                 315                 320
Arg Leu His Asn Glu Phe Thr Ser Thr Ser Cys Pro His Arg Ser Ser
                325                 330                 335
Val Leu His Thr Gly Phe Asp Pro Val Thr Arg Gly Leu Leu Pro Glu
                340                 345                 350
Asp Lys Arg Leu Gln Leu Lys Asp Tyr Phe Ile Lys Gln Ile Arg Ala
                355                 360                 365
Tyr Met Asp Gly Lys Ile Pro Val Ala Thr Val Ser Asn Glu Ser Ser
            370                 375                 380
Ala Ser Ser Asn Thr Val Lys Pro Val Ala Glu Leu Met Asn Ser Phe
385                 390                 395                 400
Ser Asn Asn Thr Ala Gln Asp Pro Met Pro Phe Leu Lys Ser Ala Gly
                405                 410                 415
Tyr Gly Ser Asn Ser Thr Ser Ser Asn Asn Gly Tyr Lys Thr
                420                 425                 430
Asn Lys Tyr Gly Thr Leu Tyr Lys Ser Glu Ser Ala Ser Phe Thr Ala
            435                 440                 445
Asn Thr Asp Ile Ile Thr Arg Leu Thr Gly Pro Phe Arg Ser Met Pro
450                 455                 460
Gln Ser Gly Val Leu Arg Lys Gly Leu Thr Ile Lys Tyr Asp Glu Val
465                 470                 475                 480
Met Lys Gln Asp Gly His Val Trp Val Gly Tyr Asn Thr Asn Ser Gly
                485                 490                 495
```

Lys Arg Val Tyr Leu Pro Val Arg Thr Trp Asn Glu Ser Thr Gly Glu
        500                 505                 510

Leu Gly Pro Leu Trp Gly Thr Ile Lys
        515                 520

<210> SEQ ID NO 23
<211> LENGTH: 1566
<212> TYPE: DNA
<213> ORGANISM: artificial sequence
<220> FEATURE:
<223> OTHER INFORMATION: Synthetic primer

<400> SEQUENCE: 23

| | | |
|---|---|---|
| atggcaagta tcatcatgga ggtggcgaca atgcaagcaa aattaactaa aaaagagttt | 60 |
| atagagtggt tgaaaacttc tgagggaaaa caattcaatg tggacttatg gtatggattt | 120 |
| caatgctttg attatgccaa tgctggttgg aaagttttgt ttggacatac actgaaaggt | 180 |
| ttaggtgcaa aagatatacc atttgcaaac aatttcgatg gactagctac tgtataccaa | 240 |
| aatacaccgg acttttggc acaacccggc gacatggttg tattcggtag caattacggt | 300 |
| gcaggatacg gacacgtagc atgggtaatt gaagcaactt tagattatat cattgtatat | 360 |
| gagcagaatt ggctaggcgg tggctggact gacagaatcg aacaacccgg ctggggttgg | 420 |
| gaaaaagtta aagacgaca acatgcttac gatttcccta tgtggtttat ccgtcctaac | 480 |
| ttcaaaagcg ctacagctcc agcttcaata caatctccta cgcaagcatc taaaaaggaa | 540 |
| acagctaagc acaacctaa agcggtagaa cttaaaatta tcaaagatgt ggttaaaggt | 600 |
| catgaccttc ctaaacgtgg tggtaatcct aagggtatag ttattcataa cgacgcagga | 660 |
| agcaaagggg caacagcaga agcgtatcga aacggattag ttaacgcacc ttcatcaaga | 720 |
| ttagaagcgg gtattgcgca tagttatgta tcaggtaaca cagtgtggca agctttagat | 780 |
| gaatcgcaag taggttggca tactgctaac caattaggca ataaatatta ttacggtatt | 840 |
| gaagtgtgtc aatcaatggg agcggataat gcgacgtttt taaaaaatga acaggcgact | 900 |
| ttccaagaat gcgctagatt gttgaaaaaa tggggattac agcaaacag aaatacaatc | 960 |
| agattacaca acgaattcac ttcaacatca tgcccacaca gaagctcagt attgcacact | 1020 |
| ggttttgacc cagtaactcg cggtctattg ccagaagaca gcggttgca acttaaagac | 1080 |
| tactttatca agcagattag ggcgtacatg gatggtaaaa taccggttgc cactgtctct | 1140 |
| aatgagtcaa gcgcttcaag taatacagtt aaaccagttg cagagctcat gaatagcttt | 1200 |
| agcaataata ccgcccaaga tccgatgcca ttcttaaaaa gcgcaggcta tggtagcaac | 1260 |
| agcaccagca gcagcaacaa taacggttac aagaccaaca agtacggcac gctgtataaa | 1320 |
| agcgaaagtg cgagcttac cgcgaatacc gacatcatta cgcgattaac gggtccgttc | 1380 |
| cgcagcatgc cgcagagcgg tgttttacgc aaaggcttaa cgattaaata tgatgaagtt | 1440 |
| atgaaacagg acggccatgt gtgggtgggt tataacacga acagcggcaa acgcgtttac | 1500 |
| ttaccggtgc gtacgtggaa cgagagcacc ggtgaattag ccccgctgtg gggcaccatc | 1560 |
| aaataa | 1566 |

<210> SEQ ID NO 24
<211> LENGTH: 123
<212> TYPE: PRT
<213> ORGANISM: unknown
<220> FEATURE:
<223> OTHER INFORMATION: Lysostaphin

<400> SEQUENCE: 24

```
Ser Asn Ser Thr Ala Gln Asp Pro Met Pro Phe Leu Lys Ser Ala Gly
1               5                   10                  15

Tyr Gly Lys Ala Gly Gly Thr Val Thr Pro Thr Pro Asn Thr Gly Trp
            20                  25                  30

Lys Thr Asn Lys Tyr Gly Thr Leu Tyr Lys Ser Glu Ser Ala Ser Phe
            35                  40                  45

Thr Pro Asn Thr Asp Ile Ile Thr Arg Thr Thr Gly Pro Phe Arg Ser
50                      55                  60

Met Pro Gln Ser Gly Val Leu Lys Ala Gly Gln Thr Ile His Tyr Asp
65                  70                  75                  80

Glu Val Met Lys Gln Asp Gly His Val Trp Val Gly Tyr Thr Gly Asn
                85                  90                  95

Ser Gly Gln Arg Ile Tyr Leu Pro Val Arg Thr Trp Asn Lys Ser Thr
            100                 105                 110

Asn Thr Leu Gly Val Leu Trp Gly Thr Ile Lys
            115                 120
```

<210> SEQ ID NO 25
<211> LENGTH: 372
<212> TYPE: DNA
<213> ORGANISM: unknown
<220> FEATURE:
<223> OTHER INFORMATION: Lysostaphin

<400> SEQUENCE: 25

```
tctaatagca ccgcgcagga cccgatgccg ttcttgaagt cggcgggcta tggcaaagca    60
ggcggcaccg tgactccgac cccgaacacg ggctggaaaa ccaacaagta cggtactctt   120
tacaaaagcg agagcgcatc tttttacgcca aacacggaca tcatcacgcg caccaccggc   180
ccatttcgca gcatgccaca gagcggcgtc ttgaaagcgg ccagaccat tcactacgat    240
gaagttatga acaggacgg ccatgtgtgg gtgggctata ccggcaacag cggccagcgt    300
atttatttac cggttcgcac ctggaataaa agcaccaata ccttaggcgt gttatggggt    360
accattaagt aa                                                        372
```

<210> SEQ ID NO 26
<211> LENGTH: 124
<212> TYPE: PRT
<213> ORGANISM: unknown
<220> FEATURE:
<223> OTHER INFORMATION: ALE1

<400> SEQUENCE: 26

```
Asn Ser Phe Ser Asn Asn Thr Ala Gln Asp Pro Met Pro Phe Leu Lys
1               5                   10                  15

Ser Ala Gly Tyr Gly Ser Asn Ser Thr Ser Ser Ser Asn Asn Asn Gly
            20                  25                  30

Tyr Lys Thr Asn Lys Tyr Gly Thr Leu Tyr Lys Ser Glu Ser Ala Ser
            35                  40                  45

Phe Thr Ala Asn Thr Asp Ile Ile Thr Arg Leu Thr Gly Pro Phe Arg
50                      55                  60

Ser Met Pro Gln Ser Gly Val Leu Arg Lys Gly Leu Thr Ile Lys Tyr
65                  70                  75                  80

Asp Glu Val Met Lys Gln Asp Gly His Val Trp Val Gly Tyr Asn Thr
                85                  90                  95

Asn Ser Gly Lys Arg Val Tyr Leu Pro Val Arg Thr Trp Asn Glu Ser
            100                 105                 110

Thr Gly Glu Leu Gly Pro Leu Trp Gly Thr Ile Lys
```

<210> SEQ ID NO 27
<211> LENGTH: 375
<212> TYPE: DNA
<213> ORGANISM: unknown
<220> FEATURE:
<223> OTHER INFORMATION: ALE1

<400> SEQUENCE: 27

```
aatagcttta gcaataatac cgcccaagat ccgatgccat tcttaaaaag cgcaggctat      60
ggtagcaaca gcaccagcag cagcaacaat aacggttaca agaccaacaa gtacggcacg     120
ctgtataaaa gcgaaagtgc gagctttacc gcgaataccg acatcattac gcgattaacg     180
ggtccgttcc gcagcatgcc gcagagcggt gttttacgca aaggcttaac gattaaatat     240
gatgaagtta tgaaacagga cggccatgtg tgggtgggtt ataacacgaa cagcggcaaa     300
cgcgtttact taccggtgcg tacgtggaac gagagcaccg gtgaattagg cccgctgtgg     360
ggcaccatca aataa                                                     375
```

<210> SEQ ID NO 28
<211> LENGTH: 497
<212> TYPE: PRT
<213> ORGANISM: artificial
<220> FEATURE:
<223> OTHER INFORMATION: Synthetic peptide

<400> SEQUENCE: 28

```
Met Ala Ser Ile Ile Met Glu Val Ala Thr Met Gln Ala Lys Leu Thr
1               5                   10                  15
Lys Lys Glu Phe Ile Glu Trp Leu Lys Thr Ser Glu Gly Lys Gln Phe
            20                  25                  30
Asn Val Asp Leu Trp Tyr Gly Phe Gln Cys Phe Asp Tyr Ala Asn Ala
        35                  40                  45
Gly Trp Lys Val Leu Phe Gly Leu Leu Leu Lys Gly Leu Gly Ala Lys
    50                  55                  60
Asp Ile Pro Phe Ala Asn Asn Phe Asp Gly Leu Ala Thr Val Tyr Gln
65                  70                  75                  80
Asn Thr Pro Asp Phe Leu Ala Gln Pro Gly Asp Met Val Val Phe Gly
                85                  90                  95
Ser Asn Tyr Gly Ala Gly Tyr Gly His Val Ala Trp Val Ile Glu Ala
            100                 105                 110
Thr Leu Asp Tyr Ile Ile Val Tyr Glu Gln Asn Trp Leu Gly Gly Gly
        115                 120                 125
Trp Thr Asp Arg Ile Glu Gln Pro Gly Trp Gly Trp Glu Lys Val Thr
    130                 135                 140
Arg Arg Gln His Ala Tyr Asp Phe Pro Met Trp Phe Ile Arg Pro Asn
145                 150                 155                 160
Phe Lys Ser Glu Thr Ala Pro Arg Ser Ile Gln Ser Pro Thr Gln Ala
                165                 170                 175
Ser Lys Lys Glu Thr Ala Lys Pro Gln Pro Lys Ala Val Glu Leu Lys
            180                 185                 190
Ile Ile Lys Asp Val Val Lys Gly Tyr Asp Leu Pro Lys Arg Gly Gly
        195                 200                 205
Asn Pro Lys Gly Ile Val Ile His Asn Asp Ala Gly Ser Lys Gly Ala
    210                 215                 220
Thr Ala Glu Ala Tyr Arg Asn Gly Leu Val Asn Ala Pro Ser Ser Arg
225                 230                 235                 240
```

```
Leu Glu Ala Gly Ile Ala His Ser Tyr Val Ser Gly Asn Thr Val Trp
            245         250                 255

Gln Ala Leu Asp Glu Ser Gln Val Gly Trp His Thr Ala Asn Gln Leu
            260         265                 270

Gly Asn Lys Tyr Tyr Gly Ile Glu Val Cys Gln Ser Met Gly Ala
            275             280             285

Asp Asn Ala Thr Phe Leu Lys Asn Glu Gln Ala Thr Phe Gln Glu Cys
    290             295                 300

Ala Arg Leu Leu Lys Lys Trp Gly Leu Pro Ala Asn Arg Asn Thr Ile
305             310             315                 320

Arg Leu His Asn Glu Phe Thr Ser Thr Ser Cys Pro His Arg Ser Ser
            325             330                 335

Val Leu His Thr Gly Phe Asp Pro Val Thr Arg Gly Leu Leu Pro Glu
            340             345             350

Asp Lys Arg Leu Gln Leu Lys Asp Tyr Phe Ile Lys Gln Ile Arg Ala
            355             360             365

Tyr Met Asp Gly Lys Ile Pro Val Ala Thr Val Ser Asn Glu Ser Ser
    370             375             380

Ala Ser Ser Asn Thr Val Lys Pro Val Ala Glu Leu Met Pro Pro Val
385             390             395                 400

Pro Ala Gly Tyr Thr Leu Asp Lys Asn Asn Val Pro Tyr Lys Lys Glu
            405             410             415

Gln Gly Asn Tyr Thr Val Ala Asn Val Lys Gly Asn Asn Val Arg Asp
            420             425             430

Gly Tyr Ser Thr Asn Ser Arg Ile Thr Gly Val Leu Pro Asn Asn Thr
            435             440             445

Thr Ile Thr Tyr Asp Gly Ala Tyr Cys Ile Asn Gly Tyr Arg Trp Ile
    450             455             460

Thr Tyr Ile Ala Asn Ser Gly Gln Arg Arg Tyr Ile Ala Thr Gly Glu
465             470             475             480

Val Asp Ile Ala Gly Asn Arg Ile Ser Ser Phe Gly Lys Phe Ser Ala
            485             490             495

Val
```